United States Patent
Kato et al.

(10) Patent No.: US 9,257,576 B2
(45) Date of Patent: Feb. 9, 2016

(54) AMINO ACID GENERATOR AND POLYSILOXANE COMPOSITION CONTAINING THE SAME

(71) Applicant: NISSAN CHEMICAL INDUSTRIES, LTD., Tokyo (JP)

(72) Inventors: Taku Kato, Funabashi (JP); Junpei Kobayashi, Funabashi (JP); Satoko Takano, Funabashi (JP); Naoki Sakumoto, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 124 days.

(21) Appl. No.: 13/941,890

(22) Filed: Jul. 15, 2013

(65) Prior Publication Data

US 2013/0313669 A1    Nov. 28, 2013

Related U.S. Application Data

(62) Division of application No. 12/993,700, filed as application No. PCT/JP2009/059193 on May 19, 2009, now abandoned.

(30) Foreign Application Priority Data

May 21, 2008  (JP) .................. 2008-132793
Jun. 9, 2008  (JP) .................. 2008-150327
Jun. 26, 2008  (JP) .................. 2008-166914

(51) Int. Cl.
*C08K 5/17* (2006.01)
*H01L 31/0216* (2014.01)
*C07B 51/00* (2006.01)
*C08L 83/04* (2006.01)
*C09D 7/12* (2006.01)
*C09D 183/04* (2006.01)
*H01L 27/146* (2006.01)
*C08K 5/16* (2006.01)

(52) U.S. Cl.
CPC ............ *H01L 31/0216* (2013.01); *C07B 51/00* (2013.01); *C08L 83/04* (2013.01); *C09D 7/1233* (2013.01); *C09D 183/04* (2013.01); *H01L 27/14601* (2013.01); *C08K 5/16* (2013.01); *H01L 27/14621* (2013.01); *H01L 27/14627* (2013.01); *H01L 27/14683* (2013.01); *Y02P 20/55* (2015.11)

(58) Field of Classification Search
CPC .................................. C08K 5/175; C08K 5/54
USPC ........................................ 524/238, 241, 247
See application file for complete search history.

(56) References Cited

U.S. PATENT DOCUMENTS 3,784,523 A * 1/1974 Loffet ........................... 525/184
7,795,467 B1 * 9/2010 Pacetti et al. ................. 560/336

FOREIGN PATENT DOCUMENTS

| JP | A-57-189131 | 11/1982 |
|---|---|---|
| JP | A-62-281828 | 12/1987 |
| JP | A-6-25283 | 2/1994 |
| JP | A-6-145599 | 5/1994 |
| JP | A-08-217662 | 8/1996 |
| JP | 2533507 B2 * | 9/1996 |
| JP | A-2003-226837 | 8/2003 |
| JP | A-2006-96983 | 4/2006 |
| JP | A-2007-211061 | 8/2007 |
| JP | A-2008-7640 | 1/2008 |

OTHER PUBLICATIONS

Machine translation of JP 2533507 B2, 1996.*
Nov. 22, 2012 Chinese Office Action issued in Chinese Patent Application No. 200980118183.4 (with English-language Translation).
International Search Report issued in International Application No. PCT/JP2009/059193 on Sep. 1, 2009 (with translation).

* cited by examiner

*Primary Examiner* — Wenwen Cai
(74) *Attorney, Agent, or Firm* — Oliff PLC

(57) ABSTRACT

A coating film forming composition includes an amino acid generator including a protecting group that is eliminated to generate an amino acid. A coating film forming composition includes a component (A): the amino acid generator; a component (B): a hydrolyzable silane, a hydrolysis product thereof, a hydrolysis-condensation product thereof, or a mixture thereof; and a component (C): a solvent.

12 Claims, 32 Drawing Sheets

EXAMPLE 43

EXAMPLE 44

EXAMPLE 45

AMINO ACID GENERATOR AND POLYSILOXANE COMPOSITION CONTAINING THE SAME

This is a divisional of application Ser. No. 12/993,700 filed Dec. 2, 2010, which is a National Stage of PCT/JP2009/059193 filed May 19, 2009, and claims the benefit of Japanese Application No. 2008-132793 filed May 21, 2008, and Japanese Application No. 2008-150327 filed May Jun. 9, 2008 and Japanese Application No. 2008-166914 filed Jun. 26, 2008. The entire disclosures of the prior applications are hereby incorporated by reference herein in their entirety.

I. TECHNICAL FIELD

The present invention relates to an amino acid generator and a polysiloxane composition containing the same. More in detail, the present invention relates to: an amino acid generator in which an amino group is protected while a carboxy group remains, and by subjecting the amino acid generator to treatment such as heating, a protecting group for the amino group is eliminated to generate an amino acid; and a coating film forming composition using the amino acid generator and a polysiloxane composition containing the amino acid generator.

BACKGROUND ART

A polysiloxane is researched and developed for utilizing the polysiloxane as one member of an electronic device, particularly a solid state imaging device by taking advantage of high transparency and high heat resistance due to a Si—O bond. The incorporation of the polysiloxane into an electronic device is performed through a process of coating an arbitral substrate with the polysiloxane by a wet process such as a spin coating method, and thus it is essential to prepare the polysiloxane as a polysiloxane vanish. The polysiloxane after the film formation thereof is generally baked using an arbitral baking equipment.

By baking the polysiloxane, intramolecular and intermolecular Si—OH bonds are condensation-polymerized with each other and the polysiloxane is polymerized to a polymer to form a rigid film. However, in the case where the condensation-polymerization of the Si—OH bond is imperfect, when the polysiloxane is incorporated into an electronic device, particularly a solid state imaging device as one member thereof, Si—OH bonds remaining after an aging test at a high temperature of the electronic device in a post-process are condensation-polymerized again and by dehydration of the electronic device, degasification is caused, so that the reliability of the electronic device is remarkably impaired. Accordingly, for solving this problem, remaining Si—OH bonds are necessary to be digested.

Thus, conventionally, there have been known methods such as (1) adding a baking process at a high temperature and for a long period, and (2) accelerating the condensation-polymerization by adding a thermobase generator to a reaction system to bake the polysiloxane (see Patent Document 1). The addition of the thermobase generator utilizes such a property that Si—OH bonds of the polysiloxane easily cause the condensation-polymerization of each other under a basic condition, and is effective for digesting remaining Si—OH bonds. A hitherto-reported thermobase generator accelerates the condensation-polymerization during baking by adding a primary amine or a secondary amine that is a moiety developing basicity in a high activity state into the thermobase generator or by adding a tertiary amine into the thermobase generator. However, there has been known that on the contrary, the preservation stability of a polysiloxane vanish in a frozen state, in a refrigerated state, or at room temperature is poor.

On the other hand, it is generally known that an acidic range of around pH 4 is a stable range for the preservation stability of a polysiloxane vanish in which the condensation-polymerization cannot be caused and a hydrolysis cannot be progressed. Conventionally, for enhancing the preservation stability of a polysiloxane vanish in a reaction system to which a thermobase generator is added, it is necessary to adjust pH to around 4, and a method of further newly adding a derivative of a carboxylic acid such as oxalic acid and maleic acid to the reaction system or similar methods are used for this adjustment.

However, the addition of the thermobase generator is effective for digesting remaining Si—OH bonds, but conversely unpreferably impairs the preservation stability of a polysiloxane vanish.

Then, there is required a polysiloxane composition capable of forming a polysiloxane film in which Si—OH bonds are remarkably digested during film formation/baking while advantageously maintaining the preservation stability of a polysiloxane vanish. There are also disclosed curable resin compositions containing a polysiloxane and an organic crosslinker (Patent Documents 2 to 4).

RELATED-ART DOCUMENT

Patent Document

Patent Document 1: Japanese Patent Application Publication No. JP-A-6-145599
Patent Document 2: Japanese Patent Application Publication No. JP-A-2006-96983
Patent Document 3: Japanese Patent Application Publication No. JP-A-2008-7640
Patent Document 4: Japanese Patent Application Publication No. JP-A-2003-226837

II. DISCLOSURE OF THE INVENTION

Problems to be Solved by the Invention

In order to solve the problems described above, it is an object of the present invention to provide a coating film forming composition using a polysiloxane composition having advantageous preservation stability of a polysiloxane vanish and developing an effect of accelerating the condensation-polymerization of remaining Si—OH bonds. It is another object of the present invention to provide a coating film forming composition using a polysiloxane composition capable of preventing a slit or a crack of a cured product thereof.

Means for Solving the Problem

As a result of assiduous research intended to overcome these disadvantages, the inventors of the present invention have found that a polysiloxane composition in which an amino acid generator is added to a polysiloxane is effective as a coating film forming composition capable of making the preservation stability of a polysiloxane vanish advantageous, accelerating the condensation-polymerization during baking of the composition, and remarkably reducing remaining Si—OH bonds.

The inventors of the present invention also have found that when the amino acid generator is used in an electronic material field, it develops a novel action effect.

That is, the present invention provides the followings.

According to a first aspect, an amino acid generator includes a protecting group that is eliminated to generate an amino acid.

According to a second aspect, a thermo amino acid generator includes a protecting group that is eliminated by heat to generate an amino acid.

According to a third aspect, a photo amino acid generator includes a protecting group that is eliminated by light to generate an amino acid.

According to a fourth aspect, the amino acid generator according to any one of the first aspect to the third aspect in which the amino acid generator is a compound of Formula (1):

D-A        Formula (1)

(where D is a protecting group for an amino group, and A is an organic group remaining after subtracting hydrogen atoms from an amino group of an amino acid).

According to a fifth aspect, the amino acid generator according to the fourth aspect in which the amino acid generator is a compound of Formula (2):

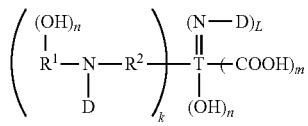

Formula (2)

(where D is a protecting group for an amino group; $R^1$ is a hydrogen atom (when n is 0) or an alkylene group; $R^2$ is a single bond, an alkylene group, or an arylene group; $R^1$ and $R^2$ together with a nitrogen atom of an amino group to which $R^1$ and $R^2$ are bonded may form a cyclic structure; T is a single bond or a (k+2L+n+m)-valent organic group that is a $C_{1-10}$ alkyl group or $C_{6-40}$ aryl group that may contain an amino group, a thiol group, or a carbonyl group; k is an integer of 1 to 4; L is an integer of 0 to 2; n is an integer of 0 to 2; and m is an integer of 1 to 4).

According to a sixth aspect, the amino acid generator according to the fourth aspect in which the protecting group D is an esterified carboxy residue having an alkoxycarbonyl structure.

According to a seventh aspect, the amino acid generator according to the fourth aspect in which the protecting group D is a tert-butoxycarbonyl group or a 9-fluorenylmethoxycarbonyl group.

According to an eighth aspect, the amino acid generator according to any one of the first aspect to the third aspect in which the amino acid generator is at least one type of compound selected from compounds of Formula (2-1) to Formula (2-22):

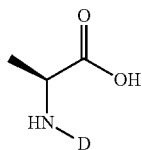

Formula (2-1)

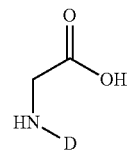

Formula (2-2)

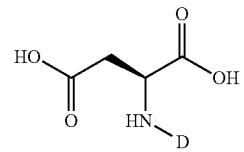

Formula (2-3)

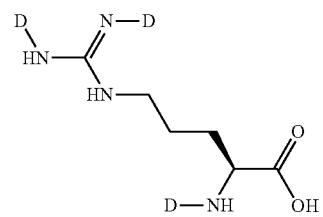

Formula (2-4)

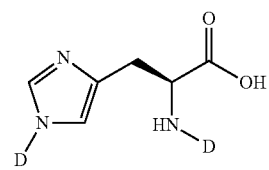

Formula (2-5)

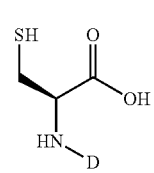

Formula (2-6)

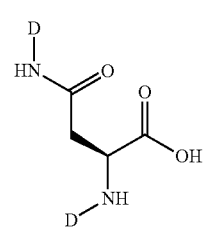

Formula (2-7)

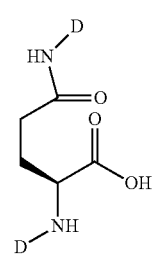

Formula (2-8)

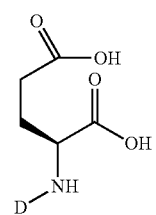

Formula (2-9)

Formula (2-10)
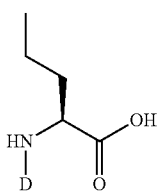

Formula (2-11)
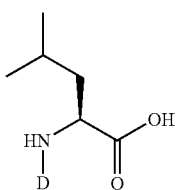

Formula (2-12)
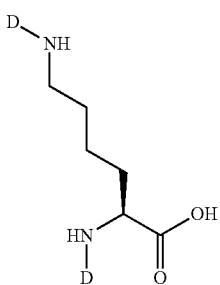

Formula (2-13)
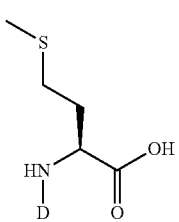

Formula (2-14)
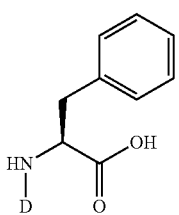

Formula (2-15)
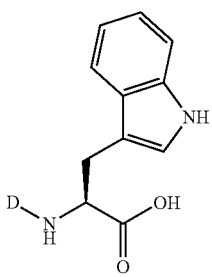

Formula (2-16)
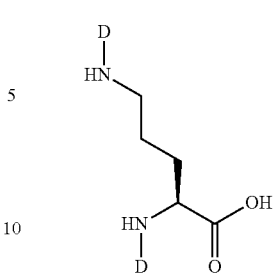

Formula (2-17)
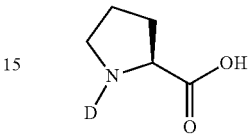

Formula (2-18)

Formula (2-19)
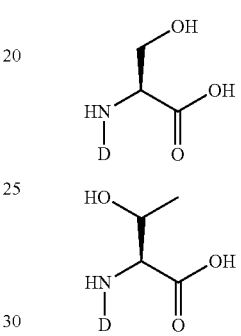

Formula (2-20)
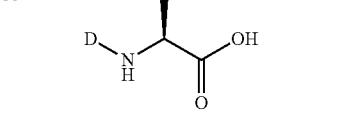

Formula (2-21)
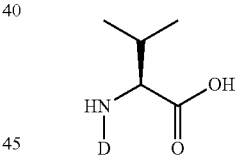

Formula (2-22)

(where D is a protecting group for an amino group).

According to a ninth aspect, a coating film forming composition contains the amino acid generator as described in any one of the first aspect to the eighth aspect.

According to a tenth aspect, a coating film forming composition contains a component (A): the amino acid generator as described in any one of the first aspect to the eighth aspect, a component (B): a hydrolyzable silane, a hydrolysis product thereof, a hydrolysis-condensation product thereof, or a mixture thereof, and a component (C): a solvent.

According to an eleventh aspect, the coating film forming composition according to the tenth aspect in which the component (B) is at least one type of hydrolyzable silane selected from a group consisting of hydrolyzable silanes of Formula (3) and Formula (4):

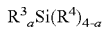   Formula (3)

(where $R^3$ is an alkyl group, an aryl group, a halogenated alkyl group, a halogenated aryl group, an alkenyl group, or an organic group having an epoxy group, an acryloyl group, a methacryloyl group, a mercapto group, an amino group, a carboxy group, a phosphate group, an amide group, a nitro group, an acyl group, a sulfonic group, a cyano group, or a combination thereof, where $R^3$ is bonded to a silicon atom through a Si—C bond; $R^4$ is an alkoxy group, an acyloxy group, or a halogen atom; and a is an integer of 0 to 3)

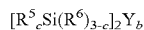   Formula (4)

(where $R^5$ is an alkyl group, an aryl group, a halogenated alkyl group, a halogenated aryl group, an alkenyl group, or an organic group having an epoxy group, an acryloyl group, a methacryloyl group, a mercapto group, an amino group, a carboxy group, a phosphate group, an amide group, a nitro group, an acyl group, a sulfonic group, a cyano group, or a combination thereof, where $R^5$ is bonded to a silicon atom through a Si—C bond; $R^6$ is an alkoxy group, an acyloxy group, or a halogen atom; Y is an alkylene group or an arylene group; b is an integer of 0 or 1; and c is an integer of 0 or 1), a hydrolysis product thereof, a hydrolysis-condensation product thereof, or a mixture thereof.

According to a twelfth aspect, the coating film forming composition according to the eleventh aspect in which the component (B) is at least one type of hydrolyzable silane selected from a group consisting of hydrolyzable silanes of Formula (3) (where a is 0 to 2), a hydrolysis product thereof, a hydrolysis-condensation product thereof, or a mixture thereof.

According to a thirteenth aspect, the coating film forming composition according to any one of the tenth aspect to the twelfth aspect, further containing a crosslinkable compound as a component (D).

According to a fourteenth aspect, the coating film forming composition according to the thirteenth aspect in which the component (D) contains a crosslinkable compound having in the molecule thereof, at least two functional groups of Formula (D-1):

—CH$_2$—O—R$^1$   Formula (D-1)

(where $R^1$ is a hydrogen atom or a $C_{1-10}$ alkyl group).

According to a fifteenth aspect, the coating film forming composition according to the thirteenth aspect in which the component (D) is a crosslinkable compound of Formula (D-2):

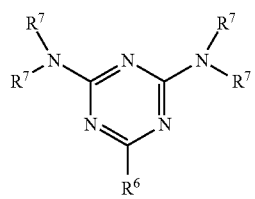   Formula (D-2)

[where $R^6$ is a hydrogen atom, a $C_{1-10}$ alkyl group, an aryl group, an aralkyl group, an alkenyl group, or a functional group of Formula (D-3):

   Formula (D-3)

{where $R^7$ is a hydrogen atom or a functional group of Formula (D-1)}; and $R^7$ is a hydrogen atom or a functional group of Formula (D-1), where the crosslinkable compound of Formula (D-2) has in the molecule thereof, two to six functional groups of Formula (D-1)]
or a crosslinkable compound of Formula (D-4):

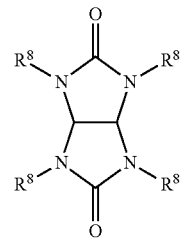   Formula (D-4)

{where $R^8$ is a hydrogen atom or a functional group of Formula (D-1), where the crosslinkable compound of Formula (D-4) has in the molecule thereof, two to four functional groups of Formula (D-1)}.

According to a sixteenth aspect, an electronic device contains a film formed from the coating film forming composition as described in any one of the ninth aspect to the fifteenth aspect.

According to a seventeenth aspect, a solid state imaging device contains a charge coupled device (CCD) or a complementary metal oxide film semiconductor (CMOS) that contains a film formed from the coating film forming composition as described in any one of the ninth aspect to the fifteenth aspect.

According to an eighteenth aspect, a solid state imaging device contains a film formed from the coating film forming composition as described in any one of the ninth aspect to the fifteenth aspect as a planarization layer on a color filter.

According to a nineteenth aspect, a solid state imaging device contains a film formed from the coating film forming composition as described in any one of the ninth aspect to the fifteenth aspect as a planarization layer or a conformal layer on a microlens.

Effects of the Invention

The amino acid generator (such as a thermo amino acid generator and a photo amino acid generator) of the present invention acts as an acid component in the coating film forming composition using the polysiloxane composition containing the amino acid generator, so that the amino acid generator and the coating film forming composition have advantageous preservation stability of a polysiloxane vanish.

When heat or light as an external energy is applied to the amino acid generator and the coating film forming composition using the polysiloxane composition containing the amino acid generator, after the film formation thereof and during baking or light irradiation thereof, a protecting group for an amino group of the amino acid generator is eliminated and the resultant amino acid accelerates the condensation-polymerization of the polysiloxane, so that a rigid film can be formed without an unreacted Si—OH bond remaining.

Further, in a coating film formed from the coating film forming composition using the amino acid generator and the polysiloxane composition containing the amino acid generator, during baking or light irradiation thereof, unreacted Si—OH bonds are digested. Therefore, when the coating film is incorporated into an electronic device, particularly a solid state imaging device as one member thereof, it is not caused that Si—OH bonds remaining after an aging test at a high temperature of the electronic device in a post-process are condensation-polymerized again and that by dehydration of the electronic device, degasification is caused. As a result, the reliability of the electronic device can be remarkably enhanced.

The coating film formed from the coating film forming composition using the amino acid generator of the present invention and the polysiloxane composition containing the amino acid generator remarkably accelerates the condensation-polymerization during baking thereof, so that the coating film can shorten the baking time when arbitral baking equipment is used and can lower the baking temperature. The shortening of the baking time can shorten the tact time of the film production and can enhance the throughput of the device production. The lowering of the baking temperature makes possible a low temperature baking, which could not be achieved by a conventional polysiloxane composition and the coating film can be applied to a flexible base material incapable of corresponding to a high temperature baking.

The coating film formed from the coating film forming composition containing the amino acid generator of the present invention remarkably accelerates the condensation-polymerization during exposure thereof, so that the coating film can reduce an exposure amount when an arbitral exposing apparatus is used. The reduction of the exposure amount can shorten the tact time of the film production and can enhance the throughput of the device production. The polysiloxane composition containing the amino acid generator of the present invention accelerates the condensation-polymerization by the exposure, so that the polysiloxane composition can be applied to a flexible base material, which could not be achieved by a conventional high temperature curing-type polysiloxane.

The amino acid generator of the present invention and the polysiloxane composition containing the amino acid generator can control pH during the preparation of a polysiloxane vanish and the baking by varying the type of the amino acid generator, so that various polysiloxane compositions corresponding to the device type to be produced and various baking processes can be designed and the process margin can be enlarged. Thus, the polysiloxane composition of the present invention can preferably be used as one member of an electronic device, particularly a solid state imaging device.

In a filled cured product obtained by coating with the coating film forming composition using the amino acid generator of the present invention and the polysiloxane composition containing the amino acid generator, there is caused neither such a phenomenon that a gap is caused between the cured product and a wall of the filled part, that is, the slit, nor such a phenomenon that a crack is caused in the filled cured product, that is, the crack.

In the present invention, the polysiloxane composition containing an organic crosslinkable compound suppresses a sudden volume contraction of the polysiloxane obtained by the involvement of the organic crosslinkable compound in a reaction with a silanol group at a siloxane terminal to enhance the recovery rate of the film (coating film property), so that the polysiloxane composition can enhance, for example filling property in a via to enhance the reliability of a device.

Further, by blending the composition containing the polysiloxane and the organic crosslinkable compound with the amino acid generator as a curing accelerator, there can be obtained both effects of accelerating the effect of the polysiloxane and preventing a slit and a crack of the resultant polysiloxane cured product.

The amino acid generator used in the present invention is originally a medicine intermediate mainly used for a bioactivity research, a pathogenic gene research, and the like in the medicine field, so that the supplying property thereof during the production of the amino acid generator is stable.

BEST MODES FOR CARRYING OUT THE INVENTION

Figure 1:
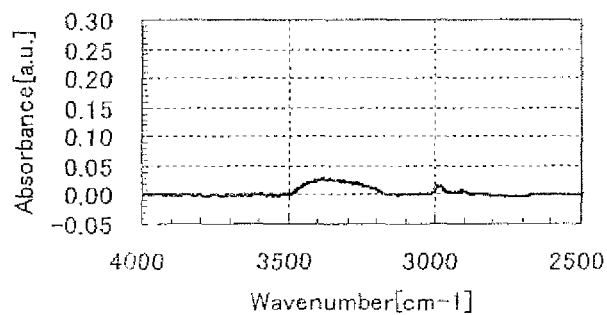
FIG. 1 is a graph showing an FT-IR spectrum of the film obtained in Example 19.

In the amino acid generator of the present invention, an amino group is protected by a protecting group and by an action of heating or light irradiation (exposure), the protecting group is eliminated to generate an amino acid.

Examples of the amino acid generator include: a thermo amino acid generator in which by heat during heating, a protecting group is eliminated to generate an amino acid that is a curing accelerating component of a silanol; and a photo amino acid generator in which by an action of exposure or the like, a protecting group is eliminated to generate an amino acid that is a curing accelerating component of a silanol.

The amino acid generator is a compound of Formula (1):

D–A      Formula (1)

In Formula (1), D is a protecting group for an amino group and A is an organic group remaining after subtracting hydrogen atoms from an amino group of an amino acid. The protecting group D is preferably an esterified carboxy residue having an alkoxycarbonyl structure. When the esterified carboxy residue is eliminated as a protecting group, the carboxy residue pulls hydrogen atoms out of a silanol group at a polysiloxane terminal so that an amino group is generated in the amino acid generator to generate an amino acid and the amino group causes a dehydration-condensation of silanol groups to generate a polymerized polysiloxane. It is considered that the protecting group D is reacted also with water generated by the dehydration-condensation or with a water content in the reaction system and the protecting group D itself is decomposed to an alcohol or a carbonic acid gas.

Examples of the protecting group D include $C_{2-21}$ linear or branched alkoxycarbonyl groups that may be substituted such as a 9-fluorenylmethoxycarbonyl group, a methoxycarbonyl group, a trifluoromethoxycarbonyl group, an ethoxycarbonyl group, an n-propoxycarbonyl group, an isopropoxycarbonyl group, an n-butoxycarbonyl group, a tert-butoxycarbonyl group, a sec-butoxycarbonyl group, an n-pentyloxycarbonyl group, and an n-hexyloxycarbonyl group.

Particularly preferred are a tert-butoxycarbonyl group and a 9-fluorenylmethoxycarbonyl group that are bulky and easily eliminated shown below.

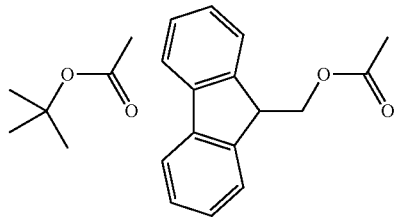

The amino acid generator is a compound of Formula (2):

Formula (2)

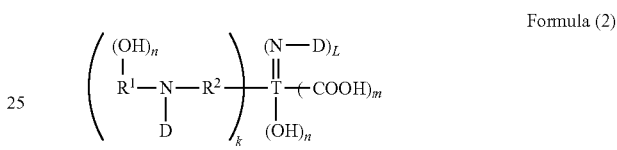

In Formula (2), D is a protecting group for an amino group, $R^1$ is a hydrogen atom (when n is 0) or an alkylene group, and $R^2$ is a single bond, an alkylene group, or an arylene group. $R^1$ and $R^2$ together with a nitrogen atom of an amino group to which $R^1$ and $R^2$ are bonded may form a cyclic structure and T is a single bond or a (k+2L+n+m)-valent organic group, where examples of the organic group include $C_{1-10}$ alkyl groups and $C_{6-40}$ aryl groups which may contain an amino group, a thiol group, or a carbonyl group. When T is a single bond, a (=N-D) group and a (—OH) group that are directly bonded to T do not exist and a bond of T with $R^2$ and a carboxy group is formed. k is an integer of 1 to 4, L is an integer of 0 to 2, n is an integer of 0 to 2, and m is an integer of 1 to 4.

Examples of the $C_{1-10}$ alkyl group include a methyl group, an ethyl group, an n-propyl group, an isopropyl group, a cyclopropyl group, an n-butyl group, an isobutyl group, a sec-butyl group, a tert-butyl group, a cyclobutyl group, a 1-methyl-cyclopropyl group, a 2-methyl-cyclopropyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-isopropyl-cyclopropyl group, a 2-isopropyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Examples of the alkylene group include alkylene groups corresponding to the above alkyl groups.

Examples of the $C_{6-40}$ aryl group include a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

Examples of the arylene group include arylene groups corresponding to the above aryl groups.

The amino acid generator may be in a structure containing at least one relative configuration among an L form, a D form, and a mixture of L form and D form. Specific examples of the compounds of Formula (2-1) to Formula (2-22) include compounds in which one or more nitrogen atom(s) at an amine moiety contained in an amino acid is (are) substituted with a tert-butoxycarbonyl group or a 9-fluorenylmethoxycarbonyl group. In an amino acid generator having in the molecule thereof a plurality of protecting groups, either a tert-butoxycarbonyl group or a 9-fluorenylmethoxycarbonyl group can function as a plurality of protecting groups, or a combination of a tert-butoxycarbonyl group and a 9-fluorenylmethoxycarbonyl group can function as a protecting group.

Examples of such an amino acid generator include: N-α-tert-butoxycarbonyl-L-alanine, N-α-tert-butoxycarbonyl-D-alanine, N-α-tert-butoxycarbonyl-DL-alanine, N-α-tert-butoxycarbonyl-N-methyl-L-alanine, N-α-tert-butoxycarbonyl-β-alanine, N-α, N-ω1, N-ω2-tri-tert-butoxycarbonyl-N-methyl-L-arginine, N-α, N-ω1, N-ω2-tri-tert-butoxycarbonyl-L-arginine, N-α-tert-butoxycarbonyl-L-arginine, N-α-tert-butoxycarbonyl-N-ω1, N-ω2-bis-carbobenzoxy-L-arginine, N-α-tert-butoxycarbonyl-N-ω1, N-ω2-bis-carbobenzoxy-D-arginine, N-α-tert-butoxycarbonyl-L-asparagine, N-α-tert-butoxycarbonyl-D-asparagine, N-α-tert-butoxycarbonyl-L-asparagine, N-α-tert-butoxycarbonyl-L-isoasparagine, N-α-tert-butoxycarbonyl-D-isoasparagine, N-α-tert-butoxycarbonyl-N-β-trityl-L-asparagine, N-α-tert-butoxycarbonyl-L-aspartic acid, N-α-tert-butoxycarbonyl-D-aspartic acid, N-α-tert-butoxycarbonyl-L-aspartic acid β-methyl ester, N,N'-di-tert-butoxycarbonyl-L-cysteine, N-α-tert-butoxycarbonyl-S-acetamidomethyl-L-cysteine, N-α-tert-butoxycarbonyl-S-benzyl-L-cysteine, N-α-tert-butoxycarbonyl-S-p-methylbenzyl-L-cysteine, N-α-tert-butoxycarbonyl-L-glutamine, N-α-tert-butoxycarbonyl-D-glutamine, N-α-tert-butoxycarbonyl-L-isoglutamine, N-α-tert-butoxycarbonyl-D-isoglutamine, N-α-tert-butoxycarbonyl-N-γ-trityl-L-glutamine, N-α-tert-butoxycarbonyl-L-glutamic acid, N-α-tert-butoxycarbonyl-D-glutamic acid, N-α-tert-butoxycarbonyl-L-glutamic acid α-tert-butyl ester, N-α-tert-butoxycarbonyl-L-glutamic acid γ-cyclohexyl ester, N-tert-butoxycarbonyl-glycine, N-tert-butoxycarbonyl-glycyl-glycyl-glycine, N-tert-butoxycarbonyl-glycyl-glycyl-glycyl-glycyl-glycine, N-tert-butoxycarbonyl-glycine-methyl ester, N-α-tert-butoxycarbonyl-N-α-methyl-glycine, N-α-tert-butoxycarbonyl-L-histidine, N-α-tert-butoxycarbonyl-D-histidine, N-α-tert-butoxycarbonyl-L-histidine methyl ester, N-α, im-di-tert-butoxycarbonyl-L-histidine, N-α-tert-butoxycarbonyl-N-π-benzyloxymethyl-L-histidine, N-tert-butoxycarbonyl-N-τ-trityl-L-histidine, N-α-tert-butoxycarbonyl-L-hydroxyproline, N-α-tert-butoxycarbonyl-trans-hydroxy-D-proline, N-α-tert-butoxycarbonyl-L-hydroxyproline-benzyl ester, N-α-tert-butoxycarbonyl-L-isoleucine methyl ester, N-α-tert-butoxycarbonyl-N-α-methyl-L-allo-isoleucine, N-α-tert-butoxycarbonyl-N-α-methyl-L-isoleucine, N-α-tert-butoxycarbonyl-N-α-methyl-D-isoleucine, N-α-tert-butoxycarbonyl-L-leucine methyl ester, N-α-tert-butoxycarbonyl-D-leucine methyl ester, N-α-tert-butoxycarbonyl-N-α-methyl-L-leucine, N-α-tert-butoxycarbonyl-N-α-methyl-D-leucine, N-α-tert-butoxycarbonyl-L-lysine, N-α-tert-butoxycarbonyl-D-lysine, N-α-tert-butoxycarbonyl-N-ε-acetyl-L-lysine, N-α, N-ε-di-tert-butoxycarbonyl-L-lysine, N-α, N-ε-di-tert-butoxycarbonyl-D-lysine, N-α-tert-butoxycarbonyl-L-methionine, N-α-tert-butoxycarbonyl-D-methionine, N-α-tert-butoxycarbonyl-DL-methionine, N-δ-tert-butoxycarbonyl-L-ornithine, N-δ-tert-butoxycarbonyl-D-ornithine, N-α, N-δ-di-tert-butoxycarbonyl-L-ornithine, N-α, N-δ-di-tert-butoxycarbonyl-D-ornithine, N-α-tert-butoxycarbonyl-L-phenylalanine, N-α-tert-butoxycarbonyl-D-phenylalanine, N-α-tert-butoxycarbonyl-DL-phenylalanine, N-α-tert-butoxycarbonyl-L-phenylalanine benzyl ester, N-α-tert-butoxycarbonyl-L-phenylalanine methyl ester, N-α-tert-butoxycarbonyl-N-α-methyl-L-phenylalanine, N-α-tert-butoxycarbonyl-L-proline, N-α-tert-butoxycarbonyl-D-proline, N-α-tert-butoxycarbonyl-L-proline methyl ester, N-α-tert-butoxycarbonyl-D-proline methyl ester, N-α-tert-butoxycarbonyl-L-serine, N-α-tert-butoxycarbonyl-D-serine, N-α-tert-butoxycarbonyl-L-serine α-benzyl ester, N-α-tert-butoxycarbonyl-L-serine α-methyl ester, N-α-tert-butoxycarbonyl-L-threonine, N-α-tert-butoxycarbonyl-D-threonine, N-α-tert-butoxycarbonyl-L-threonine methyl ester, N-α-tert-butoxycarbonyl-N-methyl-L-threonine, N-α-tert-butoxycarbonyl-O-methyl-L-threonine, N-α-tert-butoxycarbonyl-L-tryptophan, N-α-tert-butoxycarbonyl-D-tryptophan, N-α-tert-butoxycarbonyl-L-tryptophan methyl ester, N-α-tert-butoxycarbonyl-N-in-tert-butoxycarbonyl-L-tryptophan, N-α-tert-butoxycarbonyl-L-tyrosine, N-α-tert-butoxycarbonyl-D-tyrosine, N-α-tert-butoxycarbonyl-L-tyrosine benzyl ester, N-α-tert-butoxycarbonyl-L-tyrosine methyl ester, N, O-di-tert-butoxycarbonyl-L-tyrosine, N-α-tert-butoxycarbonyl-L-valine, N-α-tert-butoxycarbonyl-D-valine, N-α-tert-butoxycarbonyl-DL-valine, N-α-(9-fluorenylmethoxycarbonyl)-L-alanine, N-α-(9-fluorenylmethoxycarbonyl)-D-alanine, N-α-(9-fluorenylmethoxycarbonyl)-N-α-methyl-L-alanine, N-α-(9-fluorenylmethoxycarbonyl)-N-α-methyl-D-alanine, N-α-(9-fluorenylmethoxycarbonyl)-N-ω1, N-ω2-di-tert-butoxycarbonyl-L-arginine, N-α-(9-fluorenylmethoxycarbonyl)-N-ω1, N-ω2-di-tert-butoxycarbonyl-D-arginine, N-α-(9-fluorenylmethoxycarbonyl)-L-isoasparagine, N-α-(9-fluorenylmethoxycarbonyl)-D-isoasparagine, N-α-(9-fluorenylmethoxycarbonyl)-Nβ-4-methyltrityl-L-asparagine, N-α-(9-fluorenylmethoxycarbonyl)-N-β-4-methyltrityl-D-asparagine, N-α-(9-fluorenylmethoxycarbonyl)-L-aspartic acid, N-α-(9-fluorenylmethoxycarbonyl)-D-aspartic acid, N,N'-di-9-fluorenylmethoxycarbonyl-L-cysteine, N-α-(9-fluorenylmethoxycarbonyl)-S-ethyl-L-cysteine, N-α-(9- fluorenylmethoxycarbonyl)-S-tert-butyl-L-cysteine, N-α-(9-fluorenylmethoxycarbonyl)-L-isoglutamine, N-α-(9-fluorenylmethoxycarbonyl)-D-isoglutamine, N-α-(9-fluorenylmethoxycarbonyl)-L-isoglutamic acid, N-α-(9-fluorenylmethoxycarbonyl)-L-isoglutamic acid α-fluorenylmethyl ester, N-α-(9-fluorenylmethoxycarbonyl)-L-isoglutamic acid α-tert-butyl ester, N-α-(9-fluorenylmethoxycarbonyl)-L-glycine, N-α-(9-fluorenylmethoxycarbonyl)-N-α-methyl-glycine, N-α-(9-fluorenylmethoxycarbonyl)-L-histidine, N-α-(9-fluorenylmethoxycarbonyl)-D-histidine, N-α-(9-fluorenylmethoxycarbonyl)-N-τ-tert-butoxycarbonyl-L-histidine, N-α, N-τ-di-(9-fluorenylmethoxycarbonyl)-L-histidine, N-α-(9-fluorenylmethoxycarbonyl)-trans-4-hydroxy-L-proline, N-α-(9-fluorenylmethoxycarbonyl)-trans-4-hydroxy-D-proline, N-α-(9-fluorenylmethoxycarbonyl)-L-isoleucine, N-α-(9-fluorenylmethoxycarbonyl)-D-isoleucine, N-α-(9-fluorenylmethoxycarbonyl)-L-allo-isoleucine, N-α-(9-fluorenylmethoxycarbonyl)-L-leucine, N-α-(9-fluorenylmethoxycarbonyl)-D-leucine, N-α-(9-fluorenylmethoxycarbonyl)-N-α-methyl-L-leucine, N-α-tert-butoxycarbonyl-N-ε-(9-fluorenylmethoxycarbonyl)-L-lysine, N-α-tert-butoxycarbonyl-N-ε-(9-fluorenylmethoxycarbonyl)-D-lysine, N-α-(9-fluorenylmethoxycarbonyl)-N-ε-isopropyl-N-ε-tert-butoxycarbonyl-L-lysine, N-α-(9-fluorenylmethoxycarbonyl)-N-ε-tert-butoxycarbonyl-L-lysine, N-α-(9-fluorenylmethoxycarbonyl)-L-methionine, N-α-(9-fluorenylmethoxycarbonyl)-D-methionine, N-α-(9-fluorenylmethoxycarbonyl)-L-methionine-DL-sulfoxide, N-α-(9-fluorenylmethoxycarbonyl)-N-δ-tert-butoxycarbonyl-L-ornithine, N-α-(9-fluorenylmethoxycarbonyl)-N-δ-tert-butoxycarbonyl-D-ornithine, N-α, δ-di-(9-fluorenylmethoxycarbonyl)-L-ornithine, N-α-(9-fluorenylmethoxycarbonyl)-L-phenylalanine, N-α-(9-fluorenylmethoxycarbonyl)-D-phenylalanine, N-α-(9-fluorenylmethoxycarbonyl)-DL-phenylalanine, N-α-(9-fluorenylmethoxycarbonyl)-L-proline, N-α-(9-fluorenylmethoxycarbonyl)-D-proline, N-α-(9-fluorenylmethoxycarbonyl)-L-serine, N-α-(9-fluorenylmethoxycarbonyl)-D-serine, N-α-(9-fluorenylmethoxycarbonyl)-L-serine methyl ester, N-α-(9-fluorenylmethoxycarbonyl)-L-threonine, N-α-(9-fluorenylmethoxycarbonyl)-D-threonine, N-α-(9-fluorenylmethoxycarbonyl)-N-α-methyl-L-threonine, N-α-(9-fluorenylmethoxycarbonyl)-L-tryptophan, N-α-(9-fluorenylmethoxycarbonyl)-D-tryptophan, N-α-(9-fluorenylmethoxycarbonyl)-L-tyrosine, N-α-(9-fluorenylmethoxycarbonyl)-D-tyrosine, N-α-(9-fluorenylmethoxycarbonyl)-L-valine, and N-α-(9-fluorenylmethoxycarbonyl)-D-valine, to which the examples are not limited.

The amino acid generator preferably has large basicity for more accelerating the condensation-polymerization of the polysiloxane when the protecting group for an amino group is eliminated by heat or light and an amino group is developed. That is, preferred examples of the amino acid generator include N-α, N-ω1, N-ω2-tri-tert-butoxycarbonyl-N-methyl-L-arginine, N-α-tert-butoxycarbonyl-L-arginine, N-α-tert-butoxycarbonyl-N-ω1, N-ω2-bis-carbobenzoxy-L-arginine, N-α-tert-butoxycarbonyl-N-ω1, N-ω2-bis-carbobenzoxy-D-arginine, N-α-tert-butoxycarbonyl-L-histidine, N-α-tert-butoxycarbonyl-D-histidine, N-α-tert-butoxycarbonyl-L-histidine methyl ester, N-α, im-di-tert-butoxycarbonyl-L-histidine, N-α-tert-butoxycarbonyl-N-π-benzyloxymethyl-L-histidine, N-tert-butoxycarbonyl-N-τ-trityl-L-histidine, N-α-tert-butoxycarbonyl-L-lysine, N-α-tert-butoxycarbonyl-D-lysine, N-α-tert-butoxycarbonyl-N-α-acetyl-L-lysine, N-α, N-ε-di-tert-butoxycarbonyl-L-lysine, N-α, N-ε-di-tert-butoxycarbonyl-D-lysine, N-δ-tert-butoxycarbonyl-L-ornithine, N-δ-tert-butoxycarbonyl-D-ornithine, N-α, N-δ-di-tert-butoxycarbonyl-L-ornithine, N-α, N-δ-di-tert-butoxycarbonyl-D-ornithine, N-α-(9-fluorenylmethoxycarbonyl)-N-ω1, N-ω2-di-tert-butoxycarbonyl-L-arginine, N-α-(9-fluorenylmethoxycarbonyl)-N-ω1, N-ω2-di-tert-butoxycarbonyl-D-arginine, N-α-(9-fluorenylmethoxycarbonyl)-L-histidine, N-α-(9-fluorenylmethoxycarbonyl)-D-histidine, N-α-(9-fluorenylmethoxycarbonyl)-N-τ-tert-butoxycarbonyl-L-histidine, N-α, N-τ-di-(9-fluorenylmethoxycarbonyl)-L-histidine, N-α-tert-butoxycarbonyl-N-ε-(9-fluorenylmethoxycarbonyl)-L-lysine, N-α-tert-butoxycarbonyl-N-ε-(9-fluorenylmethoxycarbonyl)-D-lysine, N-α-(9-fluorenylmethoxycarbonyl)-N-ε-isopropyl-N-ε-tert-butoxycarbonyl-L-lysine, N-α-(9-fluorenylmethoxycarbonyl)-N-ε-tert-butoxycarbonyl-L-lysine, N-α-(9-fluorenylmethoxycarbonyl)-N-δ-tert-butoxycarbonyl-L-ornithine, N-α-(9-fluorenylmethoxycarbonyl)-N-δ-tert-butoxycarbonyl-D-ornithine, and N-α, δ-di-(9-fluorenylmethoxycarbonyl)-L-ornithine.

Because of the largest isoelectric point and large basicity, an amino acid generator in which arginine is selected as the amino acid is effective.

That is, more preferred examples of the amino acid generator include N-α, N-ω1, N-ω2-tri-tert-butoxycarbonyl-N-methyl-L-arginine, N-α-tert-butoxycarbonyl-L-arginine, N-α-tert-butoxycarbonyl-N-ω1, N-ω2-bis-carbobenzoxy-L-arginine, N-α-tert-butoxycarbonyl-N-ω1, N-ω2-bis-carbobenzoxy-D-arginine, N-α-(9-fluorenylmethoxycarbonyl)-N-ω1, N-ω2-di-tert-butoxycarbonyl-L-arginine, and N-α-(9-fluorenylmethoxycarbonyl)-N-ω1, N-ω2-di-tert-butoxycarbonyl-D-arginine.

The above amino acid generators are commercially available from, for example Watanabe Chemical Industries, Ltd. and Tokyo Chemical Industry Co., Ltd.

The present invention is also a coating film forming composition containing the component (A), the component (B), and the component (C):

Component (A): the amino acid generator,

Component (B): a hydrolyzable silane, a hydrolysis product thereof, a hydrolysis-condensation product thereof, or a mixture thereof, Component (C): a solvent.

As the component (B), there can be used at least one type of hydrolyzable silane selected from a group consisting of hydrolyzable silanes of Formula (3) and Formula (4) below, a hydrolysis product thereof, a hydrolysis-condensation product thereof, or a mixture thereof. Here, the hydrolysis product is a product in which a hydrolyzable group of $R^4$ or $R^6$ is hydrolyzed to generate a silanol group. The hydrolysis-condensation product is a product in which silanol groups in the hydrolysis product are dehydrolysis-condensed with each other to form a polysiloxane or a polyorganosiloxane, where a terminal of the hydrolysis-condensation product has a silanol group. The hydrolysis-condensation product is a polysiloxane and may be a polysiloxane containing a polyorganosiloxane moiety.

$$R^3_a Si(R^4)_{4-a} \qquad \text{Formula (3)}$$

(where $R^3$ is an alkyl group, an aryl group, a halogenated alkyl group, a halogenated aryl group, an alkenyl group, or an organic group having an epoxy group, an acryloyl group, a methacryloyl group, a mercapto group, an amino group, a carboxy group, a phosphate group, an amide group, a nitro group, an acyl group, a sulfonic group, a cyano group, or a combination thereof, where $R^3$ is bonded to a silicon atom through a Si—C bond; $R^4$ is an alkoxy group, an acyloxy group, or a halogen atom that is a hydrolyzable group; and a is an integer of 0 to 3)

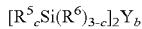  Formula (4)

(where $R^5$ is an alkyl group, an aryl group, a halogenated alkyl group, a halogenated aryl group, an alkenyl group, or an organic group having an epoxy group, an acryloyl group, a methacryloyl group, a mercapto group, an amino group, a carboxy group, a phosphate group, an amide group, a nitro group, an acyl group, a sulfonic group, a cyano group, or a combination thereof, where $R^5$ is bonded to a silicon atom through a Si—C bond; $R^6$ is an alkoxy group, an acyloxy group, or a halogen atom that is a hydrolyzable group; Y is an alkylene group or an arylene group; b is an integer of 0 or 1; and c is an integer of 0 or 1.)

Examples of the above alkyl group include $C_{1-10}$ alkyl groups such as a methyl group, an ethyl group, an n-propyl group, an isopropyl group, a cyclopropyl group, an n-butyl group, an isobutyl group, a sec-butyl group, a tert-butyl group, a cyclobutyl group, a 1-methyl-cyclopropyl group, a 2-methyl-cyclopropyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-isopropyl-cyclopropyl group, a 2-isopropyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Examples of the above aryl group include $C_{6-40}$ aryl groups such as a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

Examples of the above alkenyl group include $C_{2-10}$ alkenyl groups such as an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethyl-ethenyl group, a 1-methyl-1-propenyl group, a 1-methyl-2-propenyl group, a 1-pentenyl group, a 2-pentenyl group, a 3-pentenyl group, a 4-pentenyl group, a 1-n-propyl-ethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-isopropyl-ethenyl group, a 1,2-dimethyl-1-propenyl group, a 1,2-dimethyl-2-propenyl group, a 1-cyclopentenyl group, a 2-cyclopentenyl group, a 3-cyclopentenyl group, a 1-hexenyl group, a 2-hexenyl group, a 3-hexenyl group, a 4-hexenyl group, a 5-hexenyl group, a 1-methyl-1-pentenyl group, a 1-methyl-2-pentenyl group, a 1-methyl-3-pentenyl group, a 1-methyl-4-pentenyl group, a 1-n-butyl-ethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-sec-butyl-ethenyl group, a 1,3-dimethyl-1-butenyl group, a 1,3-dimethyl-2-butenyl group, a 1,3-dimethyl-3-butenyl group, a 1-isobutyl-ethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-isopropyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-tert-butyl-ethenyl group, a 1-methyl-1-ethyl-2-propenyl group, a 1-ethyl-2-methyl-1-propenyl group, a 1-ethyl-2-methyl-2-propenyl group, a 1-isopropyl-1-propenyl group, a 1-isopropyl-2-propenyl group, a 1-methyl-2-cyclopentenyl group, a 1-methyl-3-cyclopentenyl group, a 2-methyl-1-cyclopentenyl group, a 2-methyl-2-cyclopentenyl group, a 2-methyl-3-cyclopentenyl group, a 2-methyl-4-cyclopentenyl group, a 2-methyl-5-cyclopentenyl group, a 2-methylene-cyclopentyl group, a 3-methyl-1-cyclopentenyl group, a 3-methyl-2-cyclopentenyl group, a 3-methyl-3-cyclopentenyl group, a 3-methyl-4-cyclopentenyl group, a 3-methyl-5-cyclopentenyl group, a 3-methylene-cyclopentyl group, a 1-cyclohexenyl group, a 2-cyclohexenyl group, and a 3-cyclohexenyl group.

Examples of the above organic group having an epoxy group include a glycidoxymethyl group, a glycidoxyethyl group, a glycidoxypropyl group, a glycidoxybutyl group, and an epoxycyclohexyl group.

Examples of the above organic group having an acryloyl group include an acryloylmethyl group, an acryloylethyl group, and an acryloylpropyl group.

Examples of the above organic group having a methacryloyl group include a methacryloylmethyl group, a methacryloylethyl group, and a methacryloylpropyl group.

Examples of the above organic group having a mercapto group include an ethylmercapto group, a butylmercapto group, a hexylmercapto group, and an octylmercapto group.

Examples of the above acyl group include a formyl group, an acetyl group, a propionyl group, a butyryl group, an isobutyryl group, a valeryl group, an isovaleryl group, and a benzoyl group.

Examples of the above organic group having a cyano group include a cyanoethyl group and a cyanopropyl group.

Examples of the above alkoxy group include $C_{1-20}$ alkoxy groups having a linear, branched, or cyclic alkyl part such as a methoxy group, an ethoxy group, an n-propoxy group, an isopropoxy group, an n-butoxy group, an isobutoxy group, a sec-butoxy group, a tert-butoxy group, an n-pentoxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, an n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2-trimethyl-n-propoxy group, a 1-ethyl-1-methyl-n-propoxy group, and a 1-ethyl-2-methyl-n-propoxy group.

Examples of the above acyloxy group include $C_{2-20}$ acyloxy groups such as a methylcarbonyloxy group, an ethylcarbonyloxy group, an n-propylcarbonyloxy group, an isopropylcarbonyloxy group, an n-butylcarbonyloxy group, an isobutylcarbonyloxy group, a sec-butylcarbonyloxy group, a tert-butylcarbonyloxy group, an n-pentylcarbonyloxy group, a 1-methyl-n-butylcarbonyloxy group, a 2-methyl-n-butylcarbonyloxy group, a 3-methyl-n-butylcarbonyloxy group, a 1,1-dimethyl-n-propylcarbonyloxy group, a 1,2-dimethyl-n-propylcarbonyloxy group, a 2,2-dimethyl-n-propylcarbonyloxy group, a 1-ethyl-n-propylcarbonyloxy group, an n-hexylcarbonyloxy group, a 1-methyl-n-pentylcarbonyloxy group, a 2-methyl-n-pentylcarbonyloxy group, a 3-methyl-n-pentylcarbonyloxy group, a 4-methyl-n-pentylcarbonyloxy group, a 1,1-dimethyl-n-butylcarbonyloxy group, a 1,2-dimethyl-n-butylcarbonyloxy group, a 1,3-dimethyl-n-butylcarbonyloxy group, a 2,2-dimethyl-n-butylcarbonyloxy group, a 2,3-dimethyl-n-butylcarbonyloxy group, a 3,3-dimethyl-n-butylcarbonyloxy group, a 1-ethyl-n-butyl carbonyloxy group, a 2-ethyl-n-butylcarbonyloxy group, a 1,1,2-trimethyl-n-propylcarbonyloxy group, a 1,2,2-trimethyl-n-propylcarbonyloxy group, a 1-ethyl-1-methyl-n-propylcarbonyloxy group, a 1-ethyl-2-methyl-n-propylcarbonyloxy group, a phenylcarbonyloxy group, and a tosylcarbonyloxy group.

Examples of the halogen atom as a hydrolyzable group include a fluorine atom, a chlorine atom, a bromine atom, and an iodine atom.

Examples of the alkylene group in Formula (4) include $C_{1-10}$ alkylene groups such as a methylene group, an ethylene group, a propylene group, an isopropylene group, a butylene group, and an octylene group. Moreover, divalent organic groups derived from the above exemplified linear or branched alkyl groups may also be used as the alkylene group.

Examples of the arylene group in Formula (4) include $C_{6-20}$ arylene groups such as a phenylene group, a naphthylene group, and an anthralene group. Divalent organic groups derived from the above exemplified aryl groups may also be used as the arylene group.

Examples of the hydrolyzable silane selected from a group consisting of hydrolyzable silanes of Formula (3) include tetramethoxysilane, tetrachlorosilane, tetraacetoxysilane, tetraethoxysilane, tetra-n-propoxysilane, tetraisopropoxysilane, tetra-n-butoxysilane, tetraacetoxysilane, methyltrimethoxysilane, methyltrichlorosilane, methyltriacetoxysilane, methyltripropoxysilane, methyltriacetoxysilane, methyltributoxysilane, methyltripropoxysilane, methyltriamyloxysilane, methyltriphenoxysilane, methyltribenzyloxysilane, methyltriphenethyloxysilane, glycidoxymethyltrimethoxysilane, glycidoxymethyltriethoxysilane, α-glycidoxyethyltrimethoxysilane, α-glycidoxyethyltriethoxysilane, β-glycidoxyethyltrimethoxysilane, β-glycidoxyethyltriethoxysilane, α-glycidoxypropyltrimethoxysilane, α-glycidoxypropyltriethoxysilane, β-glycidoxypropyltrimethoxysilane, β-glycidoxypropyltriethoxysilane, γ-glycidoxypropyltrimethoxysilane, γ-glycidoxypropyltriethoxysilane, γ-glycidoxypropyltripropoxysilane, γ-glycidoxypropyltributoxysilane, γ-glycidoxypropyltriphenoxysilane, α-glycidoxybutyltrimethoxysilane, α-glycidoxybutyltriethoxysilane, β-glycidoxybutyltriethoxysilane, γ-glycidoxybutyltrimethoxysilane, γ-glycidoxybutyltriethoxysilane, δ-glycidoxybutyltrimethoxysilane, δ-glycidoxybutyltriethoxysilane, (3,4-epoxycyclohexyl)methyltrimethoxysilane, (3,4-epoxycyclohexyl)methyltriethoxysilane, β-(3,4-epoxycyclohexyl)ethyltrimethoxysilane, β-(3,4-epoxycyclohexyl)ethyltriethoxysilane, β-(3,4-epoxycyclohexyl)ethyltripropoxysilane, β-(3,4-epoxycyclohexyl)ethyltributoxysilane, β-(3,4-epoxycyclohexyl)ethyltriphenoxysilane, γ-(3,4-epoxycyclohexyl)propyltrimethoxysilane, epoxycyclohexyl)propyltriethoxysilane, γ-(3,4-epoxycyclohexyl)butyltrimethoxysilane, (3,4-epoxycyclohexyl)butyltriethoxysilane, glycidoxymethylmethyldimethoxysilane, glycidoxymethylmethyldiethoxysilane, α-glycidoxyethylmethyldimethoxysilane, glycidoxyethylmethyldiethoxysilane, β-glycidoxyethylmethyldimethoxysilane, β-glycidoxyethylethyldimethoxysilane, α-glycidoxypropylmethyldimethoxysilane, α-glycidoxypropylmethyldiethoxysilane, β-glycidoxypropylmethyldimethoxysilane, β-glycidoxypropylethyldimethoxysilane, γ-glycidoxypropylmethyldimethoxysilane, γ-glycidoxypropylmethyldiethoxysilane, γ-glycidoxypropylmethyldipropoxysilane, γ-glycidoxypropylmethyldibutoxysilane, γ-glycidoxypropylmethyldiphenoxysilane, γ-glycidoxypropylethyldimethoxysilane, γ-glycidoxypropylethyldiethoxysilane, γ-glycidoxypropylvinyldimethoxysilane, γ-glycidoxypropylvinyldiethoxysilane, ethyltrimethoxysilane, ethyltriethoxysilane, vinyltrimethoxysilane, vinyltrichlorosilane, vinyltriacetoxysilane, vinyltriethoxysilane, vinyltriacetoxysilane, phenyltrimethoxysilane, phenyltrichlorosilane, phenyltriacetoxysilane, phenyltriethoxysilane, phenyltriacetoxysilane, γ-chloropropyltrimethoxysilane, γ-chloropropyltriethoxysilane, γ-chloropropyltriacetoxysilane, 3,3,3-trifluoropropyltrimethoxysilane, γ-methacryloxypropyltrimethoxysilane, γ-mercaptopropyltrimethoxysilane, γ-mercaptopropyltriethoxysilane, γ-cyanoethyltriethoxysilane, chloromethyltrimethoxysilane, chloromethyltriethoxysilane, dimethyldimethoxysilane, phenylmethyldimethoxysilane, dimethyldiethoxysilane, phenylmethyldiethoxysilane, chloropropylmethyldimethoxysilane, γ-chloropropylmethyldiethoxysilane, dimethyldiacetoxysilane, γ-methacryloxypropylmethyldimethoxysilane, γ-methacryloxypropylmethyldiethoxysilane, γ-mercaptopropylmethyldimethoxysilane, γ-mercaptomethyldiethoxysilane, methylvinyldimethoxysilane, and methylvinyldiethoxysilane.

Examples of the hydrolyzable silane selected from a group consisting of hydrolyzable silanes of Formula (4) include methylenebistrimethoxysilane, methylenebistrichlorosilane, methylenebistriacetoxysilane, ethylenebistriethoxysilane, ethylenebistrichlorosilane, ethylenebistriacetoxysilane, propylenebistriethoxysilane, butylenebistrimethoxysilane, phenylenebistrimethoxysilane, phenylenebistriethoxysilane, phenylenebismethyldiethoxysilane, phenylenebismethyldimethoxysilane, naphthylenebistrimethoxysilane, bistrimethoxydisilane, bistriethoxydisilane, bisethyldiethoxydisilane, and bismethyldimethoxydisilane.

As the component (B), there is preferably used at least one type of hydrolyzable silane selected from a group consisting of hydrolyzable silanes of Formula (3) (where a is 0 to 2), a hydrolysis product thereof, a hydrolysis-condensation product thereof, or a mixture thereof.

As the hydrolyzable silanes of Formula (3) and Formula (4), commercially available products may be used.

A polysiloxane produced by hydrolyzing a hydrolyzable silane of Formula (3) or hydrolyzable silanes of Formula (3) and Formula (4) and by condensing the resultant hydrolysis product has a weight average molecular weight of 1,000 to 1,000,000 or 1,000 to 100,000. These molecular weights are a molecular weight obtained by GPC analysis in terms of polystyrene.

Examples of the type of a hydrolysis catalyst during the synthesis of the polysiloxane include a metal chelate compound, an organic acid, an inorganic acid, an organic base, and an inorganic base.

Examples of the metal chelate compound include: titanium chelate compounds such as triethoxy-mono(acetylacetonate)titanium, tri-n-propoxy-mono(acetylacetonate)titanium, tri-isopropoxy-mono(acetylacetonate)titanium, tri-n-butoxy-mono(acetylacetonate)titanium, tri-sec-butoxy-mono(acetylacetonate)titanium, tri-tert-butoxy-mono(acetylacetonate)titanium, diethoxy-bis(acetylacetonate)titanium, di-n-propoxy-bis(acetylacetonate)titanium, diisopropoxy-bis(acetylacetonate)titanium, di-n-butoxy-bis(acetylacetonate)titanium, di-sec-butoxy-bis(acetylacetonate)titanium, di-tert-butoxy-bis(acetylacetonate)titanium, monoethoxy-tris(acetylacetonate)titanium, mono-n-propoxy-tris(acetylacetonate)titanium, mono-isopropoxy-tris(acetylacetonate)titanium, mono-n-butoxy-tris(acetylacetonate)titanium, mono-sec-butoxy-tris(acetylacetonate)titanium, mono-tert-butoxy-tris(acetylacetonate)titanium, tetrakis(acetylacetonate)titanium, triethoxy-mono(ethylacetoacetate)titanium, tri-n-tri-isopropoxy-mono(ethylacetoacetate)titanium, tri-n-butoxy-mono(ethylacetoacetate)titanium, tri-sec-butoxy-mono(ethylacetoacetate)titanium, tri-tert-butoxy-mono(ethylacetoacetate)titanium, diethoxy-bis(ethylacetoacetate)titanium, di-n-propoxy-bis(ethylacetoacetate)titanium, di-isopropoxy-bis(ethylacetoacetate)titanium, di-n-butoxy-bis(ethylacetoacetate)titanium, di-sec-butoxy-bis(ethylacetoacetate)titanium, di-tert-butoxy-bis(ethylacetoacetate)titanium, monoethoxy-tris(ethylacetoacetate)titanium, mono-n-propoxy-tris(ethylacetoacetate)titanium, mono-isopropoxy-tris(ethylacetoacetate)titanium, mono-n-butoxy-tris(ethylacetoacetate)titanium, mono-sec-butoxy-tris(ethylacetoacetate)titanium, mono-tert-butoxy-tris(ethylacetoacetate)titanium, tetrakis(ethylacetoacetate)titanium, mono(acetylacetonate)tris(ethylacetoacetate)titanium, bis(acetylacetonate)bis(ethylacetoacetate)titanium, and tris(acetylacetonate)mono(ethylacetoacetate)titanium; zirconium chelate compounds such as triethoxy-mono(acetylacetonate)zirconium, tri-n-propoxy-mono(acetylacetonate)zirconium, triisopropoxy-mono(acetylacetonate)zirconium, tri-n-butoxy-mono(acetylacetonate)zirconium, tri-sec-butoxy-mono(acetylacetonate)zirconium, tri-tert-butoxy-mono(acetylacetonate)zirconium, diethoxy-bis(acetylacetonate)zirconium, di-n-propoxy-bis(acetylacetonate)zirconium, di-isopropoxy-bis(acetylacetonate)zirconium, di-n-butoxy-bis(acetylacetonate)zirconium, di-sec-butoxy-bis(acetylacetonate)zirconium, di-tert-butoxy-bis(acetylacetonate)zirconium, monoethoxy-tris(acetylacetonate)zirconium, mono-n-propoxy-tris(acetylacetonate)zirconium, monoisopropoxy-tris(acetylacetonate)zirconium, mono-n-butoxy-tris(acetylacetonate)zirconium, mono-sec-butoxy-tris(acetylacetonate)zirconium, mono-tert-butoxy-tris(acetylacetonate)zirconium, tetrakis(acetylacetonate)zirconium, triethoxy-mono(ethylacetoacetate)zirconium, tri-n-propoxy-mono(ethylacetoacetate)zirconium, tri-isopropoxy-mono(ethylacetoacetate)zirconium, tri-n-butoxy-mono(ethylacetoacetate)zirconium, tri-sec-butoxy-mono(ethylacetoacetate)zirconium, tri-tert-butoxy-mono(ethylacetoacetate)zirconium, diethoxy-bis(ethylacetoacetate)zirconium, di-n-propoxy-bis(ethylacetoacetate)zirconium, di-isopropoxy-bis(ethylacetoacetate)zirconium, di-n-butoxy-bis(ethylacetoacetate)zirconium, di-sec-butoxy-bis(ethylacetoacetate)zirconium, di-tert-butoxy-bis(ethylacetoacetate)zirconium, monoethoxy-tris(ethylacetoacetate)zirconium, mono-n-propoxy-tris(ethylacetoacetate)zirconium, mono-isopropoxy-tris(ethylacetoacetate)zirconium, mono-n-butoxy-tris(ethylacetoacetate)zirconium, mono-sec-butoxy-tris(ethylacetoacetate)zirconium, mono-tert-butoxy-tris(ethylacetoacetate)zirconium, tetrakis(ethylacetoacetate)zirconium, mono(acetylacetonate)tris(ethylacetoacetate)zirconium, bis(acetylacetonate)bis(ethylacetoacetate)zirconium, and tris(acetylacetonate)mono(ethylacetoacetate)zirconium; and aluminum chelate compounds such as tris(acetylacetonate)aluminum and tris(ethylacetoacetate)aluminum.

Examples of the organic acid include acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, and tartaric acid.

Examples of the inorganic acid include hydrochloric acid, nitric acid, sulfuric acid, hydrofluoric acid, and phosphoric acid.

Examples of the organic base include pyridine, pyrrole, piperazine, pyrrolidine, piperidine, picoline, trimethylamine, triethylamine, monoethanolamine, diethanolamine, dimethylmonoethanolamine, monomethyldiethanolamine, triethanolamine, diazabicyclo-octane, diazabicyclo-nonane, diazabicyclo-undecene, tetramethylammoniumhydroxide, and 1,8-diazabicyclo[5,4,0]-7-undecene.

Examples of the inorganic base include ammonia, sodium hydroxide, potassium hydroxide, barium hydroxide, and calcium hydroxide.

Among these hydrolysis catalysts, metal chelate compounds, organic acids, and inorganic acids are preferred and these catalysts may be used individually or in combination of two or more types thereof.

For hydrolyzing an alkoxysilyl group, an acyloxysilyl group, or a halogenated silyl group, water is used in an amount of 0.1 to 100 mol, or 0.1 to 10 mol, or 1 to 5 mol, or 2 to 3.5 mol, relative to 1 mol of the hydrolyzable group.

The hydrolysis catalyst may be used in an amount of 0.0001 to 10 mol, preferably 0.001 to 2 mol, relative to 1 mol of the hydrolyzable group.

The temperature for a reaction in which the hydrolyzable silane is hydrolyzed and the resultant hydrolysis product is condensed is usually in a range of from 20° C. (room temperature) to a reflux temperature of a solvent used for the hydrolysis under normal pressure.

The hydrolysis may be performed as a perfect hydrolysis or a partial hydrolysis. That is, the hydrolysis product or a monomer may remain in the hydrolysis-condensation product.

The method for obtaining the polysiloxane is not particularly limited. However, examples thereof include a method of heating a mixture of a silicon compound, a solvent, and oxalic acid. More specifically, the method is a method in which oxalic acid is added to an alcohol beforehand to prepare an alcohol solution of oxalic acid and the solution is mixed with a silicon compound to heat the resultant mixture. At this time, the amount of oxalic acid is generally 0.2 to 2 mol, relative to 1 mol of all alkoxy groups contained in the silicon compound. Heating in this method may be performed at 50 to 180° C. of the temperature of the reaction mixture, preferably for, for example several ten minutes to dozens of hours under reflux in a closed vessel for preventing evaporation or volatilization of the reaction mixture. The process order of the polysiloxane synthesis may be either an order that a mixture of a solvent and oxalic acid is added to a silicon compound to subject the resultant mixture to the reaction, or an order that a silicon compound is added to a mixture of a solvent and oxalic acid to subject the resultant mixture to the reaction.

The reaction for the synthesis of the polysiloxane may be effected at 0 to 50° C. of the reaction temperature for 24 to 2,000 hours for the purpose of stably synthesizing a homogeneous polymer.

Examples of the organic solvent used for the hydrolysis include: aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; aromatic hydrocarbon solvents such as benzene, toluene, xylene, ethylbenzene, trimethylbenzene, methylethylbenzene, n-propylbenzene, isopropylbenzene, diethylbenzene, isobutylbenzene, triethylbenzene, di-isopropylbenzene, n-amylnaphthalene, and trimethylbenzene; monoalcohol solvents such as methanol, ethanol, n-propanol, isopropanol, n-butanol, isobutanol, sec-butanol, tert-butanol, n-pentanol, isopentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenylmethylcarbinol, diacetone alcohol, and cresol; polyhydric alcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerin; ketone solvents such as acetone, methyl ethyl ketone, methyl n-propyl ketone, methyl n-butyl ketone, diethyl ketone, methyl isobutyl ketone, methyl n-pentyl ketone, ethyl n-butyl ketone, methyl n-hexyl ketone, di-isobutyl ketone, trimethylnonanone, cyclohexanone, methylcyclohexanone, 2,4-pentanedione, acetonylacetone, diacetone alcohol, acetophenone, and fenchone; ether solvents such as ethyl ether, isopropyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethyleneglycol monomethyl ether acetate, ethyleneglycol monoethyl ether acetate, diethyleneglycol monomethyl ether acetate, diethyleneglycol monoethyl ether acetate, diethyleneglycol mono-n-butyl ether acetate, propyleneglycol monomethyl ether acetate, propyleneglycol monoethyl ether acetate, propyleneglycol monopropyl ether acetate, propyleneglycol monobutyl ether acetate, dipropyleneglycol monomethyl ether acetate, dipropyleneglycol monoethyl ether acetate, glycol diacetate, methoxytriglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethylsulfoxide, sulfolan, and 1,3-propane sultone. These organic solvents may be used individually or in combination of two or more types thereof.

When the organic solvent is subjected to a condensation-polymerization reaction with a hydrolysis product of a hydrolyzable silane, an alcohol is generated, so that as the organic solvent, there are generally used alcohols and organic solvents having advantageous compatibility with alcohols. Particularly preferred specific examples of such an organic solvent include methanol, ethanol, propanol, isopropanol, n-butanol, ethylene glycol monomethyl ether, ethylene glycol monoethyl ether, diethylene glycol monomethyl ether, diethylene glycol monoethyl ether, n-propyl acetate, ethyl lactate, methyl ethyl ketone, propylene glycol monomethyl ether, propylene glycol monomethyl ether acetate, propylene glycol propyl ether, and cyclohexanone.

By hydrolyzing a hydrolyzable silane in a solvent and by subjecting the resultant hydrolysis product to a condensation reaction, a condensation product (polysiloxane) is obtained. Then, the condensation product is obtained as a polysiloxane vanish in which the condensation product is dissolved in a hydrolysis-solvent.

The obtained polysiloxane vanish may be solvent-exchanged. More specifically, in the case where as the solvent for the hydrolysis and the condensation (solvent for the synthesis), ethanol is selected, after the polysiloxane is obtained in ethanol, a solvent for exchange in the same amount as that of the solvent for the synthesis may be added to the polysiloxane vanish and the resultant mixture may be subjected to azeotropy using an evaporator to distil off the ethanol. The solvent for the synthesis during the solvent-exchange is distilled off by azeotropy, so that the solvent for the synthesis preferably has a boiling point lower than that of the solvent for exchange. Examples of the solvent for the hydrolysis and the condensation include methanol, ethanol, and isopropanol, and examples of the solvent for exchange include propylene glycol monomethyl ether, propylene glycol monomethyl ether acetate, and cyclohexanone.

The solvent used for the dilution or the solvent-exchange of the polysiloxane vanish may be the same as or different from a solvent used for the hydrolysis and the condensation-polymerization of the hydrolyzable silane. The solvent is not particularly limited so long as the solvent does not impair the compatibility with the polysiloxane or the amino acid generator and the solvent may be optionally selected individually or in combination of a plurality of types thereof to be used.

Examples of such a solvent as the component (C) include toluene, p-xylene, o-xylene, styrene, ethylene glycol dimethyl ether, propylene glycol monomethyl ether, ethylene glycol monomethyl ether, propylene glycol, propylene glycol monoethyl ether, ethylene glycol monoethyl ether, ethylene glycol monoisopropyl ether, ethylene glycol methyl ether acetate, propylene glycol monomethyl ether acetate, ethylene glycol ethyl ether acetate, diethylene glycol dimethyl ether, propylene glycol monobutyl ether, ethylene glycol monobutyl ether, diethylene glycol diethyl ether, dipropylene glycol monomethyl ether, diethylene glycol monomethyl ether, dipropylene glycol monoethyl ether, diethylene glycol monoethyl ether, triethylene glycol dimethyl ether, diethylene glycol monoethyl ether acetate, diethylene glycol, 1-octanol, ethylene glycol, hexylene glycol, trimethylene glycol, 1-methoxy-2-butanol, cyclohexanol, diacetone alcohol, furfuryl alcohol, tetrahydrofurfuryl alcohol, propylene glycol, benzyl alcohol, 1,3-butanediol, 1,4-butanediol, 2,3-butanediol, γ-butyrolactone, acetone, methyl ethyl ketone, methyl isopropyl ketone, di-ethyl ketone, methyl isobutyl ketone, methyl n-butyl ketone, cyclohexanone, ethyl acetate, isopropyl ketone acetate, n-propyl acetate, isobutyl acetate, n-butyl acetate, methanol, ethanol, isopropanol, tert-butanol, allyl alcohol, n-propanol, 2-methyl-2-butanol, isobutanol, n-butanol, 2-methyl-1-butanol, 1-pentanol, 2-methyl-1-pentanol, 2-ethylhexanol, 1-octanol, ethylene glycol, hexylene glycol, trimethylene glycol, 1-methoxy-2-butanol, diacetone alcohol, furfuryl alcohol, tetrahydrofurfuryl alcohol, propylene glycol, benzyl alcohol, isopropyl ether, 1,4-dioxane, N,N-dimethylformamide, N,N-dimethylacetamide, N-methylpyrrolidone, 1,3-dimethyl-2-imidazolidinone, dimethylsulfoxide, and N-cyclohexyl-2-pyrrolidinone.

Among the above-exemplified solvents, from the viewpoint of the preservation stability and compatibility with an amino acid generator of the polysiloxane vanish, more preferred examples of the solvent include methanol, ethanol, isopropanol, butanol, diacetone alcohol, acetone, methyl ethyl ketone, methyl isobutyl ketone, ethylene glycol, propylene glycol, hexylene glycol, methyl cellosolve, ethyl cellosolve, butyl cellosolve, ethyl carbitol, butyl carbitol, diethylene glycol monomethyl ether, propylene glycol monomethyl ether, propylene glycol monomethyl ether acetate, propylene glycol monobutyl ether, cyclohexanone, methyl acetic acid ester, ethyl acetic acid ester, and ethyl lactic acid ester.

The amount of the amino acid generator (thermo amino acid generator) to be added to the polysiloxane vanish (that is, polysiloxane+solvent) is not particularly limited. However, from the viewpoint of the solubility and the preservation stability, it is 0.1 to 50 phr, preferably 0.5 to 10 phr. phr is expressed in the part by mass of the added component (thereto amino acid generator) relative to 100 parts by mass of the polysiloxane. However, when the polysiloxane contains a polyorganosiloxane, from the easiness of the measurement, the amount of the added component may also be expressed in the $SiO_2$ solid content, and in this case, the amount of the added component is preferably 0.1 to 50 parts by mass, more preferably 0.5 to 10 parts by mass, relative to 100 parts by mass of the $SiO_2$ solid content in the polysiloxane.

The amount of the amino acid generator (photo amino acid generator) to be added to the polysiloxane vanish (that is, polysiloxane+solvent) is not particularly limited. However, from the viewpoint of the solubility and the preservation stability, it is 0.1 to 50 phr, preferably 2.5 to 10 phr. When the polysiloxane contains a polyorganosiloxane, from the same viewpoint as described above, the amount of the added component is preferably 0.1 to 50 parts by mass, more preferably 2.5 to 10 parts by mass, relative to 100 parts by mass of the $SiO_2$ solid content in the polysiloxane.

The polysiloxane vanish containing an amino acid generator is adjusted at pH or pKa of preferably 3 to 7, more preferably 3 to 5.

The preparation method of the coating film forming composition of the present invention is not particularly limited so long as the composition is in a state in which the polysiloxane and the amino acid generator are homogeneously mixed. Usually, the polysiloxane is obtained by a condensation-polymerization in a solvent, so that the coating film forming composition is obtained in a state of polysiloxane vanish in which the polysiloxane is dissolved in a solvent. Therefore, a method of using the obtained polysiloxane vanish as it is and mixing the polysiloxane vanish with an amino acid generator is convenient. If necessary, the polysiloxane vanish may be condensed, diluted with a solvent, or solvent-exchanged to be mixed with an amino acid generator. Further, after the polysiloxane vanish is mixed with an amino acid generator, a solvent may be added to the resultant mixture.

At this time, the coating film forming composition has a $SiO_2$ solid content-converted concentration of preferably 0.1 to 30% by mass. When the $SiO_2$ solid content-converted concentration is lower than 0.5% by mass, at one application of the composition, a desired film thickness is difficult to be obtained. On the contrary, when the $SiO_2$ solid content-converted concentration is higher than 30% by mass, the preservation stability of the solution may be impaired.

Accordingly, the $SiO_2$ solid content-converted concentration is more preferably in a range of 0.5 to 15% by mass.

The coating film forming composition of the present invention may contain besides the component (A), the component (B), and the component (C), further a crosslinkable compound as the component (D).

The component (D) is a crosslinkable compound having in the molecule thereof, at least two functional groups of Formula (D-1):

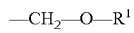  Formula (D-1)

(where $R^1$ is a hydrogen atom or a $C_{1-10}$ alkyl group).

As the component (D), there can be used a crosslinkable compound of Formula (D-2):

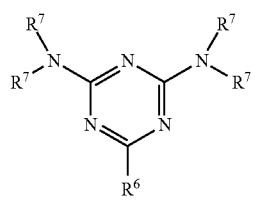  Formula (D-2)

[where $R^6$ is a hydrogen atom, a $C_{1-10}$ alkyl group, an aryl group, an aralkyl group, an alkenyl group, or a functional group of Formula (D-3):

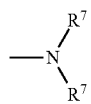  Formula (D-3)

{where $R^7$ is a hydrogen atom or a functional group of Formula (D-1)}; and $R^7$ is a hydrogen atom or a functional group of Formula (D-1), where the crosslinkable compound of Formula (D-2) has in the molecule thereof, two to six functional groups of Formula (D-1)]
or a crosslinkable compound of Formula (D-4):

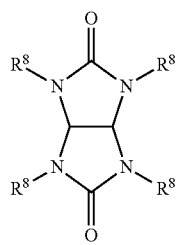  Formula (D-4)

{where $R^8$ is a hydrogen atom or a functional group of Formula (D-1), where the crosslinkable compound of Formula (D-4) has in the molecule thereof, two to four functional groups of Formula (D-1)}.

As the alkyl group, aryl group, and alkenyl group, there can be used the above-exemplified alkyl groups, aryl groups, and alkenyl groups. Examples of the aralkyl group include functional groups in which the above alkyl group is substituted with an aryl group, such as a benzyl group and a phenethyl group.

As the alkyl group in Formula (D-1), an alkyl group exemplified by the above alkyl groups can be used. A methyl group, an ethyl group, and a propyl group are particularly preferred.

Further, the functional group of Formula (D-1) is a hydroxymethyl group or an alkoxymethyl group and a nitrogen-containing compound having at least two amino groups substituted with such a functional group is preferred.

Examples of the nitrogen-containing compound include melamine and melamine derivatives, urea, guanamine, acetoguanamine, benzoguanamine and benzoguanamine derivatives, glycoluril, succinylamide, and ethylene urea in which a hydrogen atom of the amino group is substituted with a methylol group, an alkoxymethyl group, or both of them.

These nitrogen-containing compounds can be obtained by reacting, for example melamine, urea, guanamine, acetoguanamine, benzoguanamine, glycoluril, succinylamide, ethylene urea, or the like with formalin in boiling water to methylolate these compounds, or by further reacting the resultant methylol with a lower alcohol, specifically methanol, ethanol, n-propanol, isopropanol, n-butanol, or isobutanol to alkoxylate the methylol.

A triazine compound that is a melamine derivative and a triazine compound that is a benzoguanamine derivative are preferred. A triazine compound substituted with a methoxymethyl group is particularly preferred. The melamine derivative and the benzoguanamine derivative may exist as a dimer or a trimer. Then, more preferred is a triazine compound having methylol groups or alkoxymethyl groups in an average number of 3 or more and 6 or less per one triazine ring. Examples of such a triazine compound include compounds of Formula (D-2). The most representative compound of Formula (D-2) is a compound of Formula:

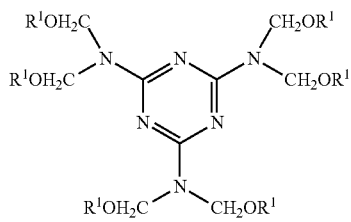

(where $R^1$ is a hydrogen atom or a $C_{1-10}$ alkyl group).

Examples of the melamine derivative or the benzoguanamine derivative include MX-750 in which one triazine ring is substituted with methoxymethyl groups in an average number of 3.7 and MW-30 in which one triazine ring is substituted with methoxymethyl groups in an average number of 5.8 (both are trade names for commercially available products from Sanwa Chemical Co., Ltd.), methoxymethylated melamine such as CYMEL 300, 301, 303, 350, 370, 771, 325, 327, 703, 712, hexamethoxymethylated melamine such as CYMEL 385, methoxymethylated butoxymethylated melamine such as CYMEL 235, 236, 238, 212, 253, 254, butoxymethylated melamine such as MYCOAT 506, 508 (to here, trade names for commercially available products from Mitsui Cytec Ltd.), carboxy group-containing methoxymethylated isobutoxymethylated melamine such as CYMEL 1141, methoxymethylated ethoxymethylated benzoguanamine such as CYMEL 1123, methoxymethylated butoxymethylated benzoguanamine such as CYMEL 1123-10, butoxymethylated benzoguanamine such as CYMEL 1128, and carboxy group-containing methoxymethylated ethoxymethylated benzoguanamine such as CYMEL 1125-80 (to here, trade names for commercially available products from Mitsui Cyanamide Co., Ltd.).

A glycoluril derivative in which a hydrogen atom of an amino group is substituted with a methylol group, an alkoxymethyl group, or both of them, particularly a glycoluril in which a hydrogen atom of an amino group is substituted with a methoxymethyl group, is preferred and a glycoluril derivative having in the molecule thereof, two or more and four or less of methoxymethyl groups is preferred. Examples of such a glycoluril derivative include compounds of Formula (D-4).

The most representative compound of Formula (D-4) is a compound of Formula:

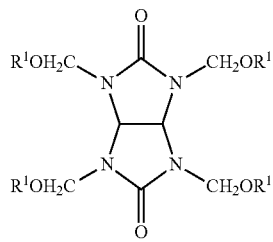

(where $R^1$ is a hydrogen atom or a $C_{1-10}$ alkyl group).

Examples of the above glycoluril include butoxymethylated glycoluril such as CYMEL 1170, methylolated glycoluril such as CYMEL 1172, and methoxymethylated glycoluril such as POWDERLINK 1174 (to here, trade names for commercially available products from Mitsui Cytec Ltd.).

Examples of the above crosslinkable compound include polymers produced using an acrylamide compound or a methacrylamide compound which are substituted with a hydroxymethyl group or an alkoxymethyl group such as N-hydroxymethylacrylamide, N-methoxymethylmethacrylamide, N-ethoxymethylacrylamide, and N-butoxymethylmethacrylamide.

Examples of such a polymer include poly(N-butoxymethylacrylamide), a copolymer of N-butoxymethylacrylamide with styrene, a copolymer of N-hydroxymethylmethacrylamide with methylmethacrylate, a copolymer of N-ethoxymethylmethacrylamide with benzylmethacrylate, and a copolymer of N-butoxymethylacrylamide, benzylmethacrylate, and 2-hydroxypropylmethacrylate.

Such a polymer has a weight average molecular weight of, for example 1,000 to 500,000, or 2,000 to 200,000, or 3,000 to 150,000, or 3,000 to 50,000.

The present invention is a coating film forming composition in which the component (A), the component (B), and the component (D) are dissolved in the component (C).

Accordingly, in the present invention, a solvent used for the production of a hydrolyzable silane, a hydrolysis product thereof, a hydrolysis-condensation product thereof, or a mixture thereof as the component (B) as it is can be used as the solvent of the component (C). That is, examples of the production method of the coating film forming composition (polysiloxane composition) include a production method by adding the component (A) and the component (D) to the polysiloxane vanish (component (B)+component (C)).

In the present invention, the coating film forming composition in which the component (B) and the component (D) are dissolved in the composition (C) can enhance the filling property thereof in a via.

Accordingly, examples of the production method of the coating film forming composition include a production method by adding the component (D) to the polysiloxane vanish (component (B)+component (C)).

A crosslinkable compound as the component (D) may be added to the polysiloxane vanish (component (B)+component (C)) in a ratio of the crosslinkable compound relative to the polysiloxane of 5 to 20 phr. phr is expressed in parts by mass of the added component (crosslinkable compound) relative to 100 parts by mass of the polysiloxane. When the polysiloxane contains a polyorganosiloxane, from the easiness of the measurement, the amount of the added component may also be expressed in the $SiO_2$ solid content, and in this case, the polysiloxane may contain the polyorganosiloxane in a content of 5 to 20 parts by mass, relative to 100 parts by mass of the $SiO_2$ solid content in the polysiloxane.

The coating film forming composition of the present invention may contain besides the amino acid generator, the polysiloxane, and the solvent, other components such as a leveling agent and a surfactant so long as the effect of the present invention is not impaired.

Examples of the surfactant include: nonionic surfactants, for example polyoxyethylene alkyl ethers such as polyoxyethylene lauryl ether, polyoxyethylene stearyl ether, polyoxyethylene cetyl ether, and polyoxyethylene oleyl ether, polyoxyethylene alkylallyl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate, and sorbitan tristearate, polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorinated surfactants, for example EFTOP EF301, EF303, and EF352 (trade name; manufactured by Tohkem Products Corporation), MEGAFAC F171, F173, R-08, and R-30 (trade name; manufactured by Dainippon Ink & Chemicals Inc.), Fluorad FC430 and FC431 (trade name; manufactured by Sumitomo 3M Limited), AsahiGuard AG710 and Surflon S-382, SC101, SC102, SC103, SC104, SC105, and SC106 (trade name; manufactured by Asahi Glass Co., Ltd.); and Organosiloxane polymer KP341 (manufactured by Shin-Etsu Chemical Co., Ltd.).

These surfactants may be used individually or in combination of two or more types thereof.

When the surfactant is used, the content thereof is 0.0001 to 5 parts by mass, or 0.001 to 1 part by mass, or 0.01 to 0.5 parts by mass, relative to 100 parts by mass of the condensation product (polysiloxane).

The method of mixing the above other components is not particularly limited and examples of the method include: a method of adding the amino acid generator and simultaneously the other components to the polysiloxane vanish; and a method of mixing the polysiloxane vanish with the amino acid generator and mixing the resultant mixture with the other components.

[Formation of Coating Film]

By coating a substrate with the coating film forming composition of the present invention and by thermocuring or photocuring the composition, a desired coating film can be obtained. As the coating method, a publicly known or well-known method can be adopted. Examples of the coating method include a spin coating method, a dip coating method, a flow coating method, an inkjet method, a spray coating method, a bar coating method, a gravure coating method, a roll coating method, a transferring printing method, a brush coating method, a blade coating method, and an air knife coating method. At this time, examples of the used substrate include substrates containing silicon, indium tin oxide (ITO), indium zinc oxide (IZO), plastic, glass, ceramic, and the like.

The baking equipment used for the thermocuring is not particularly limited and the composition may be baked using, for example a hot plate, an oven, and a furnace in an appropriate atmosphere such as air, an inactive gas such as nitrogen, and vacuum. By such a thermocuring, there can be obtained a coating film having a homogeneous film-formed surface.

The baking temperature for the purpose of evaporating the solvent is not particularly limited, and baking can be performed, for example at 40 to 200° C. The baking temperature for the purpose of accelerating the condensation-polymerization of the polysiloxane by heat is not particularly limited, and baking can be performed at 200 to 400° C. In these cases, for developing more highly homogeneous film formation property and progressing the reaction on the substrate, the temperature change may be divided into two or more stages.

The baking temperature and the baking time may be selected as conditions suitable for a process of an objective electronic device and there may be selected baking conditions under which the physical property values of the polysiloxane coating film meet required properties of the electronic device.

The exposure apparatus used for the photocuring is not particularly limited and the exposure may be performed, for example using a UV curing apparatus in an appropriate atmosphere such as air, an inactive gas such as nitrogen, and vacuum. Corresponding to the process of the device, there may also be performed an exposure process having two or more stages.

The exposure amount may be selected as a condition suitable for a process of an objective electronic device and there may be selected an exposure condition under which the physical property values of the polysiloxane coating film meet required properties of the electronic device. The exposure amount may be used, for example in a range of 10 mJ/cm$^2$ to 10 J/cm$^2$, preferably 500 mJ/cm$^2$ to 10 J/cm$^2$ (converted into energy at 250 nm).

For the purpose of enhancing film formation property after exposure or of further reducing remaining Si—OH bonds, the baking process may be added.

The baking equipment is not particularly limited and the composition may be baked using, for example a hot plate, an oven, and a furnace in an appropriate atmosphere such as air, an inactive gas such as nitrogen, and vacuum. By such a baking, there can be obtained a coating film having a homogeneous film-formed surface.

The baking temperature for the purpose of evaporating the solvent is not particularly limited. However, baking can be performed, for example at 40 to 150° C.

The baking temperature and the baking time may be selected as conditions suitable for a process of an objective electronic device and there may be selected drying conditions under which the physical property values of the polysiloxane coating film meet required properties of the electronic device.

The thus obtained coating film limited from the coating film forming composition containing the amino acid generator of the present invention has advantageous preservation stability of a polysiloxane vanish, can develop an effect of accelerating the condensation-polymerization of remaining Si—OH bonds, and can be formed on an arbitral substrate. The coating film is suitable for a gap-filling planarizing material on a photodiode, a planarizing material on a color filter, or a planarizing or conformal material on a microlens, which are for an electronic device, particularly a solid state imaging device.

In the coating film forming composition of the present invention, the polysiloxane vanish uses as a component for accelerating the condensation-polymerization of the Si—OH bond, an amino acid generator that is acidic in the polysiloxane vanish and has a function of generating an amino acid exhibiting basicity higher than that before heating the composition or before irradiating the composition with light (before exposure of the composition) when the amino acid generator is heated or irradiated with light (exposed to light) and a protecting group for the amino group is eliminated, so that the polysiloxane vanish in a state of containing an amino acid generator inhibits the condensation-polymerization and has advantageous preservation stability and when the polysiloxane vanish is applied on a base material and is subjected to a thermocuring or photocuring, there is generated an amino acid accelerating a condensation-polymerization (dehydration-condensation) between silanol groups of the polysiloxane.

When the polysiloxane vanish of the present invention is formed into a coating film and is baked or irradiated with light (exposed to light), the property of the amino acid generator is changed to a basicity accelerating the condensation-polymerization of the polysiloxane, so that even when thereafter, a baking stage is performed, the baking time can be shortened and the baking temperature can be lowered.

EXAMPLES

Hereinafter, the present invention will be further described in more detail referring to Examples and Comparative Examples, which should not be construed as limiting the scope of the present invention. Various measuring equipments used in Examples are as follows.

IR absorption spectrum (hereinafter, abbreviated as "FT-IR") measurement was performed using an IR absorption spectrum measuring apparatus (trade name: Nexus 670; manufactured by Nicolet Japan Co., Ltd.).

The molecular weight measurement (hereinafter, abbreviated as "GPC") of a polymer was performed using a molecular weight measuring apparatus (trade name: Shodex GPC-104/101 system; manufactured by Showa Denko K.K.).

The gas chromatography measurement (hereinafter, abbreviated as "GC") was performed using a gas chromatography apparatus (trade name: Shimadzu GC-14B; manufactured by Shimadzu Corporation) under the following conditions.
Column: capillary column CBP1-W25-100 (25 mm×0.53 mmφ×1 µm)
Column temperature: the column temperature was elevated from an initiation temperature of 50° C. at 15° C./min to an attained temperature of 290° C. (3 minutes).
Sample injected amount: 1 µL, Injection temperature: 240° C., Detector temperature: 290° C.,
Carrier gas: nitrogen (flow rate: 30 mL/min), Detecting method: an FID method.

The evaluation of filling property in a via substrate was performed using FE-SEM (trade name: JSM-7400F; manufactured by JEOL Ltd.; hereinafter, abbreviated as "SEM").

Synthesis of Polysiloxane

Synthesis Example 1

Synthesis of Polysiloxane Using TEOS

The inside of a four-neck reaction flask equipped with a reflux tube was nitrogen-purged and into the flask, 0.36 g of oxalic acid (4 mmol, 0.01 equivalent relative to all hydrolyzable silanes), 94.84 g of dehydrated ethanol, and 28.80 g of pure water (1.6 mol) were charged. The resultant mixture was stirred at room temperature for 30 minutes to completely dissolve the oxalic acid. Next, the ethanol solution of oxalic acid was heated in an oil bath while stirring the solution and the reflux was confirmed. Then, into the solution, 83.20 g of tetraethoxysilane (0.4 mol, hereinafter abbreviated as "TEOS") was dropped using an inner pressure equilibrium-type dropping funnel at a constant dropping rate over 20 minutes. After the dropping, the reaction was effected under reflux for 2 hours. After the completion of the reaction, the oil bath was removed and the reaction mixture was left to be cooled down to 23° C. to obtain a polysiloxane vanish (hereinafter, abbreviated as "PSV 1").

The PSV 1 contained ethanol as the solvent, had a SiO$_2$ solid content-converted concentration of 12% by mass, and had molecular weights of Mw: 2,500 and Mn: 1,700 measured by GPC measurement. The PSV 1 was measured by GC and as the result, there was not detected an alkoxysilane monomer.

Synthesis Example 2

Synthesis of Polysiloxane by Copolymerizing TEOS with MTES

The inside of a four-neck reaction flask equipped with a reflux tube was nitrogen-purged and into the flask, 0.36 g of oxalic acid (4 mmol, 0.01 equivalent relative to all hydrolyzable silanes), 100.78 g of dehydrated ethanol, and 28.80 g of pure water (1.6 mol) were charged. The resultant mixture was stirred at room temperature for 30 minutes to completely dissolve the oxalic acid. Next, the ethanol solution of oxalic acid was heated in an oil bath while stirring the solution and the reflux was confirmed. Then, into the solution, a solution mixture of 41.60 g of TEOS (0.2 mol) and 35.66 g of methyltriethoxysilane (0.2 mol, hereinafter abbreviated as "MTES") was dropped using an inner pressure equilibrium-type dropping funnel at a constant dropping rate over 20 minutes. After the dropping, the reaction was effected under reflux for 2 hours. After the completion of the reaction, the oil bath was removed and the reaction mixture was left to be cooled down to 23° C. to obtain a polysiloxane vanish (hereinafter, abbreviated as "PSV 2").

The PSV 2 contained ethanol as the solvent, had a SiO$_2$ solid content-converted concentration of 12% by mass, and had molecular weights of Mw: 2,100 and Mn: 1,700 measured by GPC measurement. The PSV 2 was measured by GC and as the result, there was not detected an alkoxysilane monomer.

Synthesis Example 3

Synthesis of Polysiloxane by Copolymerizing TEOS, MTES, and DMDES

The inside of a four-neck reaction flask equipped with a reflux tube was nitrogen-purged and into the flask, 0.36 g of oxalic acid (4 mmol, 0.01 equivalent relative to all hydrolyzable silanes), 102.58 g of dehydrated ethanol, and 28.80 g of pure water (1.6 mol) were charged. The resultant mixture was stirred at room temperature for 30 minutes to completely dissolve the oxalic acid. Next, the ethanol solution of oxalic acid was heated in an oil bath while stirring the solution and the reflux was confirmed. Then, into the solution, a solution mixture of 41.60 g of TEOS (0.2 mol), 24.96 g of MTES (0.14 mol), and 8.90 g of dimethyldiethoxysilane (0.06 mol, hereinafter abbreviated as "DMDES") was dropped using an inner pressure equilibrium-type dropping funnel at a constant dropping rate over 20 minutes. After the dropping, the reaction was effected under reflux for 2 hours. After the completion of the reaction, the oil bath was removed and the reaction mixture was left to be cooled down to 23° C. to obtain a polysiloxane vanish (hereinafter, abbreviated as "PSV 3").

The PSV 3 contained ethanol as the solvent, had a SiO$_2$ solid content-converted concentration of 12% by mass, and had molecular weights of Mw: 2,200 and Mn: 1,700 measured by GPC measurement. The PSV 3 was measured by GC and as the result, there was not detected an alkoxysilane monomer.

Synthesis Example 4

Synthesis of Polysiloxane Using MTES

The inside of a four-neck reaction flask equipped with a reflux tube was nitrogen-purged and into the flask, 0.36 g of oxalic acid (4 mmol, 0.01 equivalent relative to all hydrolyzable silanes), 106.72 g of dehydrated ethanol, and 28.80 g of pure water (1.6 mol) were charged. The resultant mixture was stirred at room temperature for 30 minutes to completely dissolve the oxalic acid. Next, the ethanol solution of oxalic acid was heated in an oil bath while stirring the solution and the reflux was confirmed. Then, into the solution, 71.32 g of MTES (0.4 mol) was dropped using an inner pressure equilibrium-type dropping funnel at a constant dropping rate over 20 minutes. After the dropping, the reaction was effected under reflux for 2 hours. After the completion of the reaction, the oil bath was removed and the reaction mixture was left to be cooled down to 23° C. to obtain a polysiloxane vanish (hereinafter, abbreviated as "PSV 4").

The PSV 4 contained ethanol as the solvent, had a SiO$_2$ solid content-converted concentration of 12% by mass, and had molecular weights of Mw: 2,100 and Mn: 1,700 measured by GPC measurement. The PSV 4 was measured by GC and as the result, there was not detected an alkoxysilane monomer.

Preparation of Polysiloxane Vanish Containing Additives

Example 1

To 100 g of the polysiloxane vanish PSV 1 (SiO$_2$ solid content-converted concentration: 12% by mass) obtained in Synthesis Example 1, 0.60 g (5 phr, that is, 5 parts by mass relative to 100 parts by mass of SiO$_2$) of N-α-t-butoxycarbonyl-L-alanine (hereinafter, abbreviated as "Boc-Ala") of Formula (A-1):

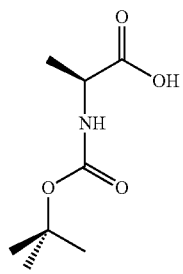

Formula (A-1)

as the amino acid generator was added. Then, the resultant mixture was stirred at room temperature for 30 minutes to completely dissolve Boc-Ala and to prepare a polysiloxane vanish containing an amino acid generator that is a colorless transparent solution as a coating film forming composition (hereinafter, abbreviated as "PSV 1-BAla").

Example 2

In the same manner as in Example 1, except that as the amino acid generator, there was used N-α, N-ω1, N-ω2-tri-tert-butoxycarbonyl-L-arginine (hereinafter, abbreviated as "Boc-Arg") of Formula (A-2):

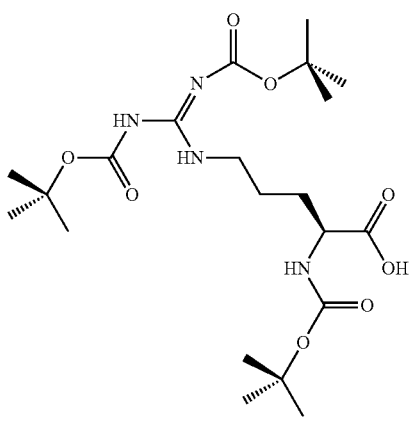

Formula (A-2)

a polysiloxane vanish containing an amino acid generator was prepared as a coating film forming composition (hereinafter, abbreviated as "PSV 1-BArg").

Example 3

In the same manner as in Example 1, except that as the amino acid generator, there was used N-α-tert-butoxycarbonyl-L-aspartic acid (hereinafter, abbreviated as "Boc-Asp") of Formula (A-3):

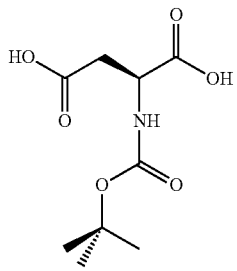

Formula (A-3)

a polysiloxane vanish containing an amino acid generator was prepared as a coating film forming composition (hereinafter, abbreviated as "PSV 1-BAsp").

Example 4

In the same manner as in Example 1, except that as the amino acid generator, there was used N-tert-butoxycarbonyl-glycine (hereinafter, abbreviated as "Boc-Gly") of Formula (A-4):

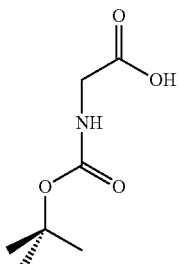

Formula (A-4)

a polysiloxane vanish containing an amino acid generator was prepared as a coating film forming composition (hereinafter, abbreviated as "PSV 1-BGly").

Example 5

In the same manner as in Example 1, except that as the amino acid generator, there was used N-α, im-di-tert-butoxycarbonyl-L-histidine (hereinafter, abbreviated as "Boc-His") of Formula (A-5):

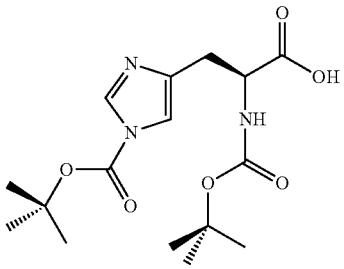

Formula (A-5)

a polysiloxane vanish containing an amino acid generator was prepared as a coating film forming composition (hereinafter, abbreviated as "PSV 1-BHis").

Example 6

In the same manner as in Example 1, except that as the amino acid generator, there was used N-α, N-ε-di-tert-butoxycarbonyl-L-lysine (hereinafter, abbreviated as "Boc-Lys") of Formula (A-6):

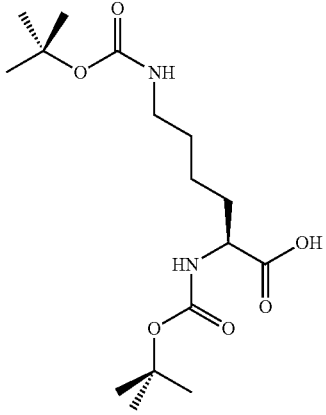

Formula (A-6)

a polysiloxane vanish containing an amino acid generator was prepared as a coating film forming composition (hereinafter, abbreviated as "PSV 1-BLys").

Example 7

In the same manner as in Example 1, except that as the amino acid generator, there was used N-α-(9-fluorenylmethoxycarbonyl)-N-ω1, N-ω2-di-tert-butoxycarbonyl-L-arginine (hereinafter, abbreviated as "FB-Arg") of Formula (A-7):

Formula (A-7)

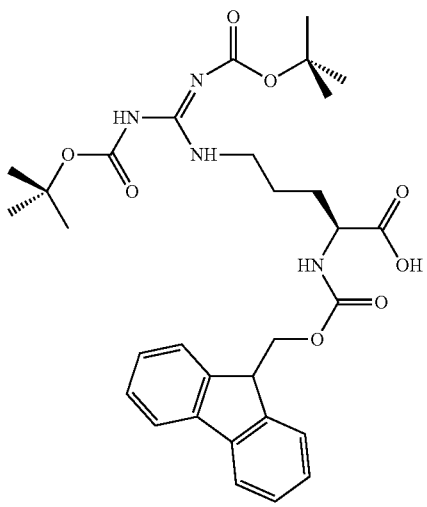

a polysiloxane vanish containing an amino acid generator was prepared as a coating film forming composition (hereinafter, abbreviated as "PSV 1-FBArg").

Example 8

In the same manner as in Example 1, except that as the amino acid generator, there was used N-α-tert-butoxycarbonyl-N-δ-(9-fluorenylmethoxycarbonyl)-L-ornithine (hereinafter, abbreviated as "FB-Orn") of Formula (A-8):

Formula (A-8)

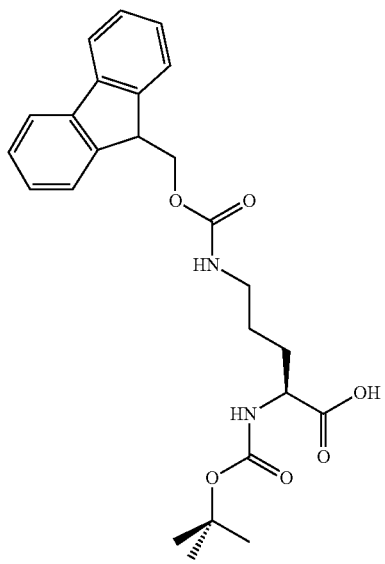

a polysiloxane vanish containing an amino acid generator was prepared as a coating film forming composition (hereinafter, abbreviated as "PSV 1-FBOrn").

Example 9

In the same manner as in Example 1, except that as the amino acid generator, there was used N-α, δ-di-(9-fluorenylmethoxycarbonyl)-L-ornithine (hereinafter, abbreviated as "FF-Orn") of Formula (A-9):

Formula (A-9)

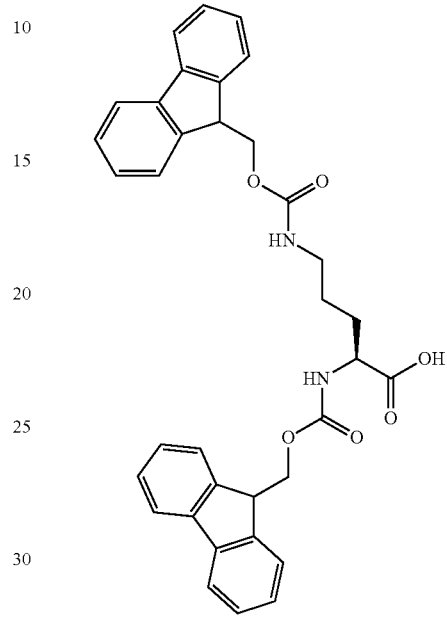

a polysiloxane vanish containing an amino acid generator was prepared as a coating film forming composition (hereinafter, abbreviated as "PSV 1-FFOrn").

Comparative Example 1

In the same manner as in Example 1, except that instead of the amino acid generator as a basic component, monoethanolamine (hereinafter, abbreviated as "MEA") was used, a polysiloxane vanish was prepared as a coating film forming composition (hereinafter, abbreviated as "PSV 1-MEA").

Comparative Example 2

In the same manner as in Example 1, except that instead of the amino acid generator as a basic component, 4-aminopyridine (hereinafter, abbreviated as "4AP") of Formula (A-10):

Formula (A-10)

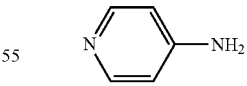

was used, a polysiloxane vanish was prepared as a coating film forming composition (hereinafter, abbreviated as "PSV 1-4AP").

Comparative Example 3

In the same manner as in Example 1, except that instead of the amino acid generator as a thermobase generator, dimethylaminopyridine (hereinafter, abbreviated as "DMAP") of Formula (A-11):

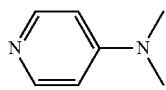

Formula (A-11)

was used, a polysiloxane vanish was prepared as a coating film forming composition (hereinafter, abbreviated as "PSV 1-DMAP").

Comparative Example 4

In the same manner as in Example 1, except that instead of the amino acid generator as an amino acid, L-alanine (hereinafter, abbreviated as "Ala") was used, a polysiloxane vanish was prepared as a coating film forming composition (hereinafter, abbreviated as "PSV 1-Ala").

Comparative Example 5

In the same manner as in Example 1, except that instead of the amino acid generator as an amino acid, L-arginine (hereinafter, abbreviated as "Arg") was used, a polysiloxane vanish was prepared as a coating film forming composition (hereinafter, abbreviated as "PSV 1-Arg").

Comparative Example 6

In the same manner as in Example 1, except that instead of the amino acid generator as an amino acid, L-aspartic acid (hereinafter, abbreviated as "Asp") was used, a polysiloxane vanish was prepared as a coating film forming composition (hereinafter, abbreviated as "PSV 1-Asp").

Comparative Example 7

In the same manner as in Example 1, except that instead of the amino acid generator as an amino acid, glycine (hereinafter, abbreviated as "Gly") was used, a polysiloxane vanish was prepared as a coating film forming composition (hereinafter, abbreviated as "PSV 1-Gly").

Comparative Example 8

In the same manner as in Example 1, except that instead of the amino acid generator as an amino acid, L-histidine (hereinafter, abbreviated as "His") was used, a polysiloxane vanish was prepared as a coating film forming composition (hereinafter, abbreviated as "PSV 1-His").

Comparative Example 9

In the same manner as in Example 1, except that instead of the amino acid generator as an amino acid, L-lysine (hereinafter, abbreviated as "Lys") was used, a polysiloxane vanish was prepared as a coating film forming composition (hereinafter, abbreviated as "PSV 1-Lys").

Comparative Example 10

In the same manner as in Example 1, except that instead of the amino acid generator as an amino acid, L-ornithine (hereinafter, abbreviated as "Orn") was used, a polysiloxane vanish was prepared as a coating film forming composition (hereinafter, abbreviated as "PSV 1-Orn").

[pH Measurement and Preservation Stability Test]

The coating film forming compositions of Examples 1 to 9 and Comparative Examples 1 to 10 were subjected to a preservation stability test.

The preservation stability test was performed by filling 50 mL of each coating film forming composition in a 50 mL of a transparent low alkali-glass vessel, by preserving the vessel in a class-1000 clean room at 23° C. and 55 RH %, and by confirming the change with time of the composition. Specifically, days from a day on which the preservation of the coating film forming composition at room temperature started to a day on which a flaw occurred in the coating film forming composition are defined as the flaw occurrence elapsed days. In the case where a flaw occurred, the condition of the flaw was recorded.

Example 10

The PSV 1-BAla obtained in Example 1 was subjected to the preservation stability test.

Example 11

The PSV 1-BArg obtained in Example 2 was subjected to the preservation stability test.

Example 12

The PSV 1-BAsp obtained in Example 3 was subjected to the preservation stability test.

Example 13

The PSV 1-BGly obtained in Example 4 was subjected to the preservation stability test.

Example 14

The PSV 1-BHis obtained in Example 5 was subjected to the preservation stability test.

Example 15

The PSV 1-BLys obtained in Example 6 was subjected to the preservation stability test.

Example 16

The PSV 1-FBArg obtained in Example 7 was subjected to the preservation stability test.

Example 17

The PSV 1-FBOrn obtained in Example 8 was subjected to the preservation stability test.

Example 18

The PSV 1-FFOrn obtained in Example 9 was subjected to the preservation stability test.

Comparative Example 11

The PSV 1-MEA obtained in Comparative Example 1 was subjected to the preservation stability test.

Comparative Example 12

The PSV 1-4AP obtained in Comparative Example 2 was subjected to the preservation stability test.

Comparative Example 13

The PSV 1-DMAP obtained in Comparative Example 3 was subjected to the preservation stability test.

Comparative Example 14

The PSV 1-Ala obtained in Comparative Example 4 was subjected to the preservation stability test.

Comparative Example 15

The PSV 1-Arg obtained in Comparative Example 5 was subjected to the preservation stability test.

Comparative Example 16

The PSV 1-Asp obtained in Comparative Example 6 was subjected to the preservation stability test.

Comparative Example 17

The PSV 1-Gly obtained in Comparative Example 7 was subjected to the preservation stability test.

Comparative Example 18

The PSV 1-His obtained in Comparative Example 8 was subjected to the preservation stability test.

Comparative Example 19

The PSV 1-Lys obtained in Comparative Example 9 was subjected to the preservation stability test.

Comparative Example 20

The PSV 1-Orn obtained in Comparative Example 10 was subjected to the preservation stability test.

The result of the preservation stability test is shown in Table 1.

TABLE 1

| | Coating film forming composition | Preservation stability at room temperature | |
|---|---|---|---|
| | | Flaw occurrence elapsed days | Flaw conditions |
| Example 10 | PSV 1-BAla | 60 days or more | No abnormality |
| Example 11 | PSV 1-BArg | 60 days or more | No abnormality |
| Example 12 | PSV 1-BAsp | 60 days or more | No abnormality |
| Example 13 | PSV 1-BGly | 60 days or more | No abnormality |
| Example 14 | PSV 1-BHis | 60 days or more | No abnormality |
| Example 15 | PSV 1-BLys | 60 days or more | No abnormality |
| Example 16 | PSV 1-FBArg | 60 days or more | No abnormality |
| Example 17 | PSV 1-FBOrn | 60 days or more | No abnormality |
| Example 18 | PSV 1-FFOrn | 60 days or more | No abnormality |
| Comparative Example 11 | PSV 1-MEA | During stirring | Gelled |
| Comparative Example 12 | PSV 1-4AP | During stirring | Gelled |
| Comparative Example 13 | PSV 1-BAP | During stirring | Gelled |
| Comparative Example 14 | PSV 1-Ala | During stirring | Slightly soluble |
| Comparative Example 15 | PSV 1-Arg | During stirring | Slightly soluble |
| Comparative Example 16 | PSV 1-Asp | During stirring | Slightly soluble |
| Comparative Example 17 | PSV 1-Gly | During stirring | Slightly soluble |
| Comparative Example 18 | PAV 1-His | During stirring | Slightly soluble |
| Comparative Example 19 | PSV 1-Lys | During stirring | Slightly soluble |
| Comparative Example 20 | PSV 1-Orn | During stirring | Slightly soluble |

As shown in Examples 10 to 18, it was found that polysiloxane vanishes containing an amino acid generator have extremely advantageous solubility and even when the polysiloxane vanish was preserved at room temperature for 60 days, it could be stably preserved without deposit and gelation.

On the contrary, it was found that polysiloxane vanishes containing an additive shown in Comparative Examples 11 to 13 were gelled in the middle of stirring, so that these polysiloxane vanishes have remarkably poor stability.

When amino acids of Comparative Examples 14 to 20 in which an amine moiety of the amino acid is not protected with a leaving group were used, these amino acid exhibited slight solubility in a solvent of ethanol, so that the polysiloxane vanish could not be prepared.

From the above results, it was found that the amino acid generator is an additive having remarkably high solubility and excellent preservation stability and when the amino acid generator is added to the polysiloxane vanish, it generates no foreign matter.

[Behavior of Reducing Si—OH Bonds According to Baking Conditions]

A coating film forming composition was produced using a polysiloxane vanish containing an amino acid generator and there was confirmed the variation in the behavior of reducing Si—OH bonds according to the variation in the baking condition when a coating film is produced by coating a substrate with a coating film forming composition.

The production of a film was performed by spin-coating a substrate (base material) with a coating film forming composition under conditions of at 2,000 rpm and for 20 seconds. The coating film forming composition was spin-coated and was baked in the air using a hot plate as baking equipment. The film thickness was set at 500 nm. As the base material, a 4-inch silicon wafer was used.

Example 19

The coating film forming composition (PSV 1-BAla) obtained in Example 1 was spin-coated and was baked at 250° C. for 5 minutes. The coating film after baking was pared off and the resultant sample piece was subjected to an FT-IR spectrum measurement by a KBr method.

Example 20

In the same manner as in Example 19, except that the coating film forming composition (PSV 1-BArg) obtained in Example 2 was used, the coating film was formed and a sample piece thereof was subjected to an FT-IR spectrum measurement by a KBr method.

Example 21

In the same manner as in Example 19, except that the coating film forming composition (PSV 1-BAsp) obtained in Example 3 was used, the coating film was formed and a sample piece thereof was subjected to an FT-IR spectrum measurement by a KBr method.

Example 22

In the same manner as in Example 19, except that the coating film forming composition (PSV 1-BGly) obtained in Example 4 was used, the coating film was formed and a sample piece thereof was subjected to an FT-IR spectrum measurement by a KBr method.

Example 23

In the same manner as in Example 19, except that the coating film forming composition (PSV 1-BHis) obtained in Example 5 was used, the coating film was formed and a sample piece thereof was subjected to an FT-IR spectrum measurement by a KBr method.

Example 24

In the same manner as in Example 19, except that the coating film forming composition (PSV 1-BLys) obtained in Example 6 was used, the coating film was formed and a sample piece thereof was subjected to an FT-IR spectrum measurement by a KBr method.

Example 25

In the same manner as in Example 19, except that the coating film forming composition (PSV 1-FBArg) obtained in Example 7 was used, the coating film was formed and a sample piece thereof was subjected to an FT-IR spectrum measurement by a KBr method.

Example 26

In the same manner as in Example 19, except that the coating film forming composition (PSV 1-FBOrn) obtained in Example 8 was used, the coating film was formed and a sample piece thereof was subjected to an FT-IR spectrum measurement by a KBr method.

Example 27

In the same manner as in Example 19, except that the coating film forming composition (PSV 1-FFOrn) obtained in Example 9 was used, the coating film was formed and a sample piece thereof was subjected to an FT-IR spectrum measurement by a KBr method.

Comparative Example 21

In the same manner as in Example 19, except that as the coating film forming composition, the polysiloxane vanish (PSV 1) obtained in Synthesis Example 1 was used, the coating film was formed and a sample piece thereof was subjected to an FT-IR spectrum measurement by a KBr method.

Comparative Example 22

The polysiloxane vanish (PSV 1) obtained in Synthesis Example 1 and used as the coating film forming composition was spin-coated and the composition was baked at 250° C. for 120 minutes. The coating film after baking was pared off and the resultant sample piece was subjected to an FT-IR spectrum measurement by a KBr method.

Comparative Example 23

The polysiloxane vanish (PSV 1) obtained in Synthesis Example 1 and used as the coating film forming composition was spin-coated and the composition was baked at 300° C. for 120 minutes. The coating film after baking was pared off and the resultant sample piece was subjected to an FT-IR spectrum measurement by a KBr method.

Comparative Example 24

The polysiloxane vanish (PSV 1) obtained in Synthesis Example 1 and used as the coating film forming composition was spin-coated and the composition was baked at 400° C. for 120 minutes. The coating film after baking was pared off and the resultant sample piece was subjected to an FT-IR spectrum measurement by a KBr method.

The results of the FT-IR measurement in Examples 19 to 27 and Comparative Examples 21 to 24 are shown in FIGS. 1 to 9 and FIGS. 30 to 33. In the figures, there was focused attention on a peak at around 3,500 cm$^{-1}$ ascribed to an OH stretching vibration of a Si—OH bond.

In FIGS. 1 to 9, the number of Si—OH bonds of a film produced by baking at 250° C. for 5 minutes, the film formed from a coating film forming composition in which an amino acid generator was added to the polysiloxane vanish (PSV 1), was remarkably reduced. In the cases of arginine, histidine, and lysine used in Examples 20, 23, and 24 among the amino acid generators, it was confirmed that the peak for the Si—OH bond disappeared completely.

In a film produced by baking at 250° C. for 5 minutes, the film formed from as the coating film forming composition, the polysiloxane vanish (PSV 1) in Comparative Example 21, extremely many Si—OH bonds remained, and it was found that as in Comparative Examples 22 to 24, even by raising the baking temperature or by increasing the baking time, the Si—OH bond did not disappear.

[pH Measurement of Amino Acid Generator]

In order to grasp the pH value before and after a leaving group substituted with an N atom at an amine moiety contained in an amino acid is eliminated, the pH measurement was performed as follows.

The pH measurement was performed using a digital pH meter after the calibration was performed using pH standard solutions of pH 4, 7, and 9 for the calibration.

Measurement Example 1

A solution mixture in a mass ratio of pure water:ethanol=1:5 was prepared and to the solution mixture, Boc-Ala was added so that Boc-Ala had a concentration of 5% by mass to completely dissolve Boc-Ala. The pH value of the resultant solution was measured.

Measurement Example 2

In the same manner as in Measurement Example 1, except that Boc-Arg was used instead of Boc-Ala, the solution was prepared, and the pH value of the prepared solution was measured.

Measurement Example 3

In the same manner as in Measurement Example 1, except that Boa-Asp was used instead of Boc-Ala, the solution was prepared, and the pH value of the prepared solution was measured.

Measurement Example 4

In the same manner as in Measurement Example 1, except that Boc-Gly was used instead of Boc-Ala, the solution was prepared, and the pH value of the prepared solution was measured.

Measurement Example 5

In the same manner as in Measurement Example 1, except that Boc-His was used instead of Boc-Ala, the solution was prepared, and the pH value of the prepared solution was measured.

Measurement Example 6

In the same manner as in Measurement Example 1, except that Boc-Lys was used instead of Boc-Ala, the solution was prepared, and the pH value of the prepared solution was measured.

Measurement Example 7

In the same manner as in Measurement Example 1, except that FB-Arg was used instead of Boc-Ala, the solution was prepared, and the pH value of the prepared solution was measured.

Measurement Example 8

In the same manner as in Measurement Example 1, except that FB-Orn was used instead of Boc-Ala, the solution was prepared, and the pH value of the prepared solution was measured.

Measurement Example 9

In the same manner as in Measurement Example 1, except that FF-Orn was used instead of Boc-Ala, the solution was prepared, and the pH value of the prepared solution was measured.

Measurement Example 10

In the same manner as in Measurement Example 1, except that Ala was used instead of Boc-Ala, the solution was prepared, and the pH value of the prepared solution was measured.

Measurement Example 11

In the same manner as in Measurement Example 1, except that Arg was used instead of Boc-Ala, the solution was prepared, and the pH value of the prepared solution was measured.

Measurement Example 12

In the same manner as in Measurement Example 1, except that Asp was used instead of Boc-Ala, the solution was prepared, and the pH value of the prepared solution was measured.

Measurement Example 13

In the same manner as in Measurement Example 1, except that Gly was used instead of Boc-Ala, the solution was prepared, and the pH value of the prepared solution was measured.

Measurement Example 14

In the same manner as in Measurement Example 1, except that His was used instead of Boc-Ala, the solution was prepared, and the pH value of the prepared solution was measured.

Measurement Example 15

In the same manner as in Measurement Example 1, except that Lys was used instead of Boc-Ala, the solution was prepared, and the pH value of the prepared solution was measured.

Measurement Example 16

In the same manner as in Measurement Example 1, except that Orn was used instead of Boc-Ala, the solution was prepared, and the pH value of the prepared solution was measured.

The results of Measurement Examples 1 to 16 are shown in Table 2.

TABLE 2

|  | Solute | pH |
| --- | --- | --- |
| Measurement Example 1 | Boc-Ala | 2.52 |
| Measurement Example 2 | Boc-Arg | 4.08 |
| Measurement Example 3 | Boc-Asp | 2.40 |
| Measurement Example 4 | Boc-Gly | 2.41 |
| Measurement Example 5 | Boc-His | 3.85 |
| Measurement Example 6 | Boc-Lys | 4.00 |
| Measurement Example 7 | FB-Arg | 4.02 |
| Measurement Example 8 | FB-Orn | 4.01 |
| Measurement Example 9 | FF-Orn | 4.11 |
| Measurement Example 10 | Ala | 6.30 |
| Measurement Example 11 | Arg | 11.38 |
| Measurement Example 12 | Asp | 3.80 |
| Measurement Example 13 | Gly | 6.51 |
| Measurement Example 14 | His | 7.54 |
| Measurement Example 15 | Lys | 10.35 |
| Measurement Example 16 | Orn | 10.41 |

In the amino acid generator, an amine moiety developing basicity is protected by a protecting group and consequently, the amino acid generator exhibits property of a carboxylic acid, so that as shown in Measurement Examples 1 to 9, the pH values became between 4.11 and 2.40. The pH value around 4 is in a pH range in which the polysiloxane vanish can be stably preserved, which is especially preferred.

On the contrary, when a protecting group is eliminated to exhibit property of an amine, the pH value becomes those as in Measurement Examples 10 to 16 and particularly in the cases of arginine, histidine, lysine, and ornithine, it was confirmed that the pH value inclines to basicity. This phenomenon means that an external stimulation for eliminating the protecting group is heat, so that a polysiloxane vanish is formed into a film on a substrate and during baking, the resultant film inclines to basicity. The condensation-polymerization of the polysiloxane remarkably progresses in a basic range, so that the pH value of each film produced using arginine, histidine, lysine, and ornithine inclines to basicity and consequently, arginine, histidine, lysine, and ornithine are extremely preferred. Also with respect to a film produced using an amino acid generator that does not incline to basicity after the elimination of a protecting group, from the result in FIG. 3 in which a peak for an Si—OH bond decreases, it is indicated that the condensation-polymerization of the polysiloxane progresses when an amine moiety is developed.

[Behavior of Reducing Si—OH Bonds According to Baking Temperatures]

There was confirmed the baking temperature dependency of the behavior of reducing Si—OH bonds when Boc-Arg most effective for reducing Si—OH bonds was used as the amino acid generator.

The film formation was performed by a spin coating method under conditions of at 2,000 rpm and for 20 seconds. The coating film forming composition was spin-coated and was baked in the air using a hot plate as baking equipment. The film thickness was set to 500 nm. As the base material, a 4-inch silicon wafer was used.

Example 28

The coating film forming composition (PSV 1-BArg) obtained in Example 2 was spin-coated and was baked at 100° C. for 5 minutes. The coating film after baking was pared off and the resultant sample piece was subjected to an FT-IR spectrum measurement by a KBr method.

Example 29

The coating film forming composition (PSV 1-BArg) obtained in Example 2 was spin-coated and was baked at 150° C. for 5 minutes. The coating film after baking was pared off and the resultant sample piece was subjected to an FT-IR spectrum measurement by a KBr method.

Example 30

The coating film forming composition (PSV 1-BArg) obtained in Example 2 was spin-coated and was baked at 200° C. for 5 minutes. The coating film after baking was pared off and the resultant sample piece was subjected to an FT-IR spectrum measurement by a KBr method.

Comparative Example 25

The polysiloxane vanish (PSV 1) obtained in Synthesis Example 1 and used as the coating film forming composition was spin-coated and was baked at 100° C. for 5 minutes. The coating film after baking was pared off and the resultant sample piece was subjected to an FT-IR spectrum measurement by a KBr method.

Comparative Example 26

The polysiloxane vanish (PSV 1) obtained in Synthesis Example 1 and used as the coating film forming composition was spin-coated and was baked at 150° C. for 5 minutes. The coating film after baking was pared off and the resultant sample piece was subjected to an FT-IR spectrum measurement by a KBr method.

Comparative Example 27

The polysiloxane vanish (PSV 1) obtained in Synthesis Example 1 and used as the coating film forming composition was spin-coated and was baked at 200° C. for 5 minutes. The coating film after baking was pared off and the resultant sample piece was subjected to an FT-IR spectrum measurement by a KBr method.

The results of Example 20 and Examples 28 to 30 are shown in FIG. 2 and FIGS. 10 to 12 and the results of Comparative Example 21 and Comparative Examples 25 to 27 are shown in FIG. 30 and FIGS. 34 to 36.

Figure 2:
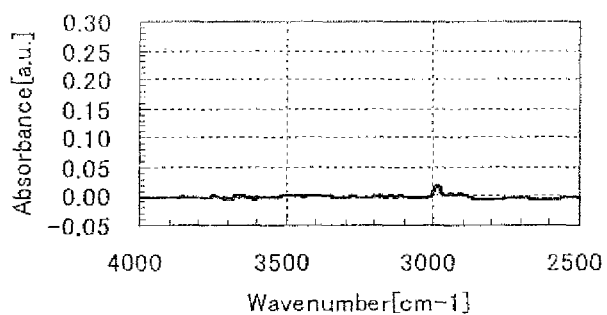
FIG. 2 is a graph showing an FT-IR spectrum of the film obtained in Example 20.
Figure 3:
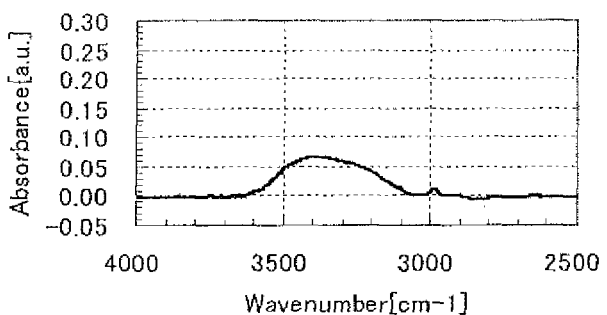
FIG. 3 is a graph showing an FT-IR spectrum of the film obtained in Example 21.
Figure 4:
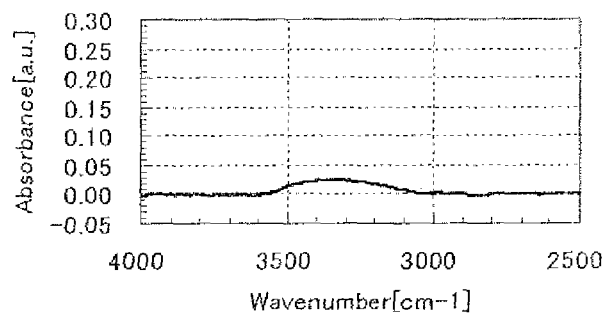
FIG. 4 is a graph showing an FT-IR spectrum of the film obtained in Example 22.
Figure 5:
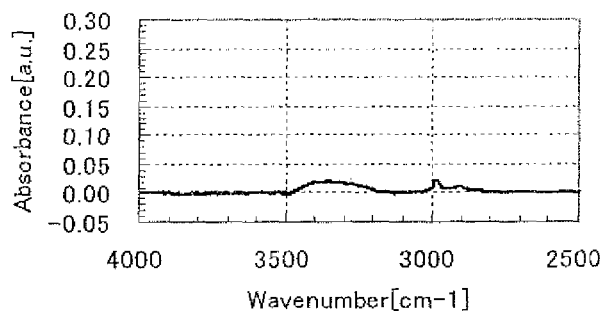
FIG. 5 is a graph showing an FT-IR spectrum of the film obtained in Example 23.
Figure 6:
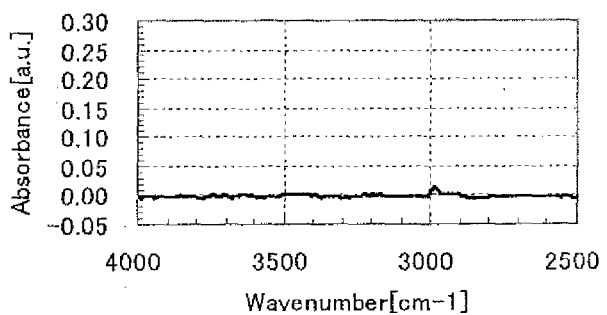
FIG. 6 is a graph showing an FT-IR spectrum of the film obtained in Example 24.
Figure 7:
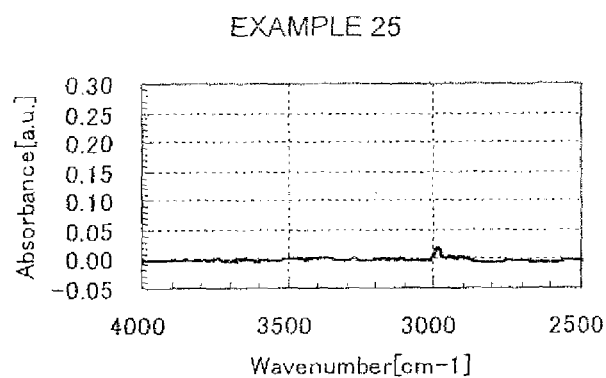
FIG. 7 is a graph showing an FT-IR spectrum of the film obtained in Example 25.
Figure 8:
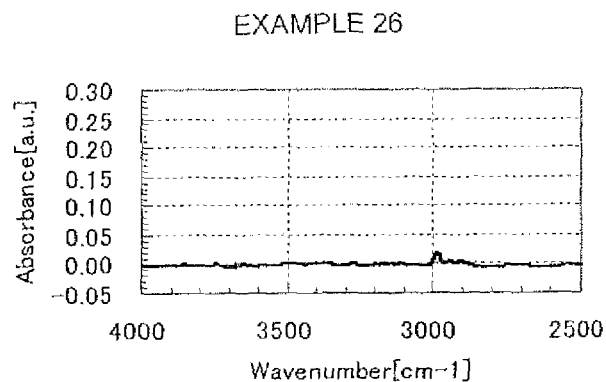
FIG. 8 is a graph showing an FT-IR spectrum of the film obtained in Example 26.
Figure 9:
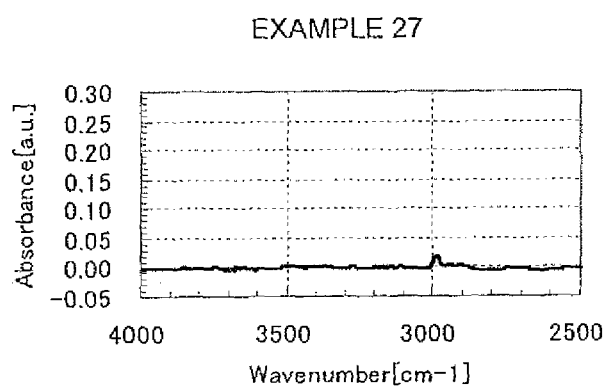
FIG. 9 is a graph showing an FT-IR spectrum of the film obtained in Example 27.
Figure 10:
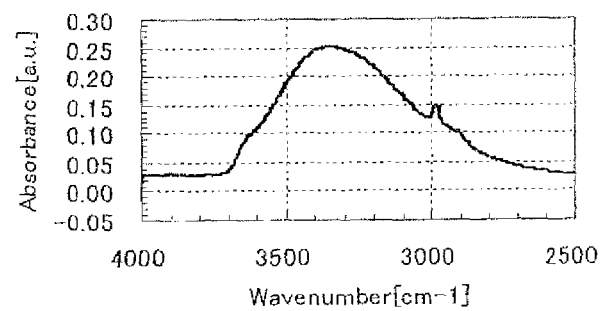
FIG. 10 is a graph showing an FT-IR spectrum of the film obtained in Example 28.
Figure 11:
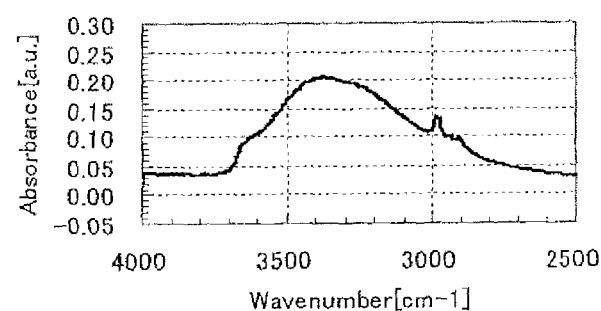
FIG. 11 is a graph showing an FT-IR spectrum of the film obtained in Example 29.
Figure 12:
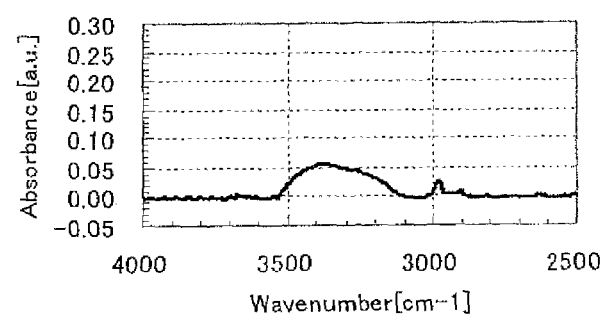
FIG. 12 is a graph showing an FT-IR spectrum of the film obtained in Example 30.
Figure 13:
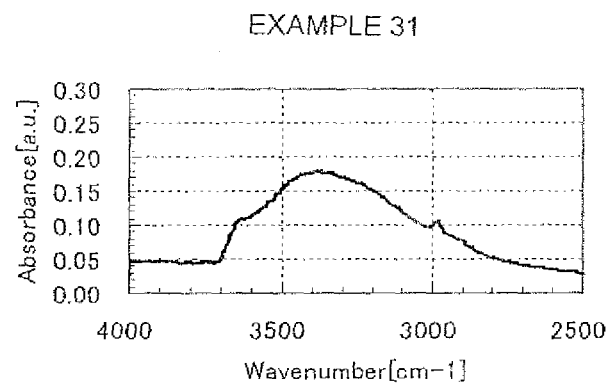
FIG. 13 is a graph showing an FT-IR spectrum of the film obtained in Example 31.

From the results in FIG. 2 and FIG. 12, it was found that in a film obtained by coating a base material with a coating film forming composition obtained by adding Boc-Arg as the amino acid generator to a polysiloxane vanish, only by baking the film at 200° C. for 5 minutes, the Si—OH bond remarkably disappeared and by baking the film at 250° C. for 5 minutes, the Si—OH bond completely disappeared.

On the contrary, as the baking temperature dependency of a film obtained by coating a base material solely with the polysiloxane vanish (PSV 1) as the coating film forming composition, it was confirmed that by baking the film at 250° C. for 5 minutes, though certain Si—OH bonds disappeared, the Si—OH bond did not dramatically disappear and remained.

In comparison of Example 29 with Comparative Example 21, as the relative evaluation of FT-IR, substantially the same peak strength of the Si—OH bond was obtained in these Examples and it is considered that the temperature at which the amino acid generator develops basicity of an amine by heat starts from around 150° C.

[Behavior of Reducing Si—OH Bonds According to Adding Amount of Amino Acid Generator]

There was confirmed the adding amount dependency of the behavior of reducing Si—OH bonds when Boc-Arg most effective for reducing Si—OH bonds was used as the amino acid generator.

The film formation was performed by a spin coating method under conditions of at 2,000 rpm and for 20 seconds. The coating film forming composition was spin-coated and was baked in the air using a hot plate as baking equipment. The film thickness was set to 500 nm. As the base material, a 4-inch silicon wafer was used.

Example 31

In the same manner as in Example 2, except that Boc-Arg was added to the polysiloxane vanish in an amount of 0.1 phr (that is, the composition contains Boc-Arg in an amount of 0.1 parts by mass relative to 100 parts by mass of $SiO_2$ in the polysiloxane vanish PSV 1), a coating film forming composition (hereinafter, abbreviated as "PSV 1-BArg-0.1 phr") was prepared. The obtained coating film forming composition (PSV 1-BArg-0.1 phr) was spin-coated and was baked at 250° C. for 5 minutes. The coating film after baking was pared off and the resultant sample piece was subjected to an FT-IR spectrum measurement by a KBr method.

Example 32

In the same manner as in Example 2, except that Boc-Arg was added to the polysiloxane vanish in an amount of 0.5 phr (that is, the composition contains Boc-Arg in an amount of 0.5 parts by mass relative to 100 parts by mass of $SiO_2$ in the polysiloxane vanish PSV 1), a coating film forming composition (hereinafter, abbreviated as "PSV 1-BArg-0.5 phr") was prepared. The obtained coating film forming composition (PSV 1-BArg-0.5 phr) was spin-coated and was baked at 250° C. for 5 minutes. The coating film after baking was pared off and the resultant sample piece was subjected to an FT-IR spectrum measurement by a KBr method.

Example 33

In the same manner as in Example 2, except that Boc-Arg was added to the polysiloxane vanish in an amount of 1.0 phr (that is, the composition contains Boc-Arg in an amount of 0.1 parts by mass relative to 100 parts by mass of $SiO_2$ in the polysiloxane vanish PSV 1), a coating film forming composition (hereinafter, abbreviated as "PSV 1-BArg-1.0 phr") was prepared. The obtained coating film forming composition (PSV 1-BArg-1.0 phr) was spin-coated and was baked at 250° C. for 5 minutes. The coating film after baking was pared off and the resultant sample piece was subjected to an FT-IR spectrum measurement by a KBr method.

Example 34

In the same manner as in Example 2, except that Boc-Arg was added to the polysiloxane vanish in an amount of 2.5 phr (that is, the composition contains Boc-Arg in an amount of 2.5 parts by mass relative to 100 parts by mass of $SiO_2$ in the polysiloxane vanish PSV 1), a coating film forming composition (hereinafter, abbreviated as "PSV 1-BArg-2.5 phr") was prepared. The obtained coating film forming composition (PSV 1-BArg-2.5 phr) was spin-coated and was baked at 250° C. for 5 minutes. The coating film after baking was pared off and the resultant sample piece was subjected to an FT-IR spectrum measurement by a KBr method.

The results of Example 20 and Examples 31 to 34 are shown in FIG. 2 and FIGS. 13 to 16.

Figure 14:
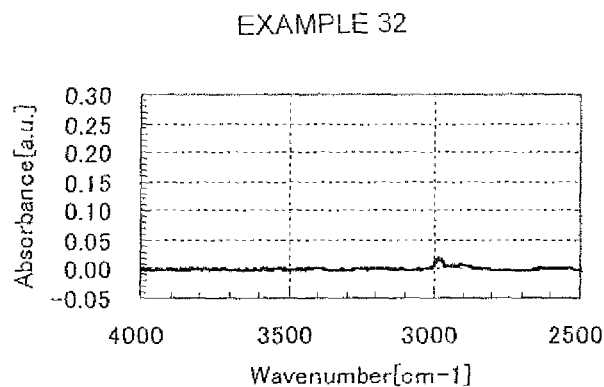
FIG. 14 is a graph showing an FT-IR spectrum of the film obtained in Example 32.
Figure 15:
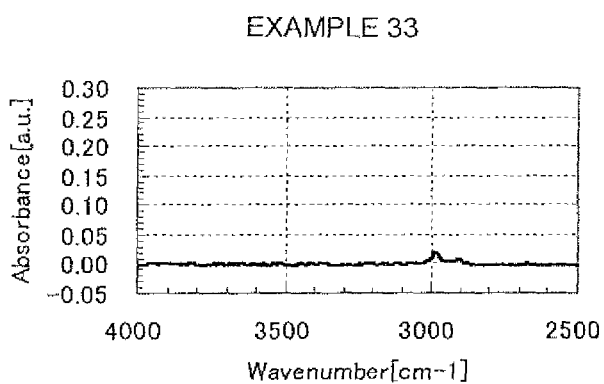
FIG. 15 is a graph showing an FT-IR spectrum of the film obtained in Example 33.
Figure 16:
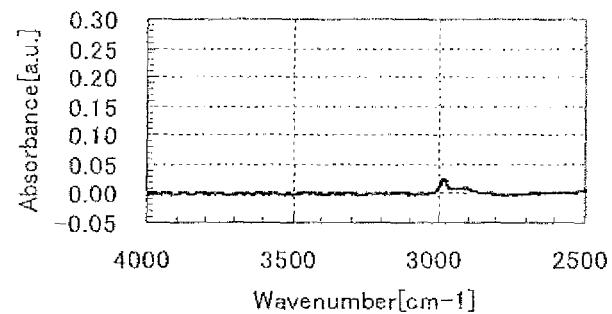
FIG. 16 is a graph showing an FT-IR spectrum of the film obtained in Example 34.
Figure 17:
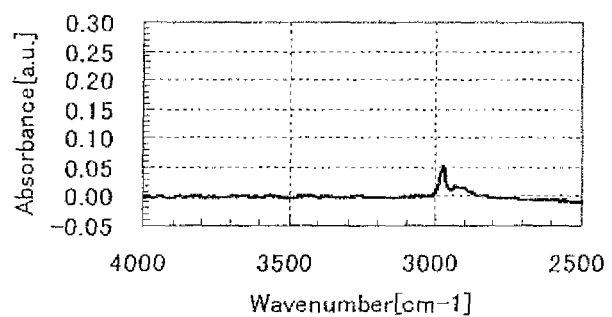
FIG. 17 is a graph showing an FT-IR spectrum of the film obtained in Example 35.
Figure 18:
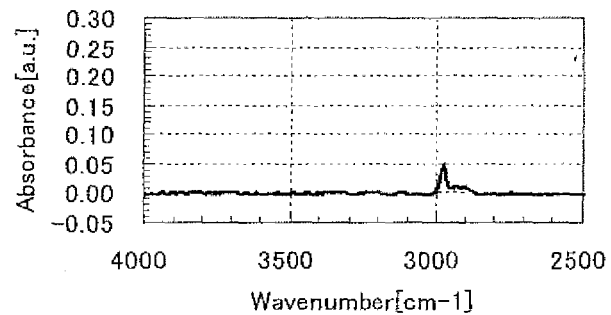
FIG. 18 is a graph showing an FT-IR spectrum of the film obtained in Example 36.
Figure 19:
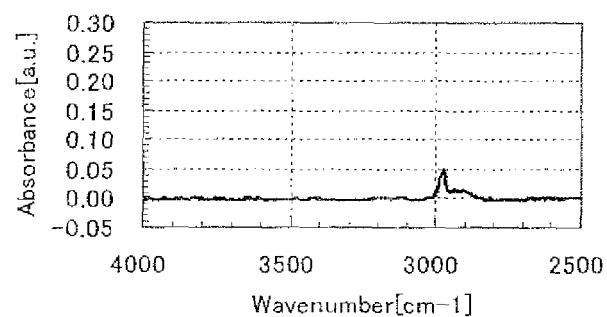
FIG. 19 is a graph showing an FT-IR spectrum of the film obtained in Example 37.
Figure 20:
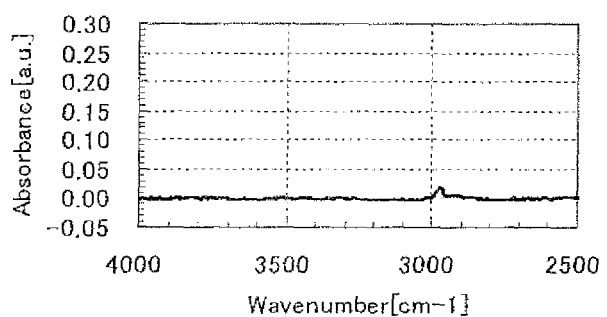
FIG. 20 is a graph showing an FT-IR spectrum of the film obtained in Example 38.
Figure 21:
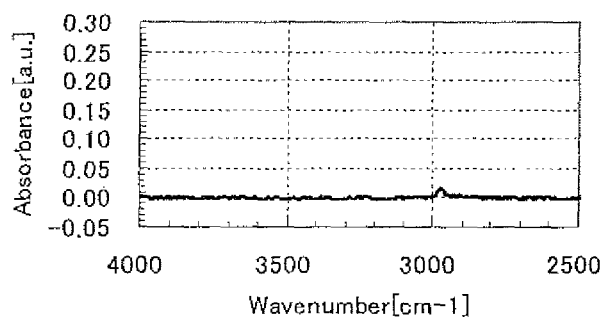
FIG. 21 is a graph showing an FT-IR spectrum of the film obtained in Example 39.
Figure 22:
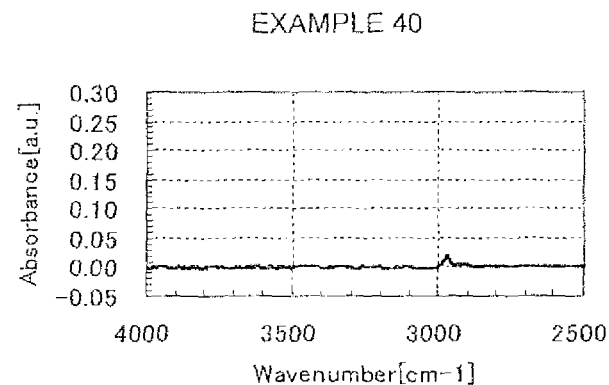
FIG. 22 is a graph showing an FT-IR spectrum of the film obtained in Example 40.
Figure 23:
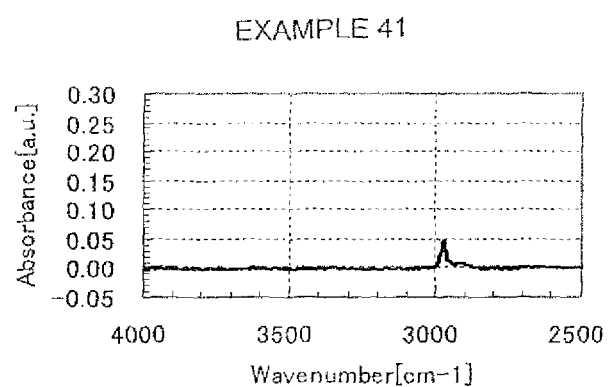
FIG. 23 is a graph showing an FT-IR spectrum of the film obtained in Example 41.
Figure 24:
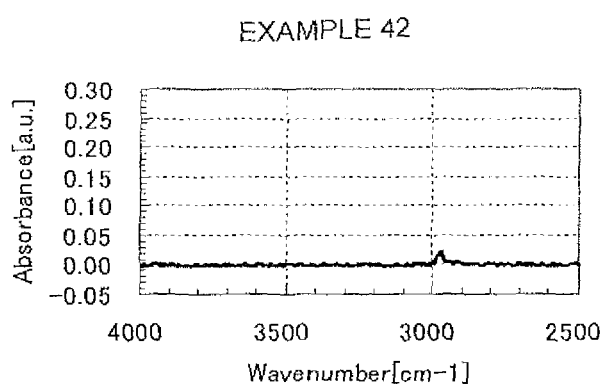
FIG. 24 is a graph showing an FT-IR spectrum of the film obtained in Example 42.
Figure 25:
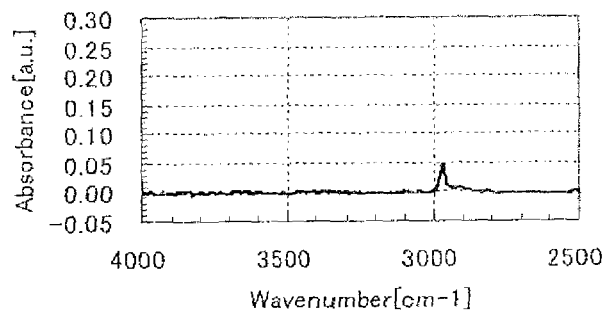
FIG. 25 is a graph showing an FT-IR spectrum of the film obtained in Example 43.
Figure 26:
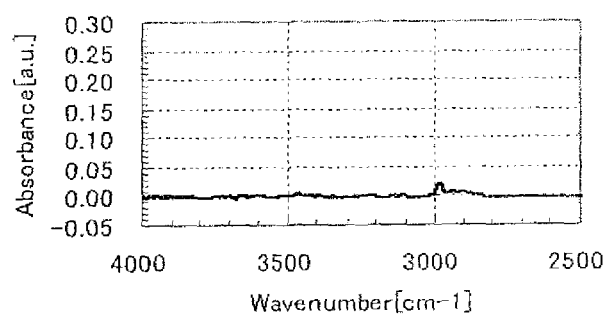
FIG. 26 is a graph showing an FT-IR spectrum of the film obtained in Example 44.
Figure 27:
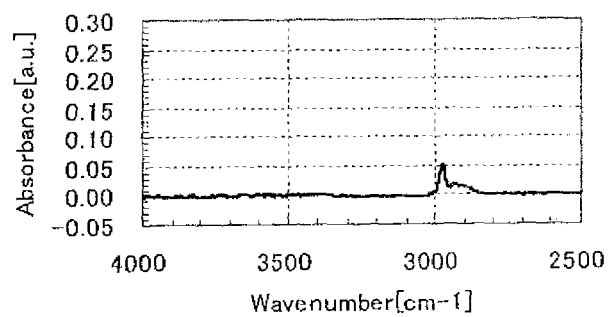
FIG. 27 is a graph showing an FT-IR spectrum of the film obtained in Example 45.
Figure 28:
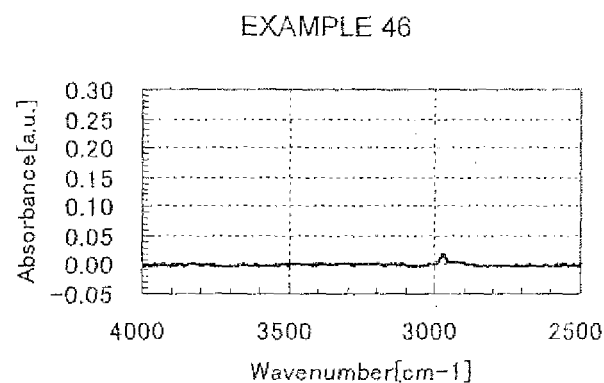
FIG. 28 is a graph showing an FT-IR spectrum of the film obtained in Example 46.
Figure 29:
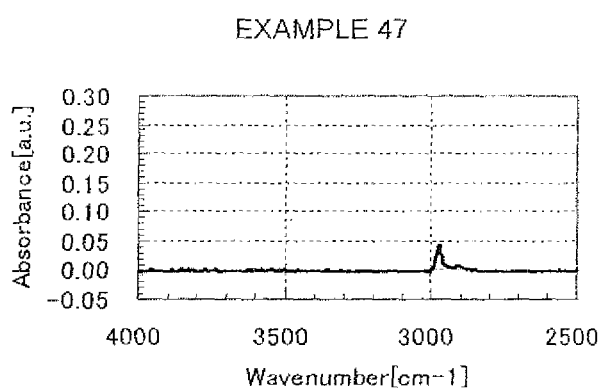
FIG. 29 is a graph showing an FT-IR spectrum of the film obtained in Example 47.
Figure 30:
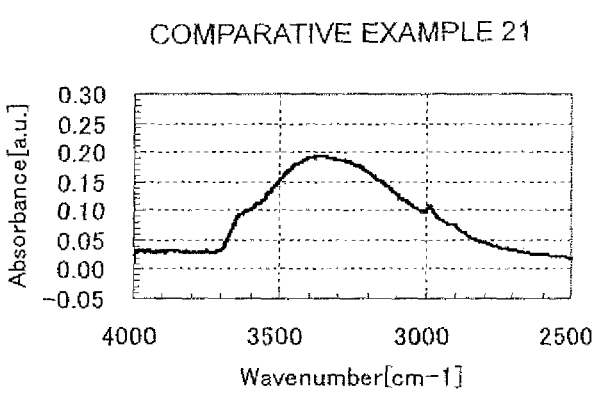
FIG. 30 is a graph showing an FT-IR spectrum of the film obtained in Comparative Example 21.
Figure 31:
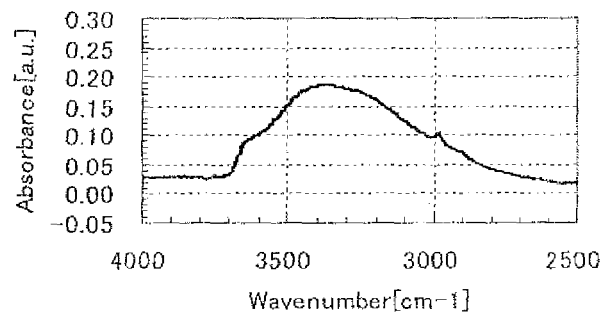
FIG. 31 is a graph showing an FT-IR spectrum of the film obtained in Comparative Example 22.
Figure 32:
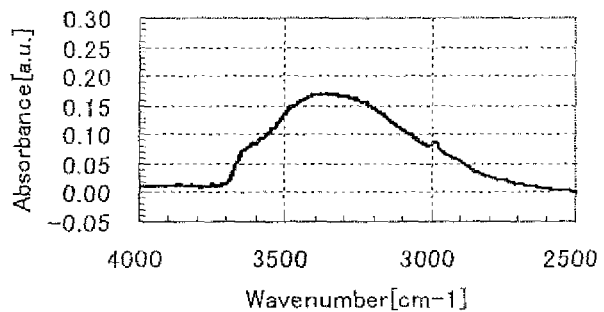
FIG. 32 is a graph showing an FT-IR spectrum of the film obtained in Comparative Example 23.
Figure 33:
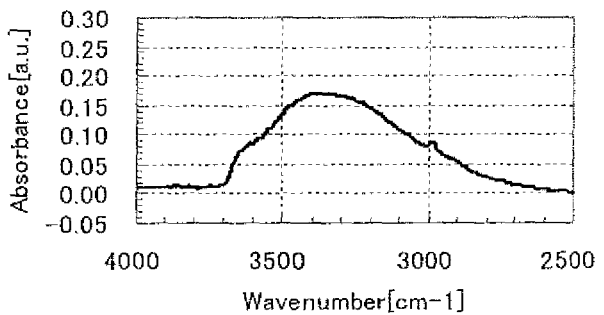
FIG. 33 is a graph showing an FT-IR spectrum of the film obtained in Comparative Example 24.
Figure 34:
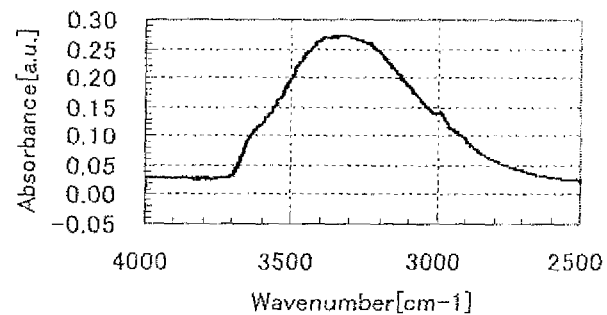
FIG. 34 is a graph showing an FT-IR spectrum of the film obtained in Comparative Example 25.
Figure 35:
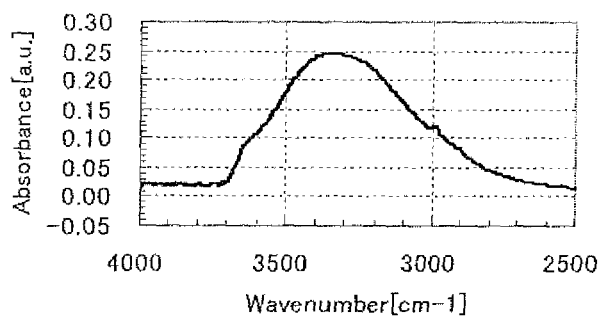
FIG. 35 is a graph showing an FT-IR spectrum of the film obtained in Comparative Example 26.
Figure 36:
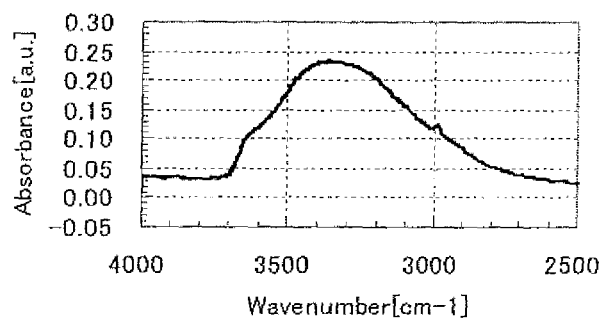
FIG. 36 is a graph showing an FT-IR spectrum of the film obtained in Comparative Example 27.
Figure 37:
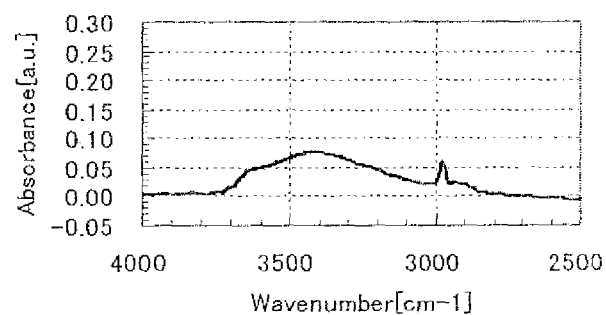
FIG. 37 is a graph showing an FT-IR spectrum of the film obtained in Comparative Example 28.
Figure 38:
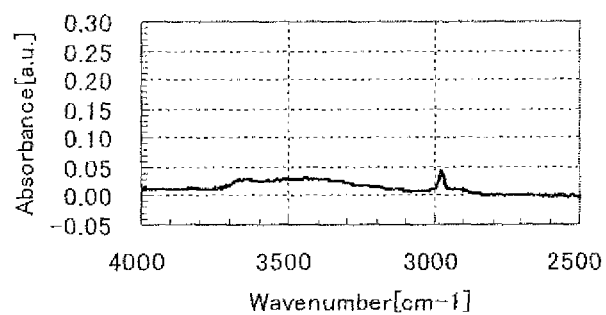
FIG. 38 is a graph showing an FT-IR spectrum of the film obtained in Comparative Example 29.
Figure 39:
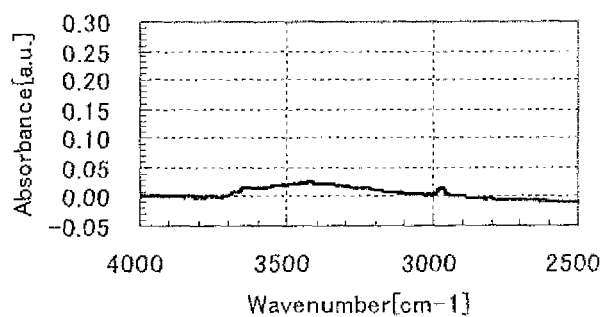
FIG. 39 is a graph showing an FT-IR spectrum of the film obtained in Comparative Example 30.
Figure 40:
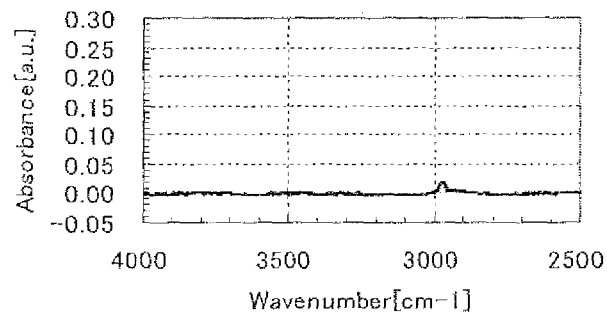
FIG. 40 is a graph showing an FT-IR spectrum of the film obtained in Comparative Example 31.
Figure 41:
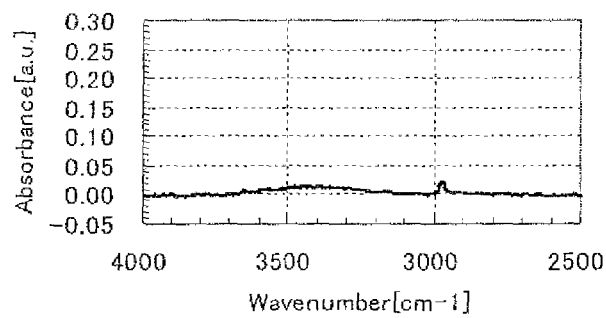
FIG. 41 is a graph showing an FT-IR spectrum of the film obtained in Comparative Example 32.
Figure 42:
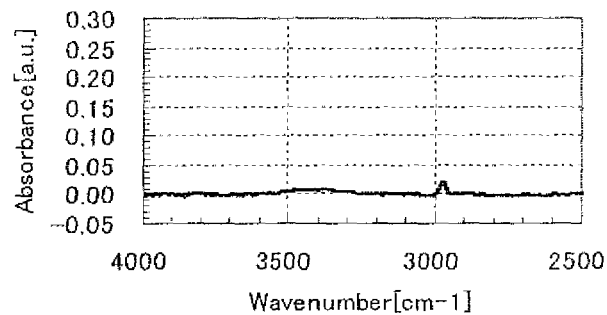
FIG. 42 is a graph showing an FT-IR spectrum of the film obtained in Comparative Example 33.
Figure 43:
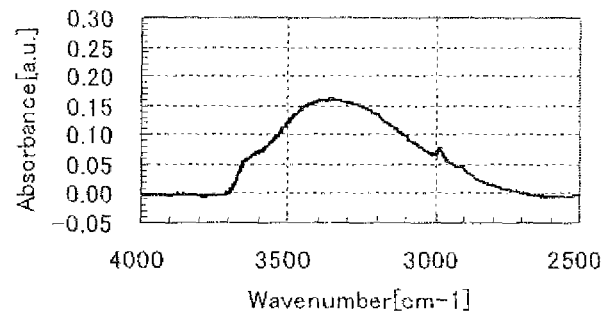
FIG. 43 is a graph showing an FT-IR spectrum of the film obtained in Comparative Example 34.
Figure 44:
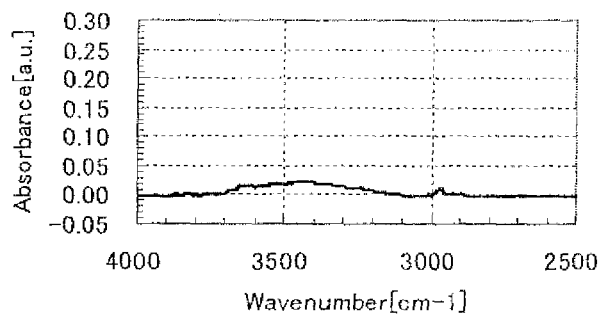
FIG. 44 is a graph showing an FT-IR spectrum of the film obtained in Comparative Example 35.
Figure 45:
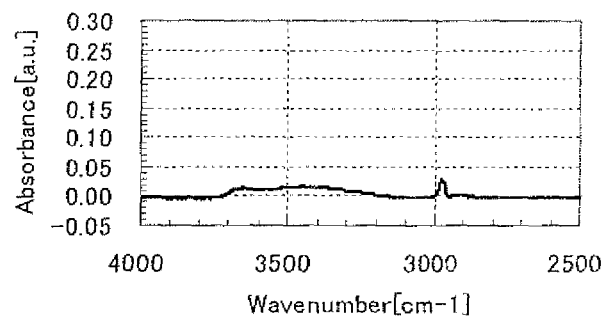
FIG. 45 is a graph showing an FT-IR spectrum of the film obtained in Comparative Example 36.
Figure 46:
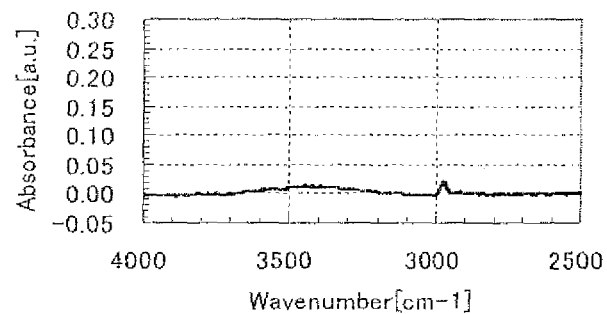
FIG. 46 is a graph showing an FT-IR spectrum of the film obtained in Comparative Example 37.
Figure 47:
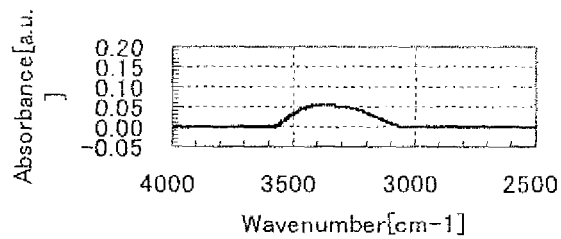
FIG. 47 is a graph showing an FT-IR spectrum of the film obtained in Example 48.

As shown in FIG. 14 and FIG. 15, from the results of the FT-IR measurement of films produced using coating film forming compositions in which the adding amount of Boc-Arg most effective for reducing Si—OH bonds to the polysiloxane vanish was varied, it was found that a composition in which 0.1 phr of Boc-Arg was added developed no effect for reducing Si—OH bonds; however, a composition in which 0.5 phr or more of Boc-Arg was added developed the effect for reducing Si—OH bonds and the Si—OH bond disappeared completely.

With a remarkably small amount of 0.5 phr, the effect can be developed, so that the number of Si—OH bonds can be dramatically reduced without largely changing the property of the polysiloxane.

[Behavior of Reducing Si—OH Bonds According to Baking Conditions of Polysiloxane Produced by Copolymerization]

It was investigated whether Si—OH bonds can be reduced by using the amino acid generator also with respect to a polysiloxane vanish produced by a copolymerization.

The film formation was performed by a spin coating method under conditions of at 2,000 rpm and for 20 seconds. The coating film forming composition was spin-coated and was baked in the air using a hot plate as baking equipment. The film thickness was set to 500 nm. As the base material, a 4-inch silicon wafer was used.

Example 35

In the same manner as in Example 1, Boc-Arg was added to the polysiloxane vanish PSV 2 obtained in Synthesis Example 2 to prepare a coating film forming composition (hereinafter, abbreviated as "PSV 2-BArg"). The coating film forming composition (PSV 2-BArg) was spin-coated and was baked at 250° C. for 5 minutes. The coating film after baking was pared off and the resultant sample piece was subjected to an FT-IR spectrum measurement by a KBr method.

Example 36

In the same manner as in Example 1, Boc-Lys was added to the polysiloxane vanish PSV 2 obtained in Synthesis Example 2 to prepare a coating film forming composition (hereinafter, abbreviated as "PSV 2-BLys"). The coating film forming composition (PSV 2-BLys) was spin-coated and was baked at 250° C. for 5 minutes. The coating film after baking was pared off and the resultant sample piece was subjected to an FT-IR spectrum measurement by a KBr method.

Example 37

In the same manner as in Example 1, Boc-His was added to the polysiloxane vanish PSV 2 obtained in Synthesis Example 2 to prepare a coating film forming composition (hereinafter, abbreviated as "PSV 2-BHis"). The coating film forming composition (PSV 2-BHis) was spin-coated and was baked at 250° C. for 5 minutes. The coating film after baking was pared off and the resultant sample piece was subjected to an FT-IR spectrum measurement by a KBr method.

Example 38

In the same manner as in Example 1, Boc-Arg was added to the polysiloxane vanish PSV 3 obtained in Synthesis Example 3 to prepare a coating film forming composition (hereinafter, abbreviated as "PSV 3-BArg"). The coating film forming composition (PSV 3-BArg) was spin-coated and was baked at 250° C. for 5 minutes. The coating film after baking was pared off and the resultant sample piece was subjected to an FT-IR spectrum measurement by a KBr method.

Example 39

In the same manner as in Example 1, Boc-Lys was added to the polysiloxane vanish PSV 3 obtained in Synthesis Example 3 to prepare a coating film forming composition (hereinafter, abbreviated as "PSV 3-BLys"). The coating film forming composition (PSV 3-BLys) was spin-coated and was baked at 250° C. for 5 minutes. The coating film after baking was pared off and the resultant sample piece was subjected to an FT-IR spectrum measurement by a KBr method.

Example 40

In the same manner as in Example 1, Boc-His was added to the polysiloxane vanish PSV 3 obtained in Synthesis Example 3 to prepare a coating film forming composition (hereinafter, abbreviated as "PSV 3-BHis"). The coating film forming composition (PSV 3-BHis) was spin-coated and was baked at 250° C. for 5 minutes. The coating film after baking was pared off and the resultant sample piece was subjected to an FT-IR spectrum measurement by a KBr method.

Example 41

In the same manner as in Example 1, Boc-Arg was added to the polysiloxane vanish PSV 4 obtained in Synthesis Example 4 to prepare a coating film forming composition (hereinafter, abbreviated as "PSV 4-BArg"). The coating film forming composition (PSV 4-BArg) was spin-coated and was baked at 250° C. for 5 minutes. The coating film after baking was pared off and the resultant sample piece was subjected to an FT-IR spectrum measurement by a KBr method.

Example 42

In the same manner as in Example 1, Boc-Lys was added to the polysiloxane vanish PSV 4 obtained in Synthesis Example 4 to prepare a coating film forming composition (hereinafter, abbreviated as "PSV 4-BLys"). The coating film forming composition (PSV 4-BLys) was spin-coated and was baked at 250° C. for 5 minutes. The coating film after baking was pared off and the resultant sample piece was subjected to an FT-IR spectrum measurement by a KBr method.

Example 43

In the same manner as in Example 1, Boc-His was added to the polysiloxane vanish PSV 4 obtained in Synthesis Example 4 to prepare a coating film forming composition (hereinafter, abbreviated as "PSV 4-BHis"). The coating film forming composition (PSV 4-BHis) was spin-coated and was baked at 250° C. for 5 minutes. The coating film after baking was pared off and the resultant sample piece was subjected to an FT-IR spectrum measurement by a KBr method.

Comparative Example 28

The polysiloxane vanish PSV 2 obtained in Synthesis Example 2 and used as the coating film forming composition was spin-coated and was baked at 250° C. for 5 minutes. The coating film after baking was pared off and the resultant sample piece was subjected to an FT-IR spectrum measurement by a KBr method.

Comparative Example 29

The polysiloxane vanish PSV 2 obtained in Synthesis Example 2 and used as the coating film forming composition was spin-coated and was baked at 400° C. for 5 minutes. The coating film after baking was pared off and the resultant sample piece was subjected to an FT-IR spectrum measurement by a KBr method.

Comparative Example 30

The polysiloxane vanish PSV 3 obtained in Synthesis Example 3 and used as the coating film forming composition was spin-coated and was baked at 250° C. for 5 minutes. The coating film after baking was pared off and the resultant sample piece was subjected to an FT-IR spectrum measurement by a KBr method.

Comparative Example 31

The polysiloxane vanish PSV 3 obtained in Synthesis Example 3 and used as the coating film forming composition was spin-coated and was baked at 400° C. for 5 minutes. The coating film after baking was pared off and the resultant sample piece was subjected to an FT-IR spectrum measurement by a KBr method.

Comparative Example 32

The polysiloxane vanish PSV 4 obtained in Synthesis Example 4 and used as the coating film forming composition was spin-coated and was baked at 250° C. for 5 minutes. The coating film after baking was pared off and the resultant sample piece was subjected to an FT-IR spectrum measurement by a KBr method.

Comparative Example 33

The polysiloxane vanish PSV 4 obtained in Synthesis Example 4 and used as the coating film forming composition was spin-coated and was baked at 400° C. for 5 minutes. The coating film after baking was pared off and the resultant sample piece was subjected to an FT-IR spectrum measurement by a KBr method.

The results of Examples 35 to 37 and Comparative Examples 28 and 29 are shown in FIGS. 17 to 19 and FIGS. 37 and 38; the results of Examples 38 to 40 and Comparative Examples 30 and 31 are shown in FIGS. 20 to 22 and FIGS. 39 and 40; and the results of Examples 41 to 43 and Comparative Examples 32 and 33 are shown in FIGS. 23 to 25 and FIGS. 41 and 42.

As shown in FIGS. 17 to 25, it was found that a film obtained from a coating film forming composition in which arginine, histidine, or lysine having particularly high ability of accelerating the condensation-polymerization of the polysiloxane as the amino acid generator was added to a polysiloxane vanish is effective for digesting the Si—OH bond also with respect to the polysiloxane vanishes PSV 2 to 4 just like with respect to PSV 1. This result indicates that all of the polysiloxane vanish PSV 1 synthesized from a tetrafunctional silane monomer (hydrolyzable silane monomer having four hydrolyzable groups), the polysiloxane vanish PSV 2 obtained by copolymerizing a tetrafunctional silane monomer (hydrolyzable silane monomer having four hydrolyzable groups) with a trifunctional silane monomer (hydrolyzable silane monomer having three hydrolyzable groups), the polysiloxane vanish PSV 3 obtained by copolymerizing a tetrafunctional silane monomer (hydrolyzable silane monomer having four hydrolyzable groups), a trifunctional silane monomer (hydrolyzable silane monomer having three hydrolyzable groups), and a bifunctional silane monomer (hydrolyzable silane monomer having two hydrolyzable groups), and the polysiloxane vanish PSV 4 synthesized from a trifunctional silane monomer (hydrolyzable silane monomer having three hydrolyzable groups) has the effect, so that a general polysiloxane polymer can digest the Si—OH bond at a low baking temperature.

In the case of a coating film forming composition produced from a polysiloxane vanish containing no amino acid generator, it was found that when a film containing PSV 2 and containing no amino acid generator is baked at 400° C. for 5 minutes, Si—OH bonds remain; and the number of Si—OH bonds in a film containing PSV 3 and containing no amino acid generator does not become the same number as the number of Si—OH bonds of a film containing an amino acid generator baked at 250° C. for 5 minutes, until the film containing PSV 3 and containing no amino acid generator is baked at 400° C. for 5 minutes.

[Effect after Solvent-Exchange]

It was investigated whether the same effect can be obtained by adding the amino acid generator to a polysiloxane vanish after the solvent-exchange in the polysiloxane vanish during the synthesis of the polysiloxane vanishes obtained in Synthesis Examples 1 to 4.

The film formation was performed by a spin coating method under conditions of at 2,000 rpm and for 20 seconds. The coating film forming composition was spin-coated and was baked in the air using a hot plate as baking equipment.

The film thickness was set to 500 nm. As the base material, a 4-inch silicon wafer was used.

Example 44

To the polysiloxane vanish PSV 1 obtained in Synthesis Example 1, 94.84 g of propylene glycol monomethyl ether acetate (hereinafter, abbreviated as "PGMEA") that is the same amount of ethanol used as the solvent during the hydrolysis and condensation reactions of PGMEA was added and then, using an evaporator, the solvent-exchange was performed under conditions of at 20° C. of a water bath temperature and under reduced pressure for 6 hours.

To the obtained polysiloxane vanish after the solvent-exchange, Boc-Arg was added in the same manner as in Example 1 to obtain a coating film forming composition (hereinafter, abbreviated as "PSV 1-BArg-PGMEA").

The obtained coating film forming composition (PSV 1-BArg-PGMEA) was spin-coated and was baked at 250° C. for 5 minutes. The coating film after baking was pared off and the resultant sample piece was subjected to an FT-IR spectrum measurement by a KBr method.

Example 45

The polysiloxane vanish PSV 2 obtained in Synthesis Example 2 was subjected to the solvent-exchange to PGMEA in the same manner as in Example 44 and thereto, Boc-Arg was added.

The resultant coating film forming composition (hereinafter, abbreviated as "PSV t-Boc-Arg-PGMEA") was spin-coated and was baked at 250° C. for 5 minutes. The coating film after baking was pared off and the resultant sample piece was subjected to an FT-IR spectrum measurement by a KBr method.

Example 46

The polysiloxane vanish PSV 3 obtained in Synthesis Example 3 was subjected to the solvent-exchange to PGMEA in the same manner as in Example 44 and thereto, Boc-Arg was added.

The resultant coating film forming composition (hereinafter, abbreviated as "PSV 3-Boc-Arg-PGMEA") was spin-coated and was baked at 250° C. for 5 minutes. The coating film after baking was pared off and the resultant sample piece was subjected to an FT-IR spectrum measurement by a KBr method.

Example 47

The polysiloxane vanish PSV 4 obtained in Synthesis Example 4 was subjected to the solvent-exchange to PGMEA in the same manner as in Example 44 and thereto, Boc-Arg was added.

The obtained coating film forming composition (hereinafter, abbreviated as "PSV 4-Boc-Arg-PGMEA") was spin-coated and was baked at 250° C. for 5 minutes. The coating film after baking was pared off and the resultant sample piece was subjected to an FT-IR spectrum measurement by a KBr method.

Comparative Example 34

To the polysiloxane vanish PSV 1 obtained in Synthesis Example 1, 94.84 g of PGMEA that is the same amount of ethanol used as the solvent during the hydrolysis and condensation reactions to PGMEA was added and then, using an evaporator, the solvent-exchange was performed under conditions of at 20° C. of a water bath temperature and under reduced pressure for 6 hours.

The obtained coating film forming composition (hereinafter, abbreviated as "PSV 1-PGMEA) after the solvent-exchange was spin-coated and was baked at 250° C. for 5 minutes. The coating film after baking was pared off and the resultant sample piece was subjected to an FT-IR spectrum measurement by a KBr method.

Comparative Example 35

The polysiloxane vanish PSV 2 obtained in Synthesis Example 2 was subjected to the solvent-exchange to PGMEA in the same manner as in Comparative Example 34.

The obtained coating film forming composition (hereinafter, abbreviated as "PSV 2-PGMEA") was spin-coated and was baked at 250° C. for 5 minutes. The coating film after baking was pared off and the resultant sample piece was subjected to an FT-IR spectrum measurement by a KBr method.

Comparative Example 36

The polysiloxane vanish PSV 3 obtained in Synthesis Example 3 was subjected to the solvent-exchange to PGMEA in the same manner as in Comparative Example 34.

The obtained coating film forming composition (hereinafter, abbreviated as "PSV 3-PGMEA") was spin-coated and was baked at 250° C. for 5 minutes. The coating film after baking was pared off and the resultant sample piece was subjected to an FT-IR spectrum measurement by a KBr method.

Comparative Example 37

The polysiloxane vanish PSV 4 obtained in Synthesis Example 4 was subjected to the solvent-exchange to PGMEA in the same manner as in Comparative Example 34.

The obtained coating film forming composition (hereinafter, abbreviated as "PSV 3-PGMEA") was spin-coated and was baked at 250° C. for 5 minutes. The coating film after baking was pared off and the resultant sample piece was subjected to an FT-IR spectrum measurement by a KBr method.

The results of Examples 44 to 47 and Comparative Examples 34 to 37 are shown in FIGS. 26 to 29 and FIGS. 43 to 46.

As shown in FIGS. 26 to 29, also in a polysiloxane vanish in which the solvent of the polysiloxane vanish is solvent-exchanged from ethanol that is the solvent used during the hydrolysis and condensation reactions to PGMEA, the effect of the amino acid generator was developed, so that it was found that even when a different solvent type is used, the Si—OH bond in the film can be remarkably digested.

As described above, from the above results, it could be confirmed that a polysiloxane composition in which an amino acid generator is added to a polysiloxane vanish can maintain advantageous preservation stability of the polysiloxane vanish, can accelerate the condensation-polymerization during baking, and can remarkably reduce remaining Si—OH bonds, so that such a polysiloxane composition is effective as the coating film forming composition.

[Behavior of Reducing Si—OH Bonds According to Exposure Conditions]

A coating film forming composition was produced using a polysiloxane vanish containing a photo amino acid generator, and the variation in the behavior of reducing Si—OH bonds according to the variation in the exposure conditions when a coating film is produced by coating a substrate with the coating film forming composition, was confirmed.

The production of a film was performed by spin-coating a substrate (base material) with the coating film forming composition under conditions of at 2,000 rpm and for 20 seconds. The coating film forming composition was spin-coated and subjected to drying at room temperature (about 20° C.) to remove the solvent in the composition and to exposure in the air using a UV irradiation apparatus in an exposure amount of 1 J/cm$^2$ (converted into energy at 250 nm). The film thickness was set at 500 nm. As the base material, a 4-inch silicon wafer was used.

Example 48

The coating film forming composition (PSV 1-BAla) obtained in Example 1 was spin-coated and was subjected to drying at room temperature to remove the solvent and to a 1 J/cm$^2$ of exposure. The coating film after exposure was pared off and the resultant sample piece was subjected to an FT-IR spectrum measurement by a KBr method.

Example 49

In the same manner as in Example 48, except that the coating film forming composition (PSV 1-BArg) obtained in Example 2 was used, the coating film was formed and a sample piece thereof was subjected to an FT-IR spectrum measurement.

Example 50

In the same manner as in Example 48, except that the coating film forming composition (PSV 1-BAsp) obtained in Example 3 was used, the coating film was formed and a sample piece thereof was subjected to an FT-IR spectrum measurement.

Example 51

In the same manner as in Example 48, except that the coating film forming composition (PSV 1-BGly) obtained in Example 4 was used, the coating film was formed and a sample piece thereof was subjected to an FT-IR spectrum measurement.

Example 52

In the same manner as in Example 48, except that the coating film forming composition (PSV 1-BHis) obtained in Example 5 was used, the coating film was formed and a sample piece thereof was subjected to an FT-IR spectrum measurement.

Example 53

In the same manner as in Example 48, except that the coating film forming composition (PSV 1-BLys) obtained in Example 6 was used, the coating film was formed and a sample piece thereof was subjected to an FT-IR spectrum measurement by a KBr method.

Example 54

In the same manner as in Example 48, except that the coating film forming composition (PSV 1-FBArg) obtained in Example 7 was used, the coating film was formed and a sample piece thereof was subjected to an FT-IR spectrum measurement.

Example 55

In the same manner as in Example 48, except that the coating film forming composition (PSV 1-FBOrn) obtained in Example 8 was used, the coating film was formed and a sample piece thereof was subjected to an FT-IR spectrum measurement.

Example 56

In the same manner as in Example 48, except that the coating film forming composition (PSV 1-FFOrn) obtained in Example 9 was used, the coating film was formed and a sample piece thereof was subjected to an FT-IR spectrum measurement.

Comparative Example 38

The polysiloxane vanish (PSV 1) obtained in Synthesis Example 1 was spin-coated and then subjected to drying at room temperature to remove the solvent and not subjected to exposure. The coating film after drying was pared off and the resultant sample piece was subjected to an FT-IR spectrum measurement by a KBr method.

Comparative Example 39

The polysiloxane vanish (PSV 1) obtained in Synthesis Example 1 and used as the coating film forming composition was spin-coated and then subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 40

The polysiloxane vanish (PSV 1) obtained in Synthesis Example 1 and used as the coating film forming composition was spin-coated and then subjected to drying at room temperature to remove the solvent, which was then subjected to exposure in the air using a UV irradiation apparatus in an exposure amount of 2 J/cm$^2$ (converted into energy at 250 nm). The coating film after exposure was pared off and the resultant sample piece was subjected to an FT-IR spectrum measurement by a KBr method.

Comparative Example 41

The polysiloxane vanish (PSV 1) obtained in Synthesis Example 1 and used as the coating film forming composition was spin-coated and then subjected to drying at room temperature to remove the solvent, which was then subjected to exposure in the air using a UV irradiation apparatus in an exposure amount of 5 J/cm² (converted into energy at 250 nm). The coating film after exposure was pared off and the resultant sample piece was subjected to an FT-IR spectrum measurement by a KBr method.

Comparative Example 42

The polysiloxane vanish (PSV 1) obtained in Synthesis Example 1 and used as the coating film forming composition was spin-coated and then subjected to drying at room temperature to remove the solvent, which was then subjected to exposure in the air using a UV irradiation apparatus in an exposure amount of 10 J/cm² (converted into energy at 250 nm). The coating film after exposure was pared off and the resultant sample piece was subjected to an FT-IR spectrum measurement by a KBr method.

The results of the FT-IR measurement in Examples 48 to 56 and Comparative Examples 38 to 42 are shown in FIGS. 47 to 55 and FIGS. 76 to 80. In the figures, there was focused attention on a peak at around 3,500 cm$^{-1}$ ascribed to an OH stretching vibration of a Si—OH bond.

In FIGS. 47 to 55, the number of Si—OH bonds of a film produced by subjecting to a 1 J/cm² exposure, the film formed from a coating film forming composition in which a photo amino acid generator was added to the polysiloxane vanish (PSV 1), was reduced. In the cases of arginine and ornithine used in Examples 49, 54, and 56 among the photo amino acid generators, it was confirmed that the photo amino acid generator is effective for reducing the peak for the Si—OH bond.

In a film formed from as the coating film forming composition, the polysiloxane vanish (PSV 1) in Comparative Example 38, extremely many Si—OH bonds remained, and it was found that as in Comparative Examples 39 to 42, even by enlarging the exposure amount, the Si—OH bond did not disappear.

[Behavior of Reducing Si—OH Bonds According to Exposure Amount]

There was confirmed the exposure amount dependency of the behavior of reducing Si—OH bonds when Boc-Arg most effective for reducing Si—OH bonds was used as the photo amino acid generator.

The film formation was performed by a spin coating method under conditions of at 2,000 rpm and for 20 seconds. The coating film forming composition was spin-coated and was subjected to drying at room temperature to remove the solvent, which was then subjected to exposure in the air using a UV irradiation apparatus as an exposure apparatus. The film thickness was set to 500 nm. As the base material, a 4-inch silicon wafer was used.

Example 57

The coating film forming composition (PSV 1-BArg) obtained in Example 2 was spin-coated and was subjected to drying at room temperature to remove the solvent, which was then subjected to exposure in the air using a UV irradiation apparatus in an exposure amount of 100 mJ/cm² (converted into energy at 250 nm). The coating film after exposure was pared off and the resultant sample piece was subjected to an FT-IR spectrum measurement by a KBr method.

Example 58

The coating film forming composition (PSV 1-BArg) obtained in Example 2 was spin-coated and was subjected to drying at room temperature to remove the solvent, which was then subjected to exposure in the air using a UV irradiation apparatus in an exposure amount of 200 mJ/cm² (converted into energy at 250 nm). The coating film after exposure was pared off and the resultant sample piece was subjected to an FT-IR spectrum measurement by a KBr method.

Example 59

The coating film forming composition (PSV 1-BArg) obtained in Example 2 was spin-coated and was subjected to drying at room temperature to remove the solvent, which was then subjected to exposure in the air using a UV irradiation apparatus in an exposure amount of 500 mJ/cm² (converted into energy at 250 nm). The coating film after exposure was pared off and the resultant sample piece was subjected to an FT-IR spectrum measurement by a KBr method.

Comparative Example 43

The polysiloxane vanish (PSV 1) obtained in Synthesis Example 1 and used as the coating film forming composition was spin-coated and was subjected to drying at room temperature to remove the solvent, which was then subjected to exposure in the air using a UV irradiation apparatus in an exposure amount of 100 mJ/cm² (converted into energy at 250 nm). The coating film after exposure was pared off and the resultant sample piece was subjected to an FT-IR spectrum measurement by a KBr method.

Comparative Example 44

The polysiloxane vanish (PSV 1) obtained in Synthesis Example 1 and used as the coating film forming composition was spin-coated and was subjected to drying at room temperature to remove the solvent, which was then subjected to exposure in the air using an UV irradiation apparatus in an exposure amount of 200 mJ/cm² (converted into energy at 250 nm). The coating film after exposure was pared off and the resultant sample piece was subjected to an FT-IR spectrum measurement by a KBr method.

Comparative Example 45

The polysiloxane vanish (PSV 1) obtained in Synthesis Example 1 and used as the coating film forming composition was spin-coated and was subjected to drying at room temperature to remove the solvent, which was then subjected to exposure in the air using an UV irradiation apparatus in an exposure amount of 500 mJ/cm² (converted into energy at 250 nm). The coating film after exposure was pared off and the resultant sample piece was subjected to an FT-IR spectrum measurement by a KBr method.

The results of Example 49 and Examples 57 to 59 are shown in FIG. 48 and FIGS. 56 to 58 and the results of Comparative Example 38 and Comparative Examples 43 to 45 are shown in FIG. 76 and FIGS. 81 to 83.

Figure 48:
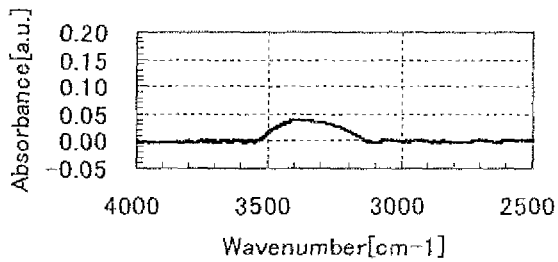
FIG. 48 is a graph showing an FT-IR spectrum of the film obtained in Example 49.
Figure 49:
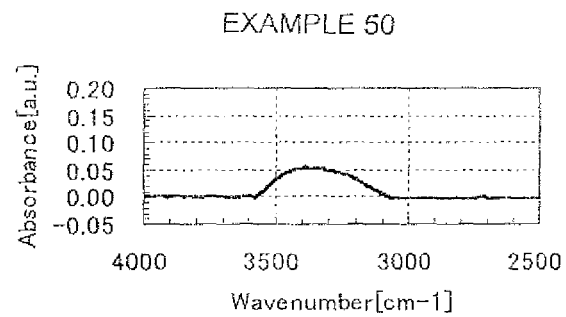
FIG. 49 is a graph showing an FT-IR spectrum of the film obtained in Example 50.
Figure 50:
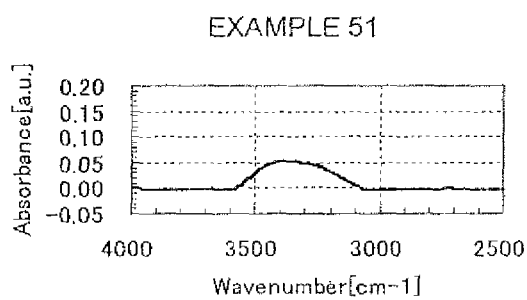
FIG. 50 is a graph showing an FT-IR spectrum of the film obtained in Example 51.
Figure 51:
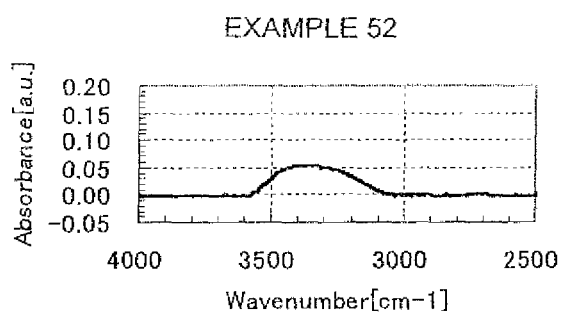
FIG. 51 is a graph showing an FT-IR spectrum of the film obtained in Example 52.
Figure 52:
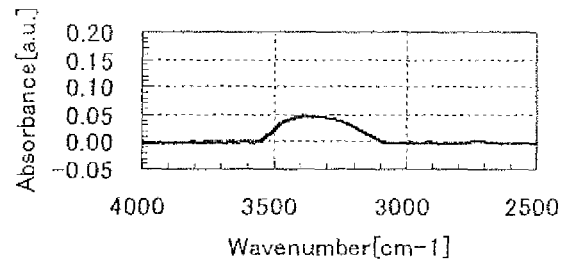
FIG. 52 is a graph showing an FT-IR spectrum of the film obtained in Example 53.
Figure 53:
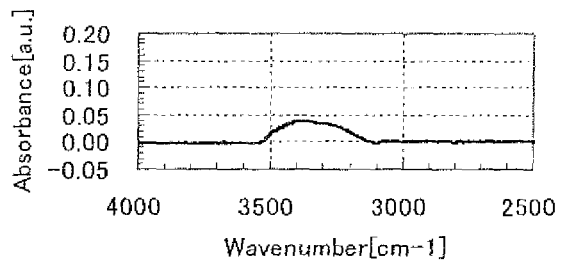
FIG. 53 is a graph showing an FT-IR spectrum of the film obtained in Example 54
Figure 54:
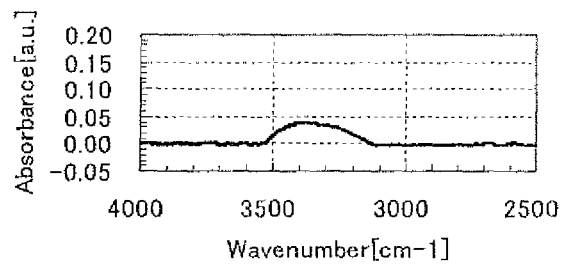
FIG. 54 is a graph showing an FT-IR spectrum of the film obtained in Example 55.
Figure 55:
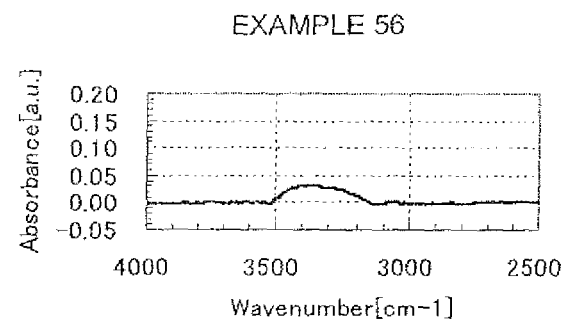
FIG. 55 is a graph showing an FT-IR spectrum of the film obtained in Example 56.
Figure 56:
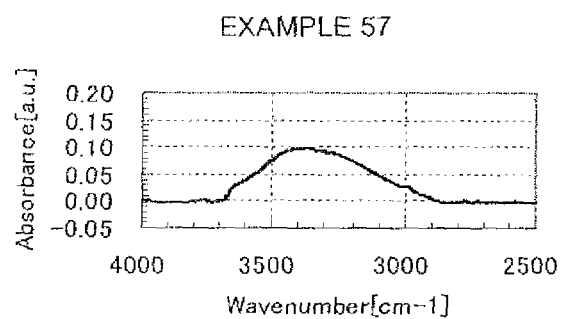
FIG. 56 is a graph showing an FT-IR spectrum of the film obtained in Example 57.
Figure 57:
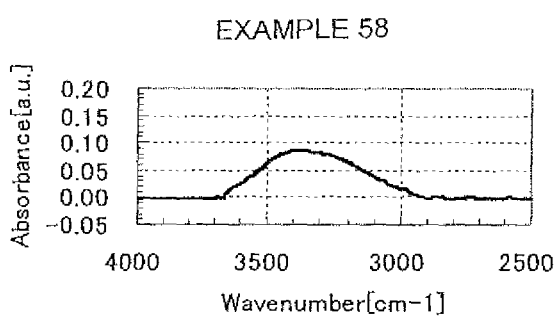
FIG. 57 is a graph showing an FT-IR spectrum of the film obtained in Example 58.
Figure 58:
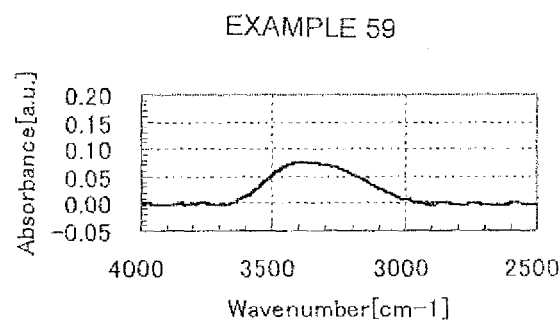
FIG. 58 is a graph showing an FT-IR spectrum of the film obtained in Example 59.
Figure 59:
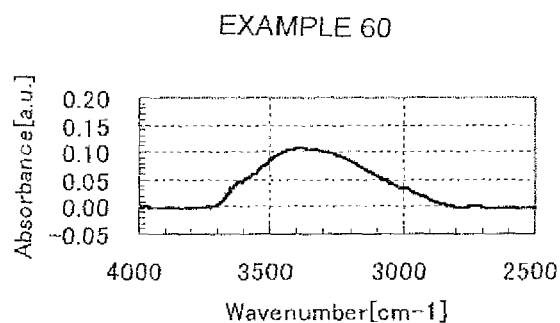
FIG. 59 is a graph showing an FT-IR spectrum of the film obtained in Example 60.
Figure 60:
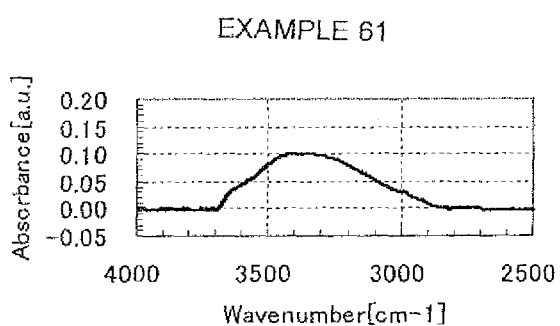
FIG. 60 is a graph showing an FT-IR spectrum of the film obtained in Example 61.

From the results in FIG. 48 and FIG. 54, it was found that a film obtained by coating a base material with a coating film forming composition produced by adding Boc-Arg as the amino acid generator to a polysiloxane vanish is effective for reducing Si—OH bonds in an exposure amount of 500 m J/cm² or more.

On the contrary, as the exposure amount dependency of the behavior of reducing Si—OH bonds of a film obtained by coating a base material solely with the polysiloxane vanish (PSV 1) as the coating film forming composition, it was confirmed that it is not effective for reducing Si—OH bonds to enlarge the exposure amount.

[Behavior of Reducing Si—OH Bonds According to Adding Amount of Photo Amino Acid Generator]

There was confirmed the adding amount dependency of the behavior of reducing Si—OH bonds when Boc-Arg most effective for reducing Si—OH bonds was used as the photo amino acid generator.

The film formation was performed by a spin coating method under conditions of at 2,000 rpm and for 20 seconds. The coating film forming composition was spin-coated and was subjected to drying at room temperature to remove the solvent, which was then subjected to exposure in the air using a UV irradiation apparatus as an exposure apparatus.

The film thickness was set to 500 nm. As the base material, a 4-inch silicon wafer was used.

Example 60

In the same manner as in Example 2, except that Boc-Arg was added to the polysiloxane vanish in an amount of 0.1 phr (that is, the composition contains Boc-Arg in an amount of 0.1 parts by mass relative to 100 parts by mass of $SiO_2$ in the polysiloxane vanish PSV 1), a coating film forming composition (hereinafter, abbreviated as "PSV 1-BArg-0.1 phr") was prepared. The obtained coating film forming composition (PSV 1-BArg-0.1 phr) was spin-coated and was subjected to drying at room temperature to remove the solvent, which was then subjected to exposure in the air using a UV irradiation apparatus in an exposure amount of 1 $J/cm^2$ (converted into energy at 250 nm). The coating film after exposure was pared off and the resultant sample piece was subjected to an FT-IR spectrum measurement by a KBr method.

Example 61

In the same manner as in Example 2, except that Boc-Arg was added to the polysiloxane vanish in an amount of 0.5 phr (that is, the composition contains Boc-Arg in an amount of 0.5 parts by mass relative to 100 parts by mass of $SiO_2$ in the polysiloxane vanish PSV 1), a coating film forming composition (hereinafter, abbreviated as "PSV 1-BArg-0.5 phr") was prepared. The obtained coating film forming composition (PSV 1-BArg-0.5 phr) was spin-coated and was subjected to drying at room temperature to remove the solvent, which was then subjected to exposure in the air using a UV irradiation apparatus in an exposure amount of 1 $J/cm^2$ (converted into energy at 250 nm). The coating film after exposure was pared off and the resultant sample piece was subjected to an FT-IR spectrum measurement by a KBr method.

Example 62

In the same manner as in Example 2, except that Boc-Arg was added to the polysiloxane vanish in an amount of 1.0 phr (that is, the composition contains Boc-Arg in an amount of 1.0 part by mass relative to 100 parts by mass of $SiO_2$ in the polysiloxane vanish PSV 1), a coating film forming composition (hereinafter, abbreviated as "PSV 1-BArg-1.0 phr") was prepared. The obtained coating film forming composition (PSV 1-BArg-1.0 phr) was spin-coated and was subjected to drying at room temperature to remove the solvent, which was then subjected to exposure in the air using an UV irradiation apparatus in an exposure amount of 1 $J/cm^2$ (converted into energy at 250 nm). The coating film after exposure was pared off and the resultant sample piece was subjected to an FT-IR spectrum measurement by a KBr method.

Example 63

In the same manner as in Example 2, except that Boc-Arg was added to the polysiloxane vanish in an amount of 2.5 phr (that is, the composition contains Boc-Arg in an amount of 2.5 parts by mass relative to 100 parts by mass of $SiO_2$ in the polysiloxane vanish PSV 1), a coating film forming composition (hereinafter, abbreviated as "PSV 1-BArg-2.5 phr") was prepared. The obtained coating film forming composition (PSV 1-BArg-2.5 phr) was spin-coated and was subjected to drying at room temperature to remove the solvent, which was then subjected to exposure in the air using an UV irradiation apparatus in an exposure amount of 1 $J/cm^2$ (converted into energy at 250 nm). The coating film after exposure was pared off and the resultant sample piece was subjected to an FT-IR spectrum measurement by a KBr method.

The results of Example 49 and Examples 60 to 62 are shown in FIG. 48 and FIGS. 59 to 62.

Figure 61:
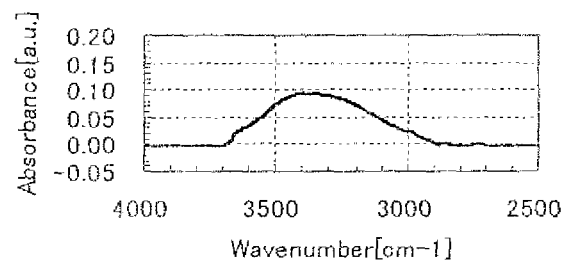
FIG. 61 is a graph showing an FT-IR spectrum of the film obtained in Example 62.
Figure 62:
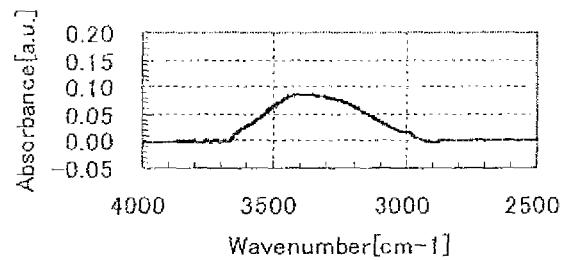
FIG. 62 is a graph showing an FT-IR spectrum of the film obtained in Example 63.
Figure 63:
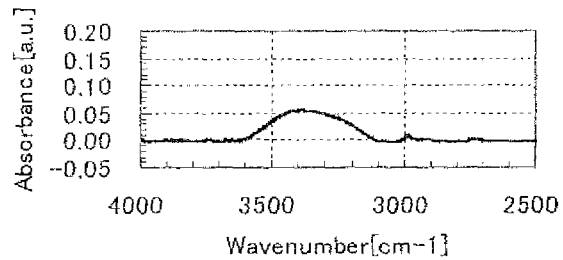
FIG. 63 is a graph showing an FT-IR spectrum of the film obtained in Example 64.
Figure 64:
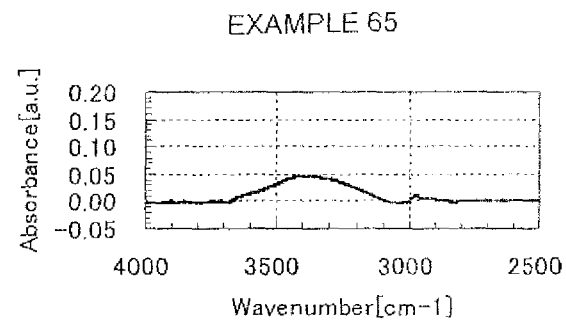
FIG. 64 is a graph showing an FT-IR spectrum of the film obtained in Example 65.
Figure 65:
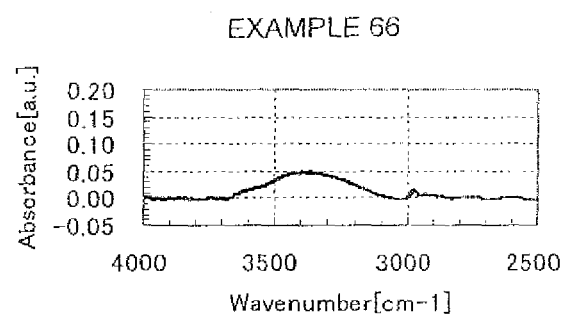
FIG. 65 is a graph showing an FT-IR spectrum of the film obtained in Example 66.
Figure 66:
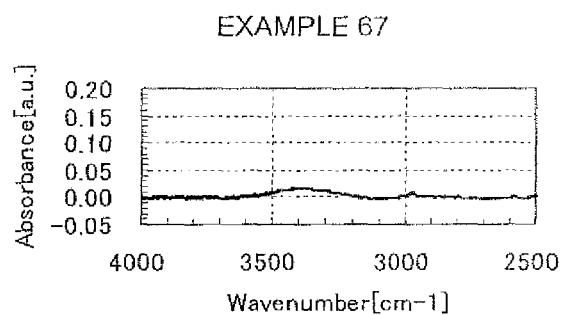
FIG. 66 is a graph showing an FT-IR spectrum of the film obtained in Example 67.
Figure 67:
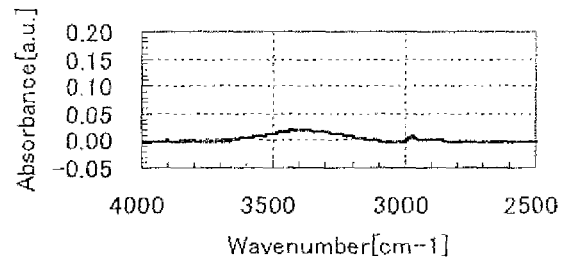
FIG. 67 is a graph showing an FT-IR spectrum of the film obtained in Example 68.
Figure 68:
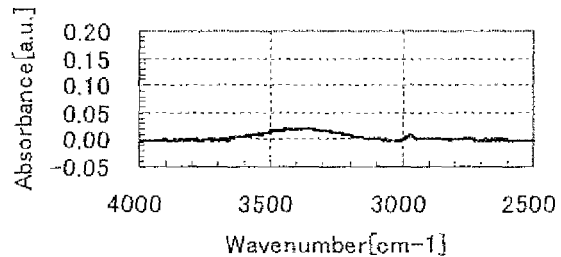
FIG. 68 is a graph showing an FT-IR spectrum of the film obtained in Example 69.
Figure 69:
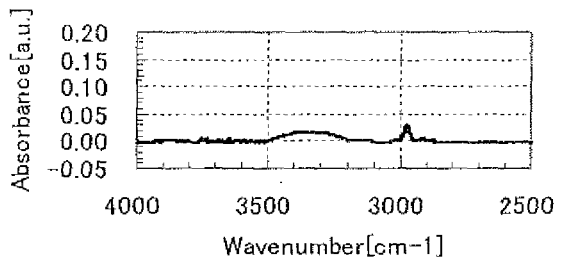
FIG. 69 is a graph showing an FT-IR spectrum of the film obtained in Example 70.
Figure 70:
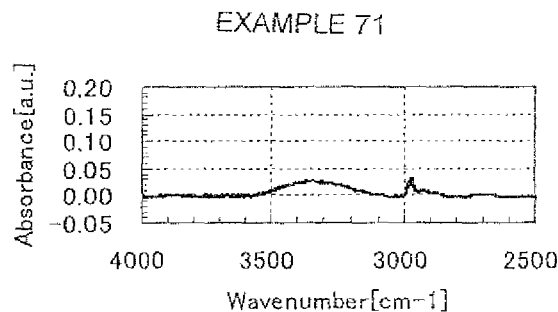
FIG. 70 is a graph showing an FT-IR spectrum of the film obtained in Example 71.
Figure 71:
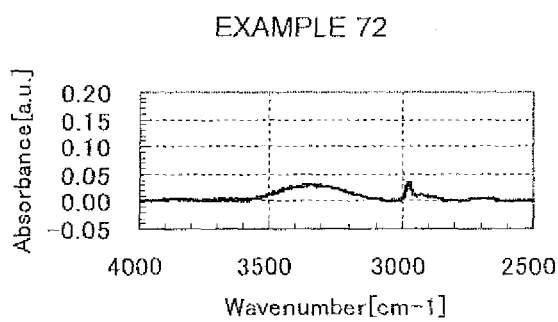
FIG. 71 is a graph showing an FT-IR spectrum of the film obtained in Example 72.
Figure 72:
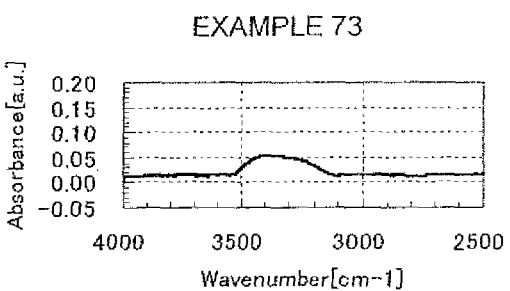
FIG. 72 is a graph showing an FT-IR spectrum of the film obtained in Example 73.
Figure 73:
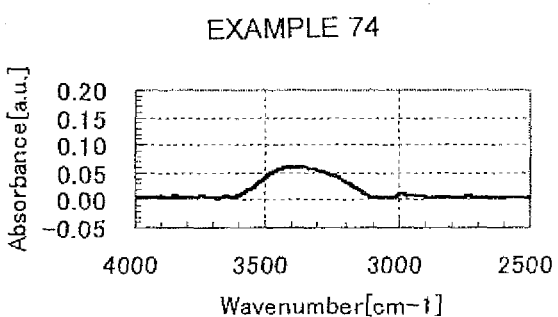
FIG. 73 is a graph showing an FT-IR spectrum of the film obtained in Example 74.
Figure 74:
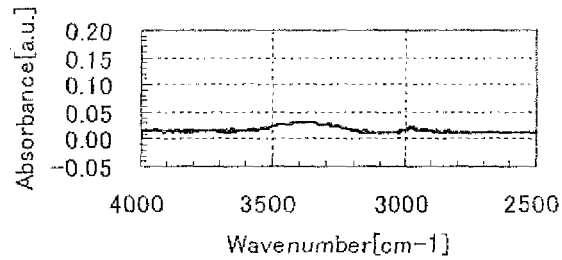
FIG. 74 is a graph showing an FT-IR spectrum of the film obtained in Example 75.
Figure 75:
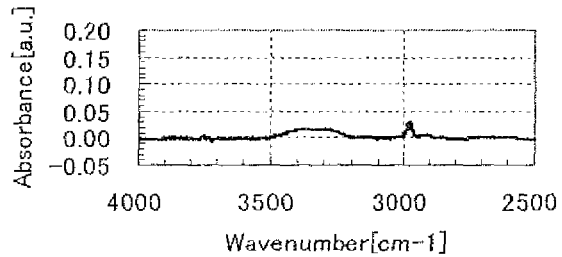
FIG. 75 is a graph showing an FT-IR spectrum of the film obtained in Example 76.
Figure 76:
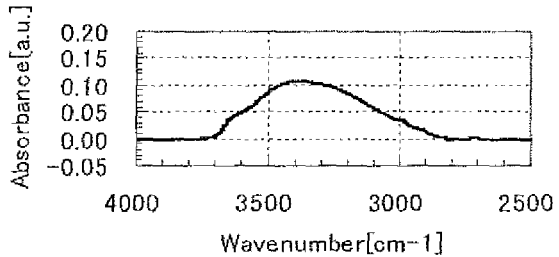
FIG. 76 is a graph showing an FT-IR spectrum of the film obtained in Comparative Example 38.
Figure 77:
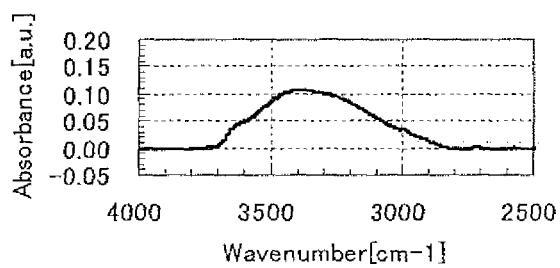
FIG. 77 is a graph showing an FT-IR spectrum of the film obtained in Comparative Example 39.
Figure 78:
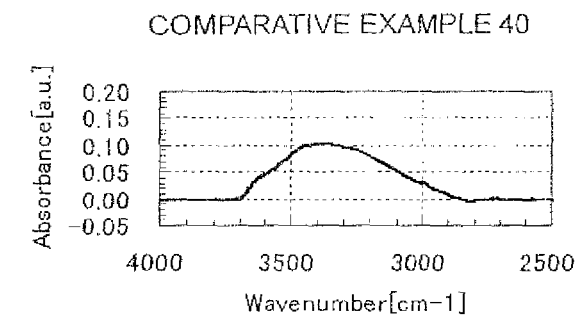
FIG. 78 is a graph showing an FT-IR spectrum of the film obtained in Comparative Example 40.
Figure 79:
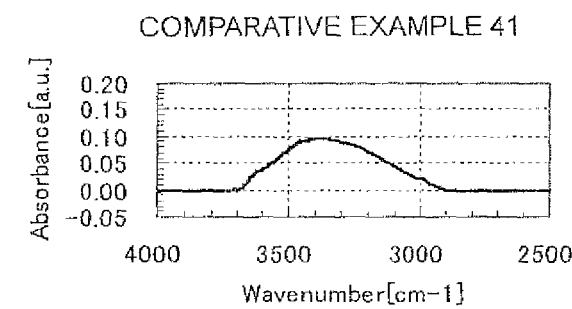
FIG. 79 is a graph showing an FT-IR spectrum of the film obtained in Comparative Example 41.
Figure 80:
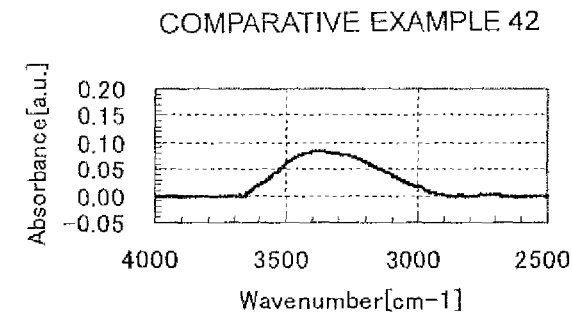
FIG. 80 is a graph showing an FT-IR spectrum of the film obtained in Comparative Example 42.
Figure 81:
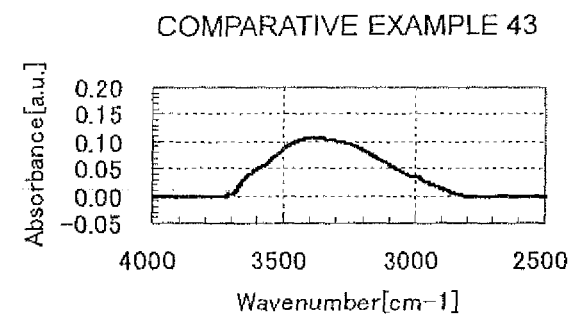
FIG. 81 is a graph showing an FT-IR spectrum of the film obtained in Comparative Example 43.
Figure 82:
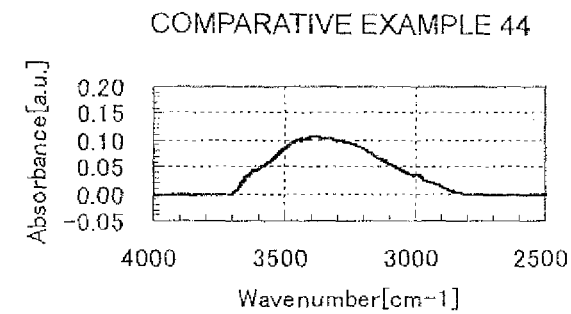
FIG. 82 is a graph showing an FT-IR spectrum of the film obtained in Comparative Example 44.
Figure 83:
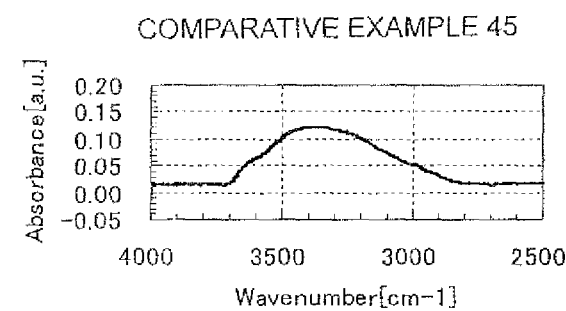
FIG. 83 is a graph showing an FT-IR spectrum of the film obtained in Comparative Example 45.
Figure 84:
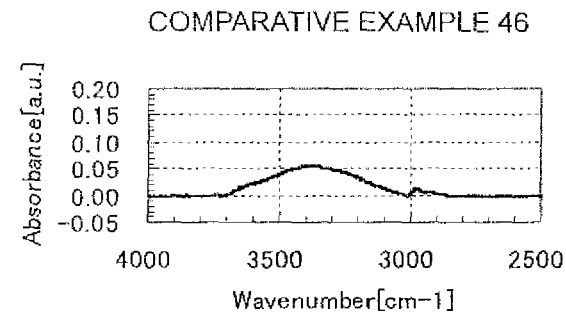
FIG. 84 is a graph showing an FT-IR spectrum of the film obtained in Comparative Example 46.
Figure 85:
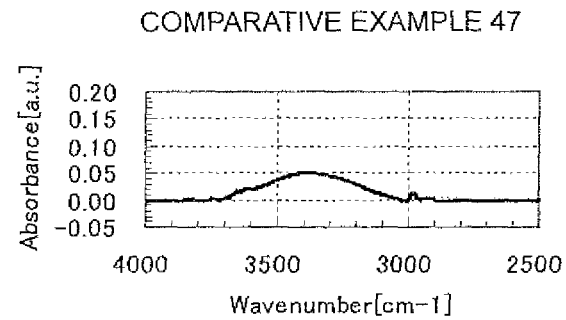
FIG. 85 is a graph showing an FT-IR spectrum of the film obtained in Comparative Example 47.
Figure 86:
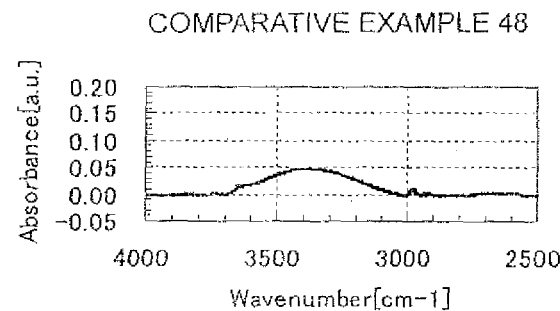
FIG. 86 is a graph showing an FT-IR spectrum of the film obtained in Comparative Example 48.
Figure 87:
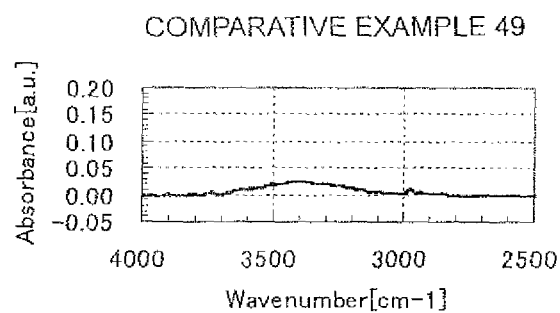
FIG. 87 is a graph showing an FT-IR spectrum of the film obtained in Comparative Example 49.
Figure 88:
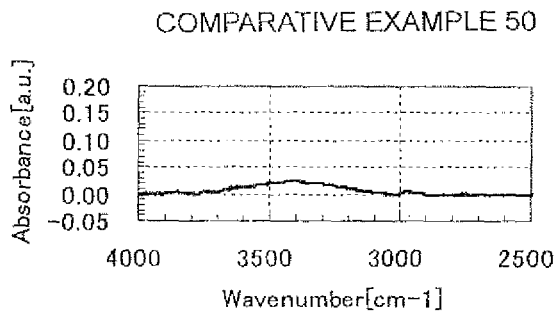
FIG. 88 is a graph showing an FT-IR spectrum of the film obtained in Comparative Example 50.
Figure 89:
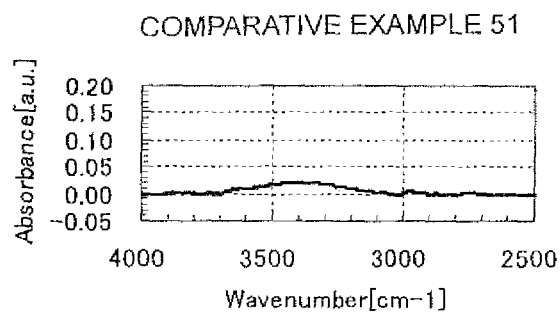
FIG. 89 is a graph showing an FT-IR spectrum of the film obtained in Comparative Example 51.
Figure 90:
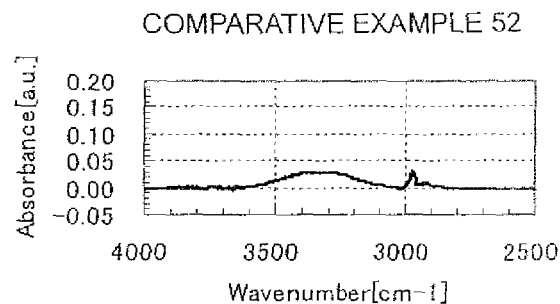
FIG. 90 is a graph showing an FT-IR spectrum of the film obtained in Comparative Example 52.
Figure 91:
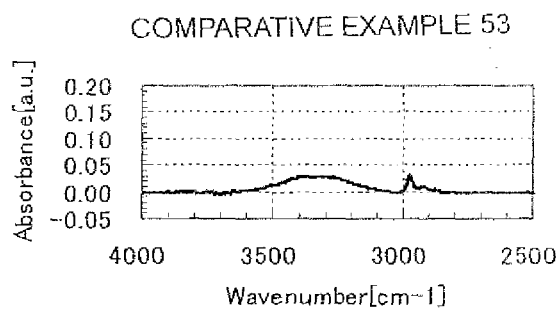
FIG. 91 is a graph showing an FT-IR spectrum of the film obtained in Comparative Example 53.
Figure 92:
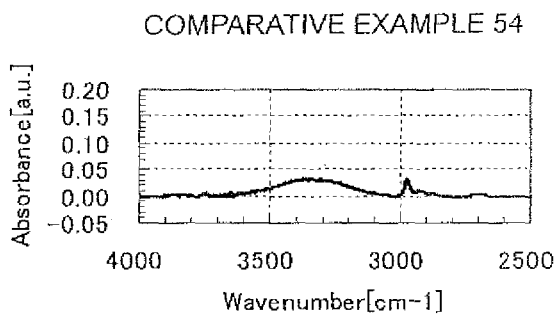
FIG. 92 is a graph showing an FT-IR spectrum of the film obtained in Comparative Example 54.
Figure 93:
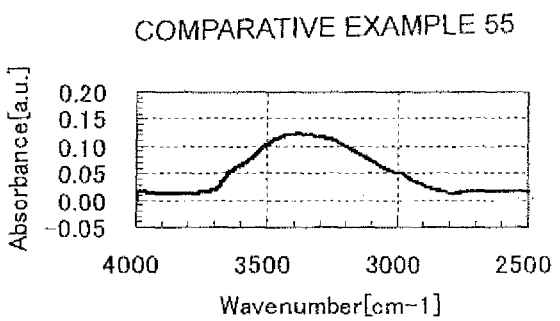
FIG. 93 is a graph showing an FT-IR spectrum of the film obtained in Comparative Example 55.
Figure 94:
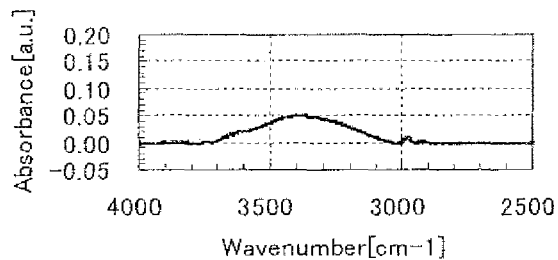
FIG. 94 is a graph showing an FT-IR spectrum of the film obtained in Comparative Example 56.
Figure 95:
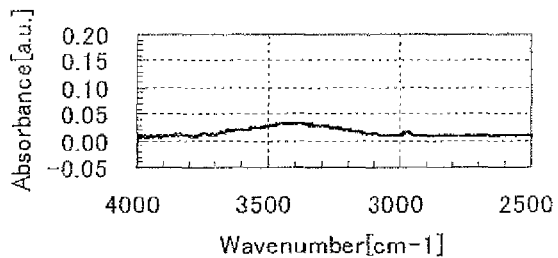
FIG. 95 is a graph showing an FT-IR spectrum of the film obtained in Comparative Example 57.
Figure 96:
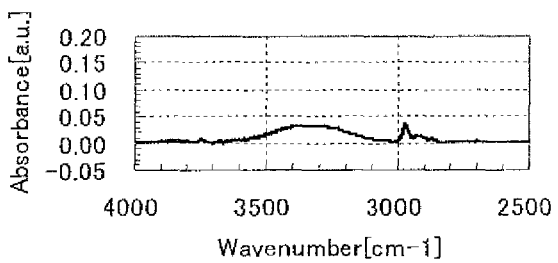
FIG. 96 is a graph showing an FT-IR spectrum of the film obtained in Comparative Example 58.

As shown in FIG. 48, FIG. 61, and FIG. 62, from the results of the FT-IR measurement of films produced using coating film forming compositions in which the adding amount of Boc-Arg most effective for reducing Si—OH bonds to the polysiloxane vanish was varied, it was found that a composition in which 1.0 phr of Boc-Arg was added developed no effect for reducing Si—OH bonds; however, a composition in which 2.5 phr or more of Boc-Arg was added developed the effect for reducing Si—OH bonds, so that the composition in which 2.5 phr or more of Boc-Arg is added is effective for reducing Si—OH bonds.

With a remarkably small amount of 2.5 phr, the effect can be developed, so that the number of Si—OH bonds can be dramatically reduced without largely changing the property of the polysiloxane.

[Behavior of Reducing Si—OH Bonds According to Baking Conditions of Polysiloxane Produced by Copolymerization]

It was investigated whether Si—OH bonds can be reduced by using the photo amino acid generator also with respect to a polysiloxane vanish produced by copolymerization.

The film formation was performed by a spin coating method under conditions of at 2,000 rpm and for 20 seconds. The coating film forming composition was spin-coated and was subjected to drying at room temperature to remove the solvent, which was then subjected to exposure in the air using a UV irradiation apparatus as an exposure apparatus. The film thickness was set to 500 nm. As the base material, a 4-inch silicon wafer was used. As the base material, a 4-inch silicon wafer was used.

Example 64

In the same manner as in Example 1, Boc-Arg was added to the polysiloxane vanish PSV 2 obtained in Synthesis Example 2 to prepare a coating film forming composition (hereinafter, abbreviated as "PSV 2-BArg"). The coating film forming composition (PSV 2-BArg) was spin-coated and was subjected to drying at room temperature to remove the solvent, which was then subjected to exposure in the air using a UV irradiation apparatus in an exposure amount of 1 $J/cm^2$ (converted into energy at 250 nm). The coating film after exposure was pared off and the resultant sample piece was subjected to an FT-IR spectrum measurement by a KBr method.

Example 65

In the same manner as in Example 1, Boc-Lys was added to the polysiloxane vanish PSV 2 obtained in Synthesis Example 2 to prepare a coating film forming composition (hereinafter, abbreviated as "PSV 2-BLys"). The coating film forming composition (PSV 2-BLys) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 66

In the same manner as in Example 1, Boc-His was added to the polysiloxane vanish PSV 2 obtained in Synthesis Example 2 to prepare a coating film forming composition (hereinafter, abbreviated as "PSV 2-BHis"). The coating film forming composition (PSV 2-BHis) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 67

In the same manner as in Example 1, Boc-Arg was added to the polysiloxane vanish PSV 3 obtained in Synthesis Example 3 to prepare a coating film forming composition (hereinafter, abbreviated as "PSV 3-BArg"). The coating film forming composition (PSV 3-BArg) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 68

In the same manner as in Example 1, Boc-Lys was added to the polysiloxane vanish PSV 3 obtained in Synthesis Example 3 to prepare a coating film forming composition (hereinafter, abbreviated as "PSV 3-BLys"). The coating film forming composition (PSV 3-BLys) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 69

In the same manner as in Example 1, Boc-His was added to the polysiloxane vanish PSV 3 obtained in Synthesis Example 3 to prepare a coating film forming composition (hereinafter, abbreviated as "PSV 3-BHis"). The coating film forming composition (PSV 3-BHis) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 70

In the same manner as in Example 1, Boc-Arg was added to the polysiloxane vanish PSV 4 obtained in Synthesis Example 4 to prepare a coating film forming composition (hereinafter, abbreviated as "PSV 4-BArg"). The coating film forming composition (PSV 4-BArg) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 71

In the same manner as in Example 1, Boc-Lys was added to the polysiloxane vanish PSV 4 obtained in Synthesis Example 4 to prepare a coating film forming composition (hereinafter, abbreviated as "PSV 4-BLys"). The coating film forming composition (PSV 4-BLys) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 72

In the same manner as in Example 1, Boc-His was added to the polysiloxane vanish PSV 4 obtained in Synthesis Example 4 to prepare a coating film forming composition (hereinafter, abbreviated as "PSV 4-BHis"). The coating film forming composition (PSV 4-BHis) was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 46

The polysiloxane vanish PSV 2 obtained in Synthesis Example 2 and used as the coating film forming composition was spin-coated and was subjected to drying at room temperature to remove the solvent and not subjected to exposure. The coating film after drying was pared off and the resultant sample piece was subjected to an FT-IR spectrum measurement by a KBr method.

Comparative Example 47

The polysiloxane vanish PSV 3 obtained in Synthesis Example 2 and used as the coating film forming composition was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 48

The polysiloxane vanish PSV 3 obtained in Synthesis Example 2 and used as the coating film forming composition was spin-coated and was subjected to drying at room temperature to remove the solvent, which was then subjected to exposure in the air using a UV irradiation apparatus in an exposure amount of 5 J/cm$^2$ (converted into energy at 250 nm). The coating film after exposure was pared off and the resultant sample piece was subjected to an FT-IR spectrum measurement by a KBr method.

Comparative Example 49

The polysiloxane vanish PSV 4 obtained in Synthesis Example 3 and used as the coating film forming composition was spin-coated and was subjected to drying at room temperature to remove the solvent and not subjected to exposure. The coating film after drying was pared off and the resultant sample piece was subjected to an FT-IR spectrum measurement by a KBr method.

Comparative Example 50

The polysiloxane vanish PSV 4 obtained in Synthesis Example 3 and used as the coating film forming composition was spin-coated and was subjected to drying at room temperature to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 51

The polysiloxane vanish PSV 3 obtained in Synthesis Example 3 and used as the coating film forming composition was spin-coated and was subjected to drying at room temperature to remove the solvent, which was then subjected to exposure in the air using a UV irradiation apparatus in an exposure amount of 5 J/cm$^2$ (converted into energy at 250 nm). The coating film after exposure was pared off and the resultant sample piece was subjected to an FT-IR spectrum measurement by a KBr method.

Comparative Example 52

The polysiloxane vanish PSV 4 obtained in Synthesis Example 4 and used as the coating film forming composition was spin-coated and was subjected to drying at room temperature to remove the solvent and not subjected to exposure. The coating film after drying was pared off and the resultant sample piece was subjected to an FT-IR spectrum measurement by a KBr method.

Comparative Example 53

The polysiloxane vanish PSV 4 obtained in Synthesis Example 4 and used as the coating film forming composition was spin-coated and was subjected to drying at room temperature to remove the solvent, which was then subjected to exposure in the air using an UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 54

The polysiloxane vanish PSV 4 obtained in Synthesis Example 4 and used as the coating film forming composition was spin-coated and was subjected to drying at room temperature to remove the solvent, which was then subjected to exposure in the air using a UV irradiation apparatus in an exposure amount of 5 J/cm$^2$ (converted into energy at 250 nm). The coating film after exposure was pared off and the resultant sample piece was subjected to an FT-IR spectrum measurement by a KBr method.

The results of Examples 64 to 66 and Comparative Examples 46 to 48 are shown in FIGS. 63 to 65 and FIGS. 84 and 86; the results of Examples 67 to 69 and Comparative Examples 49 to 51 are shown in FIGS. 66 to 68 and FIGS. 87 to 89; and the results of Examples 70 to 72 and Comparative Examples 52 to 54 are shown in FIGS. 69 to 71 and FIGS. 90 to 92.

As shown in FIGS. 63 to 71, it was found that a film obtained from a coating film forming composition in which arginine having particularly high ability of accelerating the condensation-polymerization of the polysiloxane as the photo amino acid generator was added to a polysiloxane vanish is effective for digesting the Si—OH bond also with respect to the polysiloxane vanishes PSV 2 to 4 just like with respect to PSV 1. This result indicates that all of the polysiloxane vanish PSV 1 synthesized from a tetrafunctional silane monomer (hydrolyzable silane monomer having four hydrolyzable groups), the polysiloxane vanish PSV 2 obtained by copolymerizing a tetrafunctional silane monomer (hydrolyzable silane monomer having four hydrolyzable groups) with a trifunctional silane monomer (hydrolyzable silane monomer having three hydrolyzable groups), the polysiloxane vanish PSV 3 obtained by copolymerizing a tetrafunctional silane monomer (hydrolyzable silane monomer having four hydrolyzable groups), a trifunctional silane monomer (hydrolyzable silane monomer having three hydrolyzable groups), and a bifunctional silane monomer (hydrolyzable silane monomer having two hydrolyzable groups), and the polysiloxane vanish PSV 4 synthesized from a trifunctional silane monomer (hydrolyzable silane monomer having three hydrolyzable groups) has the effect, so that a general polysiloxane polymer can reduce Si—OH bonds with an exposure amount of around 1 J/cm$^2$.

It was also found that in the case of the coating film forming composition containing the polysiloxane vanish PSV 2 or PSV 3 to which no photo amino acid generator is added, even when the composition is subjected to a 5 J/cm$^2$ exposure, Si—OH bonds remain.

[Effect after Solvent-Exchange]

It was investigated whether the same effect as the effect by adding the photo amino acid generator beforehand can be obtained or not by adding the photo amino acid generator to a polysiloxane vanish after the solvent-exchange in the polysiloxane vanish during the synthesis of the polysiloxane vanishes obtained in Synthesis Examples 1 to 4.

The film formation was performed by a spin coating method under conditions of at 2,000 rpm and for 20 seconds. The coating film forming composition was spin-coated and was subjected to drying at 150° C. for 5 minutes to remove the solvent, which was then subjected to exposure in the air using a UV irradiation apparatus as an exposure apparatus. The film thickness was set to 500 nm. Here, baking at 150° C. for 5 minutes is a process for completely removing PGMEA as the solvent and at this time, it was confirmed that the photo amino acid generator is not decomposed. That is, under the baking conditions of at 150° C. and for 5 minutes, the condensation-polymerization of Si—OH bonds with each other is not accelerated and only during the following light irradiation, the condensation-polymerization is accelerated. As the base material, a 4-inch silicon wafer was used.

Example 73

To the polysiloxane vanish PSV 1 obtained in Synthesis Example 1, 94.84 g of propylene glycol monomethyl ether acetate (hereinafter, abbreviated as "PGMEA") that is the same amount of ethanol used as the solvent during the hydrolysis and condensation reactions of PGMEA was added and then, using an evaporator, the solvent-exchange was performed under conditions of at 20° C. of a water bath temperature and under reduced pressure for 6 hours.

To the obtained polysiloxane vanish after the solvent-exchange, Boc-Arg was added in the same manner as in Example 1 to obtain a coating film forming composition (hereinafter, abbreviated as "PSV 1-BArg-PGMEA").

The obtained coating film forming composition (PSV 1-BArg-PGMEA) was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 74

The polysiloxane vanish PSV 2 obtained in Synthesis Example 2 was subjected to the solvent-exchange to PGMEA in the same manner as in Example 73 and thereto, Boc-Arg was added.

The obtained coating film forming composition (hereinafter, abbreviated as "PSV 2-Boc-Arg-PGMEA") was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 75

The polysiloxane vanish PSV 3 obtained in Synthesis Example 3 was subjected to the solvent-exchange to PGMEA in the same manner as in Example 73 and thereto, Boc-Arg was added.

The obtained coating film forming composition (hereinafter, abbreviated as "PSV 3-Boc-Arg-PGMEA") was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Example 76

The polysiloxane vanish PSV 4 obtained in Synthesis Example 4 was subjected to the solvent-exchange to PGMEA in the same manner as in Example 73 and thereto, Boc-Arg was added.

The obtained coating film forming composition (hereinafter, abbreviated as "PSV 4-Boc-Arg-PGMEA") was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 55

To the polysiloxane vanish PSV 1 obtained in Synthesis Example 1, 94.84 g of PGMEA that is the same amount of ethanol used as the solvent during the hydrolysis and condensation reactions of PGMEA was added and then, using an evaporator, the solvent-exchange was performed under conditions of at 20° C. of a water bath temperature and under reduced pressure for 6 hours.

The obtained coating film forming composition (hereinafter, abbreviated as "PSV 1-PGMEA") after the solvent-exchange was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 56

The polysiloxane vanish PSV 2 obtained in Synthesis Example 2 was subjected to the solvent-exchange to PGMEA in the same manner as in Comparative Example 55.

The obtained coating film forming composition (hereinafter, abbreviated as "PSV 2-PGMEA) was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 57

The polysiloxane vanish PSV 3 obtained in Synthesis Example 3 was subjected to the solvent-exchange to PGMEA in the same manner as in Comparative Example 55.

The obtained coating film forming composition (hereinafter, abbreviated as "PSV 3-PGMEA) was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

Comparative Example 58

The polysiloxane vanish PSV 4 obtained in Synthesis Example 4 was subjected to the solvent-exchange to PGMEA in the same manner as in Comparative Example 55.

The obtained coating film forming composition (hereinafter, abbreviated as "PSV 3-PGMEA") was spin-coated and was subjected to drying at 150° C. for 5 minutes to remove the solvent, which was then subjected to exposure in the air using a UV irradiation apparatus in an exposure amount of 1 J/cm$^2$ (converted into energy at 250 nm). The coating film after exposure was pared off and the resultant sample piece was subjected to an FT-IR spectrum measurement by a KBr method.

The results of Examples 73 to 76 and Comparative Examples 55 to 58 are shown in FIGS. 72 to 75 and FIGS. 93 to 96.

As shown in FIGS. 72 to 75, also in a polysiloxane vanish in which the solvent of the polysiloxane vanish is solvent-exchanged from ethanol that is the solvent used during the hydrolysis and condensation reactions to PGMEA, the effect of the photo amino acid generator was developed, so that it was found that even when a different solvent type is used, the Si—OH bond in the film can be remarkably digested.

As described above, from the above results, it could be confirmed that a polysiloxane composition in which a photo amino acid generator is added to a polysiloxane vanish can maintain advantageous preservation stability of the polysiloxane vanish, can accelerate the condensation-polymerization during baking, and can remarkably reduce remaining Si—OH bonds, so that the polysiloxane composition is effective as the coating film forming composition.

Preparation of Polysiloxane Vanish Containing Crosslinkable Compound

Example 77

To 100 g of PSV 2 (SiO$_2$ solid content-converted concentration: 12% by mass) obtained in Synthesis Example 2, 0.12 g (1 phr) of a glycoluril compound (trade name: POWDERLINK 1174; manufactured by Mitsui Cytec Ltd.) as the organic crosslinkable compound was added and the resultant mixture was stirred at room temperature for about 2 hours to completely dissolve the solid. Then, a polysiloxane composition (hereinafter, abbreviated as "PSV 2-PWL1 phr") containing an organic crosslinkable compound was prepared as a colorless transparent solution.

Example 78

To 100 g of PSV 2 (SiO$_2$ solid content-converted concentration: 12% by mass) obtained in Synthesis Example 2, 0.60 g (5 phr) of a glycoluril compound (trade name: POWDERLINK 1174; manufactured by Mitsui Cytec Ltd.) as the organic crosslinkable compound was added and the resultant mixture was stirred at room temperature for about 2 hours to completely dissolve the solid. Then, a polysiloxane composition (hereinafter, abbreviated as "PSV 2-PWL5 phr") containing an organic crosslinkable compound was prepared as a colorless transparent solution.

Example 79

To 100 g of PSV 2 (SiO$_2$ solid content-converted concentration: 12% by mass) obtained in Synthesis Example 2, 1.20 g (10 phr) of a glycoluril compound (trade name: POWDERLINK 1174; manufactured by Mitsui Cytec Ltd.) as the organic crosslinkable compound was added and the resultant mixture was stirred at room temperature for about 2 hours to completely dissolve the solid. Then, a polysiloxane composition (hereinafter, abbreviated as "PSV 2-PWL10 phr") containing an organic crosslinkable compound was prepared as a colorless transparent solution.

Example 80

To 100 g of PSV 2 (SiO$_2$ solid content-converted concentration: 12% by mass) obtained in Synthesis Example 2, 2.40 g (20 phr) of a glycoluril compound (trade name: POWDERLINK 1174; manufactured by Mitsui Cytec Ltd.) as the organic crosslinkable compound was added and the resultant mixture was stirred at room temperature for about 2 hours to completely dissolve the solid. Then, a polysiloxane composition (hereinafter, abbreviated as "PSV 2-PWL20 phr") containing an organic crosslinkable compound was prepared as a colorless transparent solution.

[Confirmation of Filling Property in Via]

Measurement Example 1

A via substrate was spin-coated with each of the polysiloxane vanish (PVS 2) obtained in Synthesis Example 2 and polysiloxane compositions obtained in Examples 77 to 80 as the coating film forming composition and the composition was baked in the air using a hot plate at 400° C. for 5 minutes and subjected to an SEM observation. The spin-coating was performed under conditions of at 2,000 rpm and for 30 seconds.

Measurement Example 2

A via substrate was spin-coated with the polysiloxane composition obtained in Example 78 as the coating film forming composition and the composition was baked in the air using a hot plate at 400° C. for 15 minutes, 30 minutes, or 60 minutes and subjected to an SEM observation. The spin-coating was performed under conditions of at 2,000 rpm and for 30 seconds.

Figure 97:
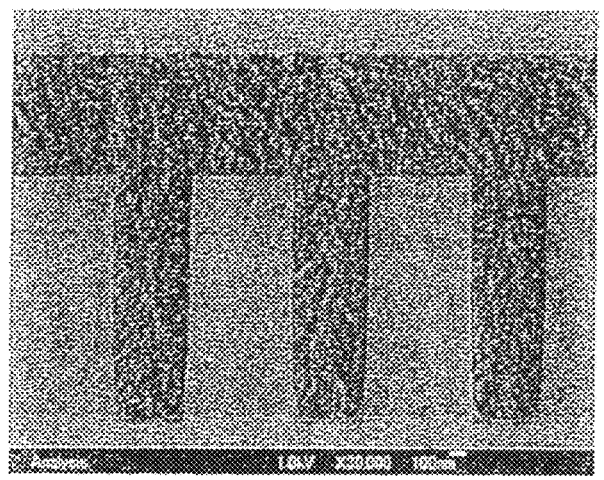
FIG. 97 is a photograph showing a cross section view of a via in which the polysiloxane composition is filled by a spin coating method and the composition is cured, where the photograph shows advantageous filling property.
Figure 98:
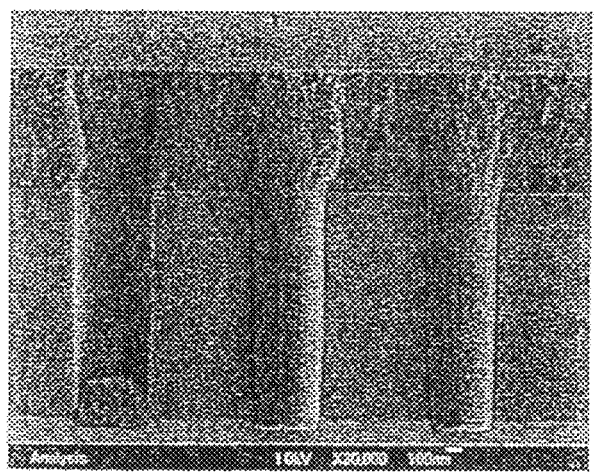
FIG. 98 is a photograph showing a cross section view of a via in which the polysiloxane composition is filled by a spin coating method and the composition is cured, where a slit is formed, so that the photograph shows undesirable filling property.

Examples of the filling property in a via substrate after baking are shown in FIGS. 97 and 98. FIG. 97 is a cross section view of a via in which filling property is advantageous and FIG. 98 is a cross section view of a via in which filling was accompanied by a slit, which is not so preferred.

TABLE 3

| Filling property | Solute | Baking condition |
|---|---|---|
| Measurement Example 1 With slit | — | 400° C. × 5 minutes |
| Measurement Example 1 With slit | PSV 2-PWL 1phr | 400° C. × 5 minutes |
| Measurement Example 1 Advantageous | PSV 2-PWL 5phr | 400° C. × 5 minutes |
| Measurement Example 1 Advantageous | PSV 2-PWL 10phr | 400° C. × 5 minutes |
| Measurement Example 1 Advantageous | PSV 2-PWL 20phr | 400° C. × 5 minutes |
| Measurement Example 2 Advantageous | PSV 2-PWL 5phr | 400° C. × 15 minutes |
| Measurement Example 2 Advantageous | PSV 2-PWL 5phr | 400° C. × 30 minutes |
| Measurement Example 2 advantageous | PSV 2-PWL 5phr | 400° C. × 60 minutes |

Example 81

To 100 g of the polysiloxane vanish PSV 2 (SiO$_2$ solid content-converted concentration: 12% by mass) obtained in Synthesis Example 2, 1.20 g (10 phr) of a glycoluril compound (trade name: POWDERLINK 1174; manufactured by Mitsui Cytec Ltd.) as the organic crosslinkable compound and 0.12 g (1 phr, that is, the composition contains 1 part by mass thereof relative to 100 parts by mass of $SiO_2$) of N-α, N-ω1, N-ω2-tri-tert-butoxycarbonyl-L-arginine (hereinafter, abbreviated as "Boc-Arg", where D is a protecting group for an amino group) of Formula (A-2) as the amino acid generator, were added and the resultant mixture was stirred at room temperature for 30 minutes to completely dissolve Boc-Arg. Then, a polysiloxane composition containing an organic crosslinkable compound and an amino acid generator was prepared as a colorless transparent solution as a coating film forming composition (hereinafter, abbreviated as "PSV 2-PWL-BArg").

Example 82

In the same manner as in Example 81, except that as the amino acid generator, N-α, N-ε-di-tert-butoxycarbonyl-L-lysine (hereinafter, abbreviated as "Boc-Lys", where D is a protecting group for an amino group) of Formula (A-6) was used, a polysiloxane composition containing an organic crosslinkable compound and an amino acid generator was prepared as a coating film forming composition (hereinafter, abbreviated as "PSV 2-PWL-BLys").

Example 83

In the same manner as in Example 81, except that as the amino acid generator, N-α-tert-butoxycarbonyl-N-δ-(9-fluorenylmethoxycarbonyl)-L-ornithine (hereinafter, abbreviated as "FB-Orn", where $D_1$ and $D_2$ are protecting groups for an amino group) of Formula (A-8) was used, a polysiloxane composition containing an organic crosslinkable compound and an amino acid generator was prepared as a coating film forming composition (hereinafter, abbreviated as "PSV 2-PWL-FBOrn").

[Behavior of Reducing Si—OH Bonds According to Baking Conditions]

A coating film forming composition was produced using a polysiloxane composition containing an amino acid generator and there was confirmed the variation in the behavior of reducing Si—OH bonds according to the variation in the baking condition when a coating film is produced by coating a substrate with the coating film forming composition.

The production of a film was performed by spin-coating a substrate (base material) with the coating film forming composition under conditions of at 2,000 rpm and for 20 seconds. The coating film forming composition was spin-coated and was baked in the air using a hot plate as baking equipment. The film thickness was set at 500 nm. As the base material, a 4-inch silicon wafer was used.

Example 84

The coating film forming composition (PSV 2-PWL-BArg) obtained in Example 81 was spin-coated and was baked at 250° C. for 5 minutes. The coating film after baking was pared off and the resultant sample piece was subjected to an FT-IR spectrum measurement by a KBr method.

Example 85

In the same manner as in Example 84, except that the coating film forming composition (PSV 2-PWL-BLys) obtained in Example 82 was used, the coating film was formed and a sample piece thereof was subjected to an FT-IR spectrum measurement.

Example 86

In the same manner as in that Example 84, except that the coating film forming composition (PSV 2-PWL-FBOrn) obtained in Example 83 was used, the coating film was formed and a sample piece thereof was subjected to an FT-IR spectrum measurement.

Comparative Example 59

In the same manner as in Example 84, except that as the coating film forming composition, the polysiloxane vanish (PSV 2) obtained in Synthesis Example 2 was used, the coating film was formed and a sample piece thereof was subjected to an FT-IR spectrum measurement.

Comparative Example 1

In the same manner as in Example 8, except that as the coating film forming composition, the polysiloxane vanish (PSV 2-PWL 10 phr) obtained in Example 79 was used, the coating film was formed and a sample piece thereof was subjected to an FT-IR spectrum measurement.

The results of the FT-IR measurement in Examples 84 to 86, Comparative Example 59, and Reference Example 1 are shown in FIGS. 99 to 103. In the figures, there was focused attention on a peak at around 3,500 $cm^{-1}$ ascribed to an OH stretching vibration of a Si—OH bond.

Figure 99:
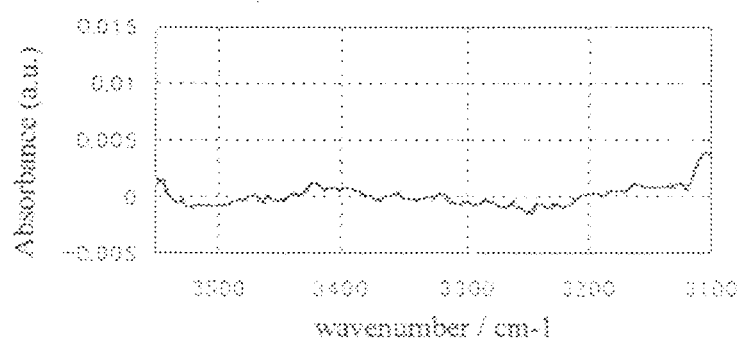
FIG. 99 is a graph showing an FT-IR spectrum of the film obtained in Example 84.
Figure 100:
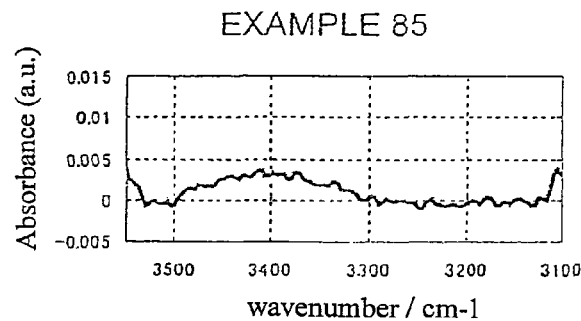
FIG. 100 is a graph showing an FT-IR spectrum of the film obtained in Example 85.
Figure 101:
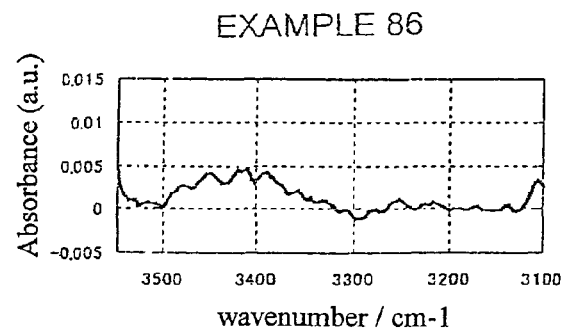
FIG. 101 is a graph showing an FT-IR spectrum of the film obtained in Example 86.

In FIGS. 99 to 101, the number of Si—OH bonds of a film produced by baking at 250° C. for 5 minutes, the film formed from a coating film forming composition in which an amino acid generator was added to the polysiloxane vanish (PSV 2), was remarkably reduced.

Figure 102:
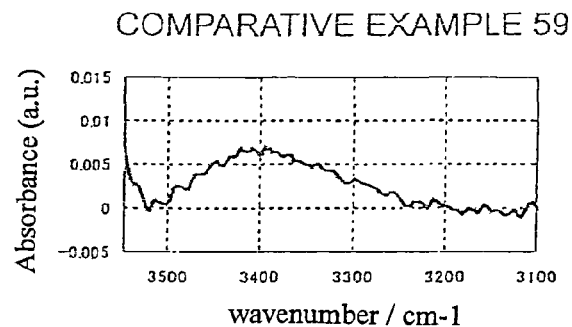
FIG. 102 is a graph showing an FT-IR spectrum of the film obtained in Comparative Example 59.
Figure 103:
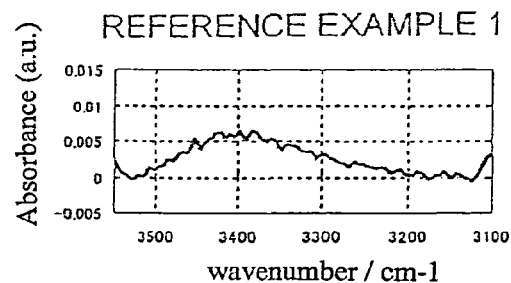
FIG. 103 is a graph showing an FT-IR spectrum of the film obtained in Reference Example 1.

In a film produced by baking at 250° C. for 5 minutes, the film formed from as the coating film forming composition, the polysiloxane vanish (PSV 2) of Comparative Example 59 in FIG. 102, and in a film produced by baking at 250° C. for 5 minutes, the film formed from the coating film forming composition (PSV 2-PWL 10 phr) of Reference Example 1 in FIG. 103, remarkably many Si—OH bonds remained.

As described above, from the above results, it could be confirmed that a polysiloxane composition in which an amino acid generator is added to a polysiloxane vanish can accelerate the condensation-polymerization during baking and can remarkably reduce remaining Si—OH bonds, so that such a polysiloxane composition is effective as the coating film forming composition.

From the results shown above, it was confirmed that a polysiloxane composition in which an organic crosslinkable compound is added to a polysiloxane vanish has advantageous filling property. Further, it could also be confirmed that a polysiloxane composition in which an organic crosslinkable compound and an amino acid generator are added to a polysiloxane vanish has advantageous filling property, can accelerate the condensation-polymerization during baking, and can remarkably reduce remaining Si—OH bonds, so that such a polysiloxane composition is effective as the coating film forming composition. Thus, the above polysiloxane composition can enhance filling property in a via and can remarkably reduce remaining Si—OH bonds, so that various polysiloxane compositions can be designed and the process margin can be enlarged. Thus, the above polysiloxane composition can be preferably used as one member of an electronic device, particularly a solid state imaging device.

INDUSTRIAL APPLICABILITY

The coating film forming composition containing the amino acid generator of the present invention can control pH of the polysiloxane vanish during the preservation and baking or light irradiation by varying the type of the amino acid generator, so that polysiloxane compositions corresponding to device types to be produced and various baking processes can be designed and the process margin can be enlarged. Accordingly, the coating film forming composition of the present invention can preferably be used as one member of an electronic device, particularly a solid state imaging device.

The coating film forming composition of the present invention can be applied to a solid state imaging device containing a charge coupled device (CCD) or a complementary metal oxide film semiconductor (CMOS) that contains a film formed from the coating film forming composition of the present invention, to a solid state imaging device containing the above film as a planarization layer on a color filter, and to a solid state imaging device containing the above film as a planarization layer or a conformal layer on a microlens.

What is claimed is:

1. A coating film forming composition comprising:
   a component (A): an amino acid generator comprising a protecting group that is eliminated to generate an amino acid;
   a component (B): a hydrolyzable silane, a hydrolysis product thereof, a hydrolysis-condensation product thereof, or a mixture thereof; and
   a component (C): a solvent,
   wherein the amino acid generator is at least one type of compound selected from the group consisting of compounds of Formula (2-1) to Formula (2-22):

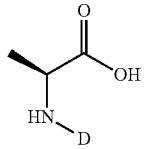

Formula (2-1)

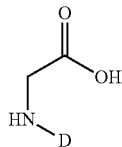

Formula (2-2)

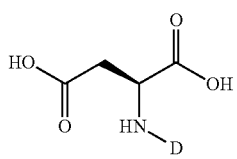

Formula (2-3)

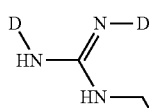

Formula (2-4)

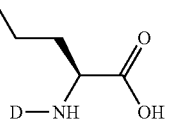

Formula (2-5)

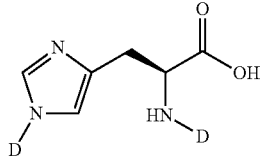

-continued

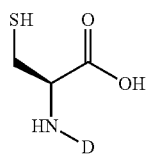

Formula (2-6)

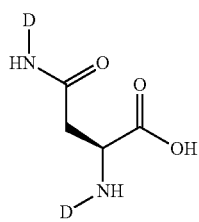

Formula (2-7)

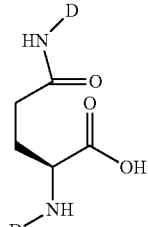

Formula (2-8)

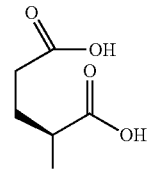

Formula (2-9)

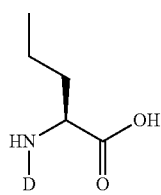

Formula (2-10)

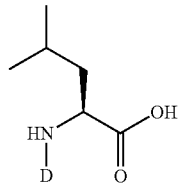

Formula (2-11)

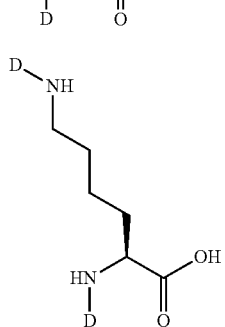

Formula (2-12)

-continued

Formula (2-13)
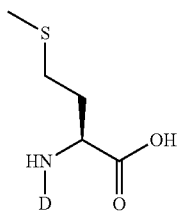

Formula (2-14)
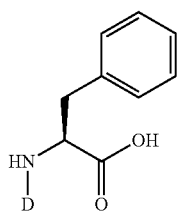

Formula (2-15)
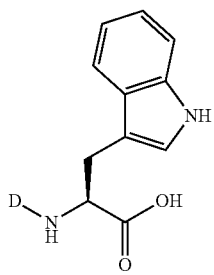

Formula (2-16)
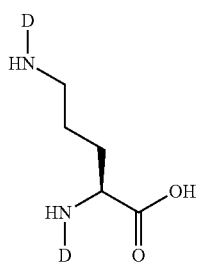

Formula (2-17)
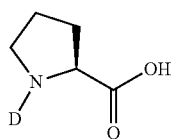

Formula (2-18)
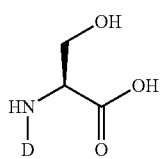

Formula (2-19)
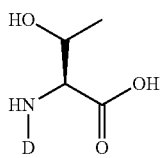

Formula (2-20)
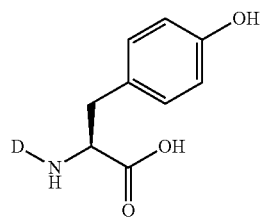

Formula (2-21)
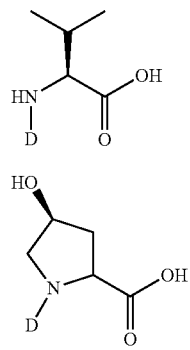

Formula (2-22)

where:
D is the protecting group and is one selected from the group consisting of a tert-butoxycarbonyl group and a 9-fluorenylmethoxycarbonyl group.

2. The coating film forming composition according to claim 1, wherein the amino acid generator is a thermo amino acid generator comprising a protecting group that is eliminated by heat to generate an amino acid.

3. The coating film forming composition according to claim 1, wherein the amino acid generator is a photo amino acid generator comprising a protecting group that is eliminated by light to generate an amino acid.

4. The coating film forming composition according to claim 1, wherein the component (B) is at least one selected from the group consisting of a hydrolyzable silane, a hydrolysis product thereof, a hydrolysis-condensation product therefore, and a mixture thereof, wherein the hydrolysable silane is selected from the group consisting of Formula (3) and Formula (4):

$$R^3_a Si(R^4)_{4-a} \quad \text{Formula (3)}$$

where:
$R^3$ is an alkyl group, an aryl group, a halogenated alkyl group, a halogenated aryl group, an alkenyl group, or an organic group having an epoxy group, an acryloyl group, a methacryloyl group, a mercapto group, an amino group, a carboxy group, a phosphate group, an amide group, a nitro group, an acyl group, a sulfonic group, a cyano group, or a combination thereof;
$R^3$ is bonded to a silicon atom through a Si—C bond;
$R^4$ is an alkoxy group, an acyloxy group, or a halogen atom; and
a is an integer of 0 to 3, $$[R^5_c Si(R^6)_{3-c}]_2 Y_b \quad \text{Formula (4)}$$

where:
$R^5$ is an alkyl group, an aryl group, a halogenated alkyl group, a halogenated aryl group, an alkenyl group, or an organic group having an epoxy group, an acryloyl group, a methacryloyl group, a mercapto group, an amino group, a carboxy group, a phosphate group, an amide group, a nitro group, an acyl group, a sulfonic group, a cyano group, or a combination thereof;

$R^5$ is bonded to a silicon atom through a Si—C bond;

$R^6$ is an alkoxy group, an acyloxy group, or a halogen atom;

Y is an alkylene group or an arylene group;

b is an integer of 0 or 1; and c is an integer of 0 or 1.

5. The coating film forming composition according to claim 4, wherein the hydrolysable silane is Formula (3), where a is 0 to 2.

6. The coating film forming composition according to claim 4, further comprising a crosslinkable compound as a component (D).

7. The coating film forming composition according to claim 6, wherein the crosslinkable compound has at least two functional groups of Formula (D-1):

$$—CH_2—O—R^1 \quad \text{Formula (D-1)}$$

where $R^1$ is a hydrogen atom or a $C_{1\text{-}10}$ alkyl group.

8. The coating film forming composition according to claim 6, wherein:

the crosslinkable compound has Formula (D-2) or Formula (D-4):

Formula (D-2)

where $R^6$ is a hydrogen atom, a $C_{1\text{-}10}$ alkyl group, an aryl group, an aralkyl group, an alkenyl group, or a functional group of Formula (D-3):

Formula (D-3)

where $R^7$ is a hydrogen atom or a functional group of Formula (D-1):

$$—CH_2—O—R^1 \quad \text{Formula (D-1),}$$

and

Formula (D-2) has two to six functional groups of Formula (D-1), (Formula (D-4))

$R^8$ is a hydrogen atom or a functional group of Formula (D-1),

Formula (D-4) has two to four functional groups of Formula (D-1).

9. An electronic device comprising a film formed from the coating film forming composition as claimed in claim 1.

10. A solid state imaging device comprising a charge coupled device (CCD) or a complementary metal oxide film semiconductor (CMOS) that comprises a film formed from the coating film forming composition as claimed in claim 1.

11. A solid state imaging device comprising a film formed from the coating film forming composition as claimed in claim 1 as a planarization layer on a color filter.

12. A solid state imaging device comprising a film formed from the coating film forming composition as claimed in claim 1 as a planarization layer or a conformal layer on a microlens.

* * * * *